United States Patent
Ou et al.

(10) Patent No.: US 10,228,550 B2
(45) Date of Patent: Mar. 12, 2019

(54) LASER-BASED FOURIER PTYCHOGRAPHIC IMAGING SYSTEMS AND METHODS

(71) Applicant: California Institute of Technology, Pasadena, CA (US)

(72) Inventors: Xiaoze Ou, Pasadena, CA (US); Jaebum Chung, Pasadena, CA (US); Changhuei Yang, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 157 days.

(21) Appl. No.: 15/160,941

(22) Filed: May 20, 2016

(65) Prior Publication Data
US 2016/0341945 A1     Nov. 24, 2016

Related U.S. Application Data

(60) Provisional application No. 62/165,084, filed on May 21, 2015.

(51) Int. Cl.
*G01B 9/02* (2006.01)
*G02B 21/00* (2006.01)
(Continued)

(52) U.S. Cl.
CPC ..... *G02B 21/0032* (2013.01); *G01N 21/8806* (2013.01); *G01N 21/8851* (2013.01);
(Continued)

(58) Field of Classification Search
CPC ............ G01B 9/02024; G01B 9/02043; G01B 9/02084; G01B 9/02085; G02B 21/0048;
(Continued)

(56) References Cited

U.S. PATENT DOCUMENTS

| | | |
|---|---|---|
| 5,475,527 A | 12/1995 | Hackel et al. |
| 6,144,365 A | 11/2000 | Young et al. |

(Continued)

FOREIGN PATENT DOCUMENTS

| | | |
|---|---|---|
| CN | 101408623 A | 4/2009 |
| CN | 101868740 A | 10/2010 |

(Continued)

OTHER PUBLICATIONS

U.S. Appl. No. 15/007,196, filed Jan. 26, 2016 entitled "Array Level Fourier Ptychographic Imaging".

(Continued)

*Primary Examiner* — Jonathan M Hansen
(74) *Attorney, Agent, or Firm* — Sheila Martinez-Lemke; Weaver Austin Villeneuve & Sampson LLP

(57) ABSTRACT

Certain embodiments pertain to laser-based Fourier ptychographic (LFP) imaging systems, angle direction devices used in the LFP imaging systems, optical switches used in the LFP imaging systems, and LFP imaging methods. The LFP systems include an angle direction device for directing laser light to a sample plane at a plurality of illumination angles at different sample times. The LFP systems also include an optical system and a light detector. The optical system receives light issuing from the sample being imaged and propagates and focuses the light to the light detector acquiring raw intensity images.

22 Claims, 15 Drawing Sheets

US 10,228,550 B2
Page 2

(51) Int. Cl.
| | |
|---|---|
| H04N 7/18 | (2006.01) |
| H04N 5/225 | (2006.01) |
| G01N 21/88 | (2006.01) |
| G02B 21/08 | (2006.01) |
| G02B 21/36 | (2006.01) |
| G02B 26/10 | (2006.01) |

(52) U.S. Cl.
CPC ....... *G02B 21/0048* (2013.01); *G02B 21/086* (2013.01); *G02B 21/367* (2013.01); *G02B 26/101* (2013.01); *G02B 26/105* (2013.01); *H04N 5/2256* (2013.01); *H04N 7/18* (2013.01); *G01N 2021/8822* (2013.01); *G01N 2201/06113* (2013.01)

(58) Field of Classification Search
CPC ............ G02B 21/0052; G02B 21/0056; G02B 21/006
See application file for complete search history.

(56) References Cited

U.S. PATENT DOCUMENTS

| | | | |
|---|---|---|---|
| 6,154,196 | A | 11/2000 | Fleck et al. |
| 6,320,174 | B1 | 11/2001 | Tafas et al. |
| 6,320,648 | B1 | 11/2001 | Brueck et al. |
| 6,747,781 | B2 | 6/2004 | Trisnadi |
| 6,905,838 | B1 | 6/2005 | Bittner |
| 7,436,503 | B1 | 10/2008 | Chen et al. |
| 7,460,248 | B2 | 12/2008 | Kurtz et al. |
| 7,706,419 | B2 | 4/2010 | Wang et al. |
| 7,787,588 | B1 | 8/2010 | Yun et al. |
| 8,271,251 | B2 | 9/2012 | Schwartz et al. |
| 8,313,031 | B2 | 11/2012 | Vinogradov |
| 8,497,934 | B2 | 7/2013 | Milnes et al. |
| 8,624,968 | B1 | 1/2014 | Zheng et al. |
| 8,942,449 | B2 | 1/2015 | Maiden |
| 9,029,745 | B2 | 5/2015 | Maiden |
| 9,426,455 | B2 | 8/2016 | Horstmeyer et al. |
| 9,497,379 | B2 | 11/2016 | Ou et al. |
| 9,829,695 | B2 | 11/2017 | Kim et al. |
| 9,864,184 | B2 | 1/2018 | Ou et al. |
| 9,892,812 | B2 | 2/2018 | Zheng et al. |
| 9,983,397 | B2 | 5/2018 | Horstmeyer et al. |
| 9,993,149 | B2 | 6/2018 | Chung et al. |
| 9,998,658 | B2 | 6/2018 | Ou et al. |
| 10,162,161 | B2 | 12/2018 | Horstmeyer et al. |
| 10,168,525 | B2 | 1/2019 | Kim et al. |
| 2001/0055062 | A1 | 12/2001 | Shioda et al. |
| 2002/0141051 | A1 | 10/2002 | Vogt et al. |
| 2003/0116436 | A1 | 6/2003 | Amirkhanian et al. |
| 2004/0057094 | A1 | 3/2004 | Olszak et al. |
| 2004/0146196 | A1 | 7/2004 | Van Heel |
| 2004/0190762 | A1 | 9/2004 | Dowski, Jr. et al. |
| 2005/0211912 | A1 | 9/2005 | Fox |
| 2006/0098293 | A1 | 5/2006 | Garoutte et al. |
| 2006/0158754 | A1* | 7/2006 | Tsukagoshi ........ G02B 26/0833 359/851 |
| 2006/0173313 | A1 | 8/2006 | Liu et al. |
| 2006/0291707 | A1 | 12/2006 | Kothapalli et al. |
| 2007/0057184 | A1 | 3/2007 | Uto et al. |
| 2007/0133113 | A1 | 6/2007 | Minabe et al. |
| 2007/0159639 | A1 | 7/2007 | Teramura et al. |
| 2007/0171430 | A1 | 7/2007 | Tearney et al. |
| 2007/0189436 | A1 | 8/2007 | Goto et al. |
| 2007/0206200 | A1 | 9/2007 | Lindner et al. |
| 2008/0101664 | A1 | 5/2008 | Perez |
| 2008/0182336 | A1 | 7/2008 | Zhuang et al. |
| 2009/0046164 | A1 | 2/2009 | Shroff et al. |
| 2009/0079987 | A1 | 3/2009 | Ben-Ezra et al. |
| 2009/0125242 | A1* | 5/2009 | Choi ............... G01N 21/45 702/19 |
| 2009/0284831 | A1 | 11/2009 | Schuster et al. |
| 2009/0316141 | A1 | 12/2009 | Feldkhun |
| 2010/0135547 | A1 | 6/2010 | Lee et al. |
| 2010/0271705 | A1 | 10/2010 | Hung |
| 2011/0075928 | A1 | 3/2011 | Jeong et al. |
| 2011/0192976 | A1 | 8/2011 | Own et al. |
| 2011/0235863 | A1 | 9/2011 | Maiden |
| 2011/0255163 | A1 | 10/2011 | Merrill et al. |
| 2012/0069344 | A1 | 3/2012 | Liu |
| 2012/0099803 | A1 | 4/2012 | Ozcan et al. |
| 2012/0105618 | A1 | 5/2012 | Brueck et al. |
| 2012/0118967 | A1 | 5/2012 | Gerst |
| 2012/0157160 | A1 | 6/2012 | Ozcan et al. |
| 2012/0176673 | A1 | 7/2012 | Cooper |
| 2012/0218379 | A1 | 8/2012 | Ozcan et al. |
| 2012/0248292 | A1 | 10/2012 | Ozcan et al. |
| 2012/0250032 | A1 | 10/2012 | Wilde et al. |
| 2012/0281929 | A1 | 11/2012 | Brand et al. |
| 2013/0057748 | A1 | 3/2013 | Duparre et al. |
| 2013/0083886 | A1 | 4/2013 | Carmi et al. |
| 2013/0093871 | A1 | 4/2013 | Nowatzyk et al. |
| 2013/0094077 | A1 | 4/2013 | Brueck et al. |
| 2013/0100525 | A1 | 4/2013 | Chiang et al. |
| 2013/0170767 | A1 | 7/2013 | Choudhury et al. |
| 2013/0182096 | A1 | 7/2013 | Boccara et al. |
| 2013/0223685 | A1 | 8/2013 | Maiden |
| 2014/0007307 | A1 | 1/2014 | Routh, Jr. et al. |
| 2014/0029824 | A1 | 1/2014 | Shi et al. |
| 2014/0043616 | A1 | 2/2014 | Maiden et al. |
| 2014/0050382 | A1 | 2/2014 | Adie et al. |
| 2014/0118529 | A1 | 5/2014 | Zheng et al. |
| 2014/0126691 | A1 | 5/2014 | Zheng et al. |
| 2014/0133702 | A1 | 5/2014 | Zheng et al. |
| 2014/0152801 | A1 | 6/2014 | Fine et al. |
| 2014/0153692 | A1 | 6/2014 | Larkin et al. |
| 2014/0160236 | A1 | 6/2014 | Ozcan et al. |
| 2014/0160488 | A1 | 6/2014 | Zhou |
| 2014/0217268 | A1 | 8/2014 | Schleipen et al. |
| 2014/0267674 | A1 | 9/2014 | Mertz et al. |
| 2014/0347672 | A1 | 11/2014 | Pavillon et al. |
| 2014/0368812 | A1 | 12/2014 | Humphry et al. |
| 2015/0036038 | A1 | 2/2015 | Horstmeyer et al. |
| 2015/0054979 | A1 | 2/2015 | Ou et al. |
| 2015/0160450 | A1 | 6/2015 | Ou et al. |
| 2015/0264250 | A1 | 9/2015 | Ou et al. |
| 2015/0331228 | A1 | 11/2015 | Horstmeyer et al. |
| 2016/0088205 | A1 | 3/2016 | Horstmeyer et al. |
| 2016/0178883 | A1 | 6/2016 | Horstmeyer et al. |
| 2016/0202460 | A1 | 7/2016 | Zheng |
| 2016/0210763 | A1 | 7/2016 | Horstmeyer et al. |
| 2016/0216208 | A1 | 7/2016 | Kim et al. |
| 2016/0216503 | A1 | 7/2016 | Kim et al. |
| 2016/0266366 | A1 | 9/2016 | Chung et al. |
| 2016/0320595 | A1 | 11/2016 | Horstmeyer et al. |
| 2016/0320605 | A1 | 11/2016 | Ou et al. |
| 2017/0178317 | A1 | 6/2017 | Besley et al. |
| 2017/0273551 | A1 | 9/2017 | Chung et al. |
| 2017/0299854 | A1 | 10/2017 | Kim et al. |
| 2017/0354329 | A1 | 12/2017 | Chung et al. |
| 2017/0363853 | A1 | 12/2017 | Besley |
| 2017/0371141 | A1 | 12/2017 | Besley |
| 2018/0088309 | A1 | 3/2018 | Ou et al. |
| 2018/0307017 | A1 | 10/2018 | Horstmeyer et al. |
| 2018/0316855 | A1 | 11/2018 | Ou et al. |

FOREIGN PATENT DOCUMENTS

| | | |
|---|---|---|
| CN | 101872033 A | 10/2010 |
| CN | 102608597 A | 7/2012 |
| CN | 103201648 A | 7/2013 |
| JP | 2007-299604 A | 11/2007 |
| JP | 2010-012222 A | 1/2010 |
| KR | 10-1998-0075050 A | 11/1998 |
| WO | WO 99/53469 A1 | 10/1999 |
| WO | WO 2002/102128 A1 | 12/2002 |
| WO | 2003/062744 A1 | 7/2003 |
| WO | WO 2008/116070 A1 | 9/2008 |
| WO | WO 2011/093043 A1 | 8/2011 |
| WO | WO 2012/037182 A1 | 3/2012 |
| WO | WO 2014/070656 A1 | 5/2014 |
| WO | 2015/017730 A1 | 2/2015 |
| WO | 2015/027188 A1 | 2/2015 |

(56) References Cited

FOREIGN PATENT DOCUMENTS

| WO | WO 2015/027188 A1 | 2/2015 |
|---|---|---|
| WO | 2016/090331 | 6/2016 |
| WO | 2016/106379 A1 | 6/2016 |
| WO | 2016/118761 A1 | 7/2016 |
| WO | 2016/123156 A1 | 8/2016 |
| WO | 2016/123157 A1 | 8/2016 |
| WO | 2016/149120 A1 | 9/2016 |
| WO | 2016/187591 A1 | 11/2016 |
| WO | WO 2017081539 A1 | 5/2017 |
| WO | WO 2017081540 A1 | 5/2017 |
| WO | WO 2017081542 A2 | 5/2017 |

OTHER PUBLICATIONS

U.S. Appl. No. 15/007,159, filed Jan. 26, 2016 entitled "Multi-Well Fourier Ptychographic and Fluorescence Imaging".
U.S. Appl. No. 14/979,154, filed Dec. 22, 2015 entitled "EPI-Illumination Fourier Ptychographic Imaging for Thick Samples".
U.S. Appl. No. 15/003,559, filed Jan. 21, 2016 entitled "Fourier Ptychographic Tomography".
U.S. Appl. No. 15/068,389, filed Mar. 11, 2016 entitled "Correcting for Aberrations in Incoherent Imaging Systems Using Fourier Ptychographic Techniques".
U.S. Appl. No. 15/081,659, filed Mar. 25, 2016 entitled "Fourier Ptychographic Retinal Imaging Methods and Systems".
U.S. Office Action dated Oct. 5, 2015 in U.S. Appl. No. 14/065,305.
U.S. Notice of Allowance dated Dec. 4, 2015 in U.S. Appl. No. 14/065,305.
U.S. Notice of Allowance dated Jan. 14, 2016 in U.S. Appl. No. 14/448,850.
U.S. Notice of Allowance dated Jan. 22, 2016 in U.S. Appl. No. 14/466,481.
U.S. Notice of Allowance dated Apr. 13, 2016 in U.S. Appl. No. 14/448,850.
U.S. Notice of Allowance dated Apr. 22, 2016 in U.S. Appl. No. 14/466,481.
International Search Report and Written Opinion dated Feb. 21, 2014 in PCT/US2013/067068.
International Preliminary Report on Patentability dated May 14, 2015 in PCT/US2013/067068.
European Third-Party Observations, dated Jan. 20, 2016 in EP Application No. 13851670.3.
European Extended Search Report dated Mar. 31, 2016 in EP Application No. 13851670.3.
International Preliminary Report on Patentability dated Mar. 3, 2016 issued in PCT/US2014/052351.
International Search Report and Written Opinion dated Dec. 5, 2014 issued in PCT/US2014/052351.
International Search Report and Written Opinion dated Nov. 13, 2014 issued in PCT/US2014/049297.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
International Search Report and Written Opinion dated May 4, 2016 issued in PCT/US2016/015001.
International Search Report and Written Opinion dated May 11, 2016 issued in PCT/US2016/015002.
"About Molemap," Retrieved Oct. 23, 2015, 2 pages. [http://molemap.net.au/about-us/].
Abramomwitz, M. et al, "Immersion Media," Olympus Microscopy Resource Center, 2012, 6 pp. [http://www.olympusmicro.com/primer/anatomy/immersion.html].
Abramomwitz, M., et al, "Field Curvature," Olympus Microscopy Resource Center, 2012, 3 pp. [http://www.olympusmicro.com/primer/anatomy/fieldcurvature.html].

"Age-Related Macular Degeneration (AMD) | National Eye Institute." [Online]. Available: https://www.nei.nih.gov/eyedata/amd#top. [Accessed: Apr. 5, 2016].
Alexandrov, S., et al, "Spatial information transmission beyond a system's diffraction limit using optical spectral encoding of the spatial frequency," Journal of Optics A: Pure and Applied Optics 10, 025304 (2008).
Alexandrov, S.A., et al, "Synthetic Aperture Fourier holographic optical microscopy," Phys. Rev. Lett. 97, 168102 (2006).
Arimoto, H., et al, "Integral three-dimensional imaging with digital reconstruction," Opt. Lett. 26, 157-159 (2001).
Balan, R., et al, "On signal reconstruction without phase, Applied and Computational Harmonic Analysis 20," No. 3 (2006): 345-356.
Balan, R., et al, "Painless reconstruction from magnitudes of frame coefficients," J Fourier Anal Appl 15:488-501 (2009).
Bauschke, H.H., et al, "Phase retrieval, error reduction algorithm, and Fienup variants: a view from convex optimization," J Opt Soc Am A 19:1334-1345 (2002).
Becker, S., et al, "Templates for convex cone problems with applications to sparse signal recovery," Technical report, Department of Statistics, Stanford University, (2010), 48 Pages.
Betti, R., et al, "Observational study on the mitotic rate and other prognostic factors in cutaneous primary melanoma arising from naevi and from melanoma de novo," Journal of the European Academy of Dermatology and Venereology, 2014.
Bian, L., et al, "Fourier ptychographic reconstruction using Wirtinger flow optimization," Opt. Express 23:4856-4866 (2015).
Bian, Z., et al, "Adaptive system correction for robust Fourier ptychographic imaging," Optics express, 2013. 21(26): p. 32400-32410.
BioTek® Brochure: BioTek's Multi-Mode Microplate Reading Techonologies, 2016, 2 pp. [http://www.biotek.com].
Bishara, W., et al, "Holographic pixel super-resolution in portable lensless on-chip microscopy using a fiber-optic array," Lab Chip 11(7), 1276-1279 (2011).
Bishara, W., et al, "Lensfree on-chip microscopy over a wide field-of-view using pixel super-resolution," Opt. Express 18(11), 11181-11191 (2010).
Blum, A., et al, "Clear differences in hand-held dermoscopes," JDDG: Journal der Deutschen Dermatologischen Gesellschaft, 2006, 4(12): p. 1054-1057.
Blum, A., et al, Dermatoskopie von Hauttumoren: Auflichtmikroskopie; Dermoskopie; digitale Bildanalyse; mit 28 Tabellen. 2003: Springer DE, Chapter 4 "Dermatoskopisch sichtbare Strukturen" pp. 15-66.
Born, M., et al, "Principles of Optics: Electromagnetic theory of propagation, interference and diffraction of light" 7th Ed., Cambridge Univ. Press, (1999) pp. 1-31.
Brady, D., et al, "Multiscale gigapixel photography," Nature 486, 386-389 (2012).
Burer, S., et al, "A nonlinear programming algorithm for solving semidefinite programs via low-rank factorization," Math Program, Ser B 95:329-357 (2003).
Burer, S., et al, "Local minima and convergence in low-rank semidefinite programming. Math Program," Ser A 103:427-444 (2005).
Candes, E.J., et al, "Phase retrieval via matrix completion," SIAM J. Imaging Sci. 6:199-225 (2012).
Candes, E.J., et al, "Phase retrieval via Wirtinger flow: theory and algorithms," IEEE Trans. Info. Theory 61:1985-2007 (2015).
Candes, E.J., et al, "PhaseLift: exact and stable signal recovery from magnitude measurements via convex programming.," Comm Pure Appl Math 66:1241-1274 (2013).
Carroll, J., "Adaptive optics retinal imaging: applications for studying retinal degeneration," Arch. Ophthalmol., vol. 126, pp. 857-858, 2008.
Chao, W. et al, "Soft X-ray microscopy at a spatial resolution better than 15 nm," Nature Letters, vol. 435/30, Jun. 2005 pp. 1210-1213.
Chen, T., et al, "Polarization and phase shifting for 3D scanning of translucent objects," Proc. CVPR, (2007).
Chin, L., et al, "Malignant melanoma: genetics and therapeutics in the genomic era," Genes & development, 2006, 20(16): p. 2149-2182.

(56) References Cited

OTHER PUBLICATIONS

Choi, W., et al, "Tomographic phase microscopy," Nature Methods 4(9) (2007), pp. 1-3 Published Online Aug. 12, 2007.

Chung, J., et al, "Counting White Blood Cells from a Blood Smear Using Fourier Ptychographic Microscopy," PLoS One 10(7), e0133489 (2015).

Chung, J., et al, "Wide field-of-view fluorescence image deconvolution with aberration-estimation from Fourier ptychography," Feb. 1, 2016, vol. 7, No. 2, Biomedical Optics Express 352.

Colomb, T., et al, "Automatic procedure for aberration compensation in digital holographic microscopy and applications to specimen shape compensation," Appl. Opt. 45, 851-863 (2006).

De Sa, C., et al, "Global convergence of stochastic gradient descent for some non convex matrix problems," Proc. 32nd Int. Conf. Machine Learning (2015), 10 pp.

Debailleul, M., et al, "High-resolution three-dimensional tomographic diffractive microscopy of transparent inorganic and biological samples," Optic Letters 34 (2008).

Denis, L., et al, "Inline hologram reconstruction with sparsity constraints," Opt. Lett. 34, pp. 3475-3477 (2009).

Di, J., et al, "High resolution digital holographic microscopy with a wide field of view based on a synthetic aperture technique and use of linear CCD scanning," Appl. Opt. 47, pp. 5654-5659 (2008).

Dierolf, M., et al, "Ptychographic coherent diffractive imaging of weakly scattering specimens," New J. Phys. 12, 035017 (2010).

"Doctor Mole—Skin Cancer App," Retrieved Oct. 23, 2015, 1 page. [http://www.doctormole.com].

Dong, S., et al, "FPscope: a field-portable high-resolution microscope using a cellphone lens," Biomed. Opt. Express 5(10), 3305-3310 (2014).

Dong, S., et al, "High-resolution fluorescence imaging via pattern-illuminated Fourier ptychography," Opt. Express 22(17), 20856-20870 (2014).

Dong, S., et al, "Aperture-scanning Fourier ptychography for 3D refocusing and super-resolution macroscopic imaging," pp. 13586-13599 (Jun. 2, 2014).

Eldar, Y.C., et al, "Sparse phase retrieval from short-time Fourier measurements," IEEE Signal Processing Letters 22, No. 5 (2015): 638-642.

Emile, O., et al, "Rotating polarization imaging in turbid media," Optics Letters 21(20), (1996).

Faulkner, H.M.L., and Rodenburg, J.M., "Error tolerance of an iterative phase retrieval algorithm for moveable illumination microscopy," Ultramicroscopy 103(2), 153-164 (2005).

Faulkner, H.M.L., and Rodenburg, J.M., "Movable aperture lensless transmission microscopy: a novel phase retrieval algorithm," Phys. Rev. Lett. 93, 023903 (2004).

Fazel, M., "Matrix rank minimization with applications," PhD Thesis (Stanford University, Palo Alto, CA). (2002).

Feng, P., et al, "Long-working-distance synthetic aperture Fresnel off-axis digital holography," Optics Express 17, pp. 5473-5480 (2009).

Fienup, J. R., "Invariant error metrics for image reconstruction," Appl. Opt. 36(32), 8352-8357 (1997).

Fienup, J. R., "Lensless coherent imaging by phase retrieval with an illumination pattern constraint," Opt. Express 14, 498-508 (2006).

Fienup, J. R., "Phase retrieval algorithms: a comparison," Appl. Opt. 21, 2758-2769 (1982).

Fienup, J. R., "Reconstruction of a complex-valued object from the modulus of its Fourier transform using a support constraint," J. Opt. Soc. Am. A 4, 118-123 (1987).

Fienup, J. R., "Reconstruction of an object from the modulus of its Fourier transform," Opt. Lett. 3, 27-29 (1978).

Gan, X., et al, "Image enhancement through turbid media under a microscope by use of polarization gating methods," JOSA A 16(9), (1999).

Gerke T.D., et al, "Aperiodic volume optics," Nature Photonics (2010), vol. 4, pp. 188-193.

Ghosh, A., et al, "Multiview face capture using polarized spherical gradient illumination," ACM Transactions on Graphics 30(6) (2011).

Godara, P., et al, "Adaptive optics retinal imaging: emerging clinical applications.," Optom. Vis. Sci., vol. 87, No. 12, pp. 930-941, Dec. 2010.

Goodman, J.W., "Introduction to Fourier Optics," Roberts & Company Publication, Third Edition, chapters 1-6, pp. 1-172 (2005).

Goodson, A.G., et al, "Comparative analysis of total body and dermatoscopic photographic monitoring of nevi in similar patient populations at risk for cutaneous melanoma," Dermatologic Surgery, 2010. 36(7): p. 1087-1098.

Granero, L., et al, "Synthetic aperture superresolved microscopy in digital lensless Fourier holography by time and angular multiplexing of the object information," Appl. Opt. 49, pp. 845-857 (2010).

Grant, M., et al, "CVX: Matlab software for disciplined convex programming," version 2.0 beta. http://cvxr.com/cvx, (Sep. 2013), 3 pages.

Greenbaum, A., et al, "Field-portable wide-field microscopy of dense samples using multi-height pixel super resolution based lensfree imaging," Lab Chip 12(7), 1242-1245 (2012).

Greenbaum, A., et al, "Increased space—bandwidth product in pixel super-resolved lensfree on-chip microscopy," Sci. Rep. 3, p. 1717 (2013).

Gruev, V., et al, "Dual-tier thin film polymer polarization imaging sensor," Optics Express, vol. 18, No. 18, 12 pages (2010).

Guizar-Sicairos, M., and Fienup, J.R.,"Phase retrieval with transverse translation diversity: a nonlinear optimization approach," Opt. Express 16, 7264-7278 (2008).

Gunturk, B.K., et al, "Image Restoration: Fundamentals and Advances," vol. 7, Chapter 3, pp. 63-68 (CRC Press, 2012).

Gustafsson, M.G.L., "Surpassing the lateral resolution limit by a factor of two using structured illumination microscopy," J. Microsc. 198, 82-87 (2000).

Gutzler, T., et al, "Coherent aperture-synthesis, wide-field, high-resolution holographic microscopy of biological tissue," Opt. Lett. 35, pp. 1136-1138 (2010).

Haigh, S. J., et al, (2009) "Atomic structure imaging beyond conventional resolution limits in the transmission electron microscope"; Physical Review Letters 103. 126101-1 126101-4.

Han, C., et al, "Wide Field-of-View On-Chip Talbot Fluorescence Microscopy for Longitudinal Cell Culture Monitoring from within the Incubator" Anal. Chem. 85(4), 2356-2360 (2013).

Hillman, T.R., et al, "High-resolution, wide-field object reconstruction with synthetic aperture Fourier holographic optical microscopy," Opt. Express 17, pp. 7873-7892 (2009).

Hofer, H., et al, "Dynamics of the eye's wave aberration," J. Opt. Soc. Am. A, vol. 18, No. 3, p. 497, 2001.

Hofer, H., et al, "Organization of the human trichromatic cone mosaic.," J. Neurosci., vol. 25, No. 42, pp. 9669-9679, Oct. 2005.

Hong, S-H., et al, "Three-dimensional volumetric object reconstruction using computational integral imaging," Opt. Express 12, 483-491 (2004).

Hoppe, W., "Diffraction in inhomogeneous primary wave fields. 1. Principle of phase determination from electron diffraction interference," Acta Crystallogr. A25, 495-501 1969.

Horstmeyer, R., et al, "A phase space model of Fourier ptychographic microscopy," Optics Express, 2014. 22(1): p. 338-358.

Horstmeyer, R., et al, "Digital pathology with fourier ptychography," Comput. Med. Imaging Graphics 42, 38-43 (2015).

Horstmeyer, R., et al, "Overlapped fourier coding for optical aberration removal," Manuscript in preparation, 19 pages (2014).

Horstmeyer, R., et al, "Solving ptychography with a convex relaxation," Physics Optics (2014) 1-8 pages.

Hüe, F., et al, "Wave-front phase retrieval in transmission electron microscopy via ptychography," Phys. Rev. B 82, Dec. 14, 2015 (2010).

Humphry, M., et al, "Ptychographic electron microscopy using high-angle dark-field scattering for sub-nanometre resolution imaging," Nat. Commun. 3, 730 (2012).

IncuCyte® ZOOM System, Brochure, 1-4 pp. (2016) (retrieved Feb. 25, 2016), [http://www.essenbioscience.com/media/uploads/files/8000-0333-E00-IncuCyte_Zoom_brochure.pdf].

Jaganathan, K., et al, "Recovery of sparse 1-D signals from the magnitudes of their Fourier transform," IEEE International Symposium on Information Theory Proceedings (2012): 1473-1477.

(56) References Cited

OTHER PUBLICATIONS

Jaganathan, K., et al, "Phase retrieval with masks using convex optimization," IEEE International Symposium on Information Theory Proceedings (2015): 1655-1659.

Jaganathan, K., et al, "STFT Phase retrieval: uniqueness guarantees and recovery algorithms," arXiv preprint arXiv:1508.02820 (2015).

Joeres, S., et al, "Retinal imaging with adaptive optics scanning laser ophthalmoscopy in unexplained central ring scotoma.," Arch. Ophthalmol., vol. 126, No. 4, pp. 543-547, Apr. 2008.

Jung, J.H., et al, "Microfluidic-integrated laser-controlled micro actuators with on-chip microscopy imaging functionality," Lab Chip 14 (19), Oct. 7, 2014, pp. 3781-3789.

Kay, D. B., et al, "Outer retinal structure in best vitelliform macular dystrophy.," JAMA Ophthalmol., vol. 131, pp. 1207-1215, 2013.

Kim, J., et al, Incubator embedded cell culture imaging system (EmSight) based on Fourier ptychographic microscopy. EmSight manuscript, Optical Society of America, 2015.

Kim, M., et al, "High-speed synthetic aperture microscopy for live cell imaging," Opt. Lett. 36, pp. 148-150 (2011).

Kirkland, A.I., et al, "Multiple beam tilt microscopy for super resolved imaging;" Japanese Society of Electron Microscopy: Journal of Electron Microscopy I: 11-22(1997), vol. 46, No. 1 1997.

Kirkland, A.I., et al, "Super-resolution by aperture synthesis: tilt series reconstruction in CTEM," Ultramicroscopy 57, (1995) 355-374, in final form Oct. 2, 1994; 1995 Elsevier Science B.V. SSDI 0304-3991(94)00191-x.

Kittler, H., et al, "Morphologic changes of pigmented skin lesions: a useful extension of the ABCD rule for dermatoscopy," Journal of the American Academy of Dermatology, 1999. 40(4): p. 558-562.

Kozak, I., "Retinal imaging using adaptive optics technology.," Saudi J. Ophthalmol. Off. J. Saudi Ophthalmol. Soc., vol. 28, No. 2, pp. 117-122, Apr. 2014.

Lauer, V., "New Approach to optical diffraction tomography yielding a vector equation of diffraction tomography and a novel tomography microscope," Journal of Microscopy, vol. 205, Pt 2 Feb. 2002, pp. 165-176, The Royal Microscopical Society 2001.

Lee, K., et al, "Synthetic Fourier transform light scattering," Optics Express 21 (2013).

Levoy, M., et al, "Light field microscopy," ACM Trans. Graphics 25, (2006).

Levoy, M., et al, "Recording and controlling the 4D light field in a microscope using microlens arrays," J. Microsc. 235 (2009).

Li, X., et al, "Sparse signal recovery from quadratic measurements via convex programming," SIAM Journal on Mathematical Analysis 45, No. 5 (2013): 3019-3033.

Lohmann, A. W., et al, "Space—bandwidth product of optical signals and systems," J. Opt. Soc. Am. A 13, pp. 470-473 (1996).

Lue, N., et al, "Live Cell Refractometry Using Hilbert Phase Microscopy and Confocal Reflectance Microscopy," The Journal of Physical Chemistry A, 113, pp. 13327-13330 (2009).

LUXEXCEL® Brochure, LUXEXCEL: 3D Printing Service Description, Retrieved Mar. 7, 2016, 5 pp. [http://www.luxexcel.com].

"Lytro," Retrieved Oct. 23, 2015, 6 pp. [https://www.lytro.com/].

Ma, W., et al, "Rapid Acquisition of Specular and Diffuse Normal Maps from Polarized Spherical Gradient Illumination," University of Southern California, Institute for Creative Technologies, 12 pages (2007).

Mahajan, V. N., "Zernike circle polynomials and optical aberrations of systems with circular pupils," Appl. Opt. 33(34), 8121-8124 (1994).

Maiden, A. M., et al, "A new method of high resolution, quantitative phase scanning microscopy," in: M.T. Postek, D.E. Newbury, S.F. Platek, D.C. Joy (Eds.), SPIE Proceedings of Scanning Microscopy, 7729, 2010.

Maiden, A. M., et al, "An improved ptychographical phase retrieval algorithm for diffractive imaging," Ultramicroscopy 109(10), 1256-1262 (2009).

Maiden, A. M., et al, "Superresolution imaging via ptychography," Journal of the Optical Society of America A. Apr. 2011, vol. 28 No. 4, pp. 604-612.

Maiden, A. M., et al, "Optical ptychography: a practical implementation with useful resolution," Opt. Lett. 35, 2585-2587 (2010).

Marchesini S., "A unified evaluation of iterative projection algorithms for phase retrieval," Rev Sci Instrum 78:011301 (2007).

Marchesini S., et al, "Augmented projections for ptychographic imaging," Inverse Probl 29:115009 (2013).

Marrison, J., et al, "Ptychography—a label free, high-contrast imaging technique for live cells using quantitative phase information," Sci. Rep. 3, 2369 (2013).

Medoff, B.P., et al, "Iterative convolution backprojection algorithms for image reconstruction from limited data," J. Opt. Soc. Am. vol. 73, No. 11, Nov. 1983, pp. 1493-1500.

"Melafind," Retrieved Oct. 23, 2015, 4 pages. [http://www.melafind.com/].

Meyer, R.R., et al, "A method for the determination of the wave aberration function of high-resolution TEM," Ultramicroscopy 99 (2004) 115-123: Elsevier B.V. Doi:10.1016/j.ultramic.2003.11.001.

Miao, J., et al, "High Resolution 3D X-Ray Diffraction Microscopy," Physical Review Letters, Aug. 19, 2002, vol. 89, No. 8, pp. 1-4.

Mico, V., et al, "Synthetic aperture microscopy using off-axis illumination and polarization coding," Optics Communications, pp. 276, 209-217 (2007).

Mico, V., et al, "Synthetic aperture superresolution with multiple off-axis holograms," JOSA A 23, pp. 3162-3170 (2006).

Mir, M. et al, "Optical measurement of cycle-dependent cell growth," Proceedings of the National Academy of Sciences 108, pp. 13124-13129 (2011).

Mir, M., et al, "Blood screening using diffraction phase cytometry," Journal of Biomedical Optics 15, pp. 027016-027014 (2010).

Moreno, I., "Creating a desired lighting pattern with an LED array," 8th International Conference on Solid State Lighting, Proceedings of SPIE, vol. 7058, 2008, 9 pp.

Mrejen, S., et al, "Adaptive optics imaging of cone mosaic abnormalities in acute macular neuroretinopathy.," Ophthalmic Surg. Lasers Imaging Retina, vol. 45, No. 6, pp. 562-569, Jan. 2014.

Nayar, S. K., et al, "Fast separation of direct and global components of a scene using high frequency illumination," ACM Transactions on Graphics 25(3) (2006).

Ng, R., et al, "Light field photography with a hand-held plenoptic camera", Computer Science Technical Report CSTR, 2005. 2(11).

Nomura, H., and Sato, T., "Techniques for measuring aberrations in lenses used in photolithography with printed patterns," Appl. Opt. 38(13), 2800-2807 (1999).

Ohlsson H., et al, "Compressive phase retrieval from squared output measurements via semidefinite programming," arXiv:1111.6323 (2011).

Ou, X., et al, "High numerical aperture Fourier ptychography: principle, implementation and characterization," Opt. Express 23:3472-3491 (2015).

Ou, X., et al, "Quantitative phase imaging via Fourier ptychographic microscopy," Optics Letters, 2013. 38(22): p. 4845-4848.

Ou. X., et al, "Embedded pupil function recovery for Fourier ptychographic microscopy," Optics Express 22 (5), pp. 4960-4972 (2014), with Erratum (2015).

Ou. X., et al, "Embedded pupil function recovery for Fourier ptychographic microscopy," submitted Dec. 26, 2013; 13 pp.

Pacheco, S., et al, "Reflective Fourier Ptychography," J. Biomed. Opt. 21(2), pp. 026010-1-026010-7, (Feb. 18, 2016). [http://biomedicaloptics.spiedigitallibrary.org].

Recht, B., et al, "Guaranteed minimum-rank solutions of linear matrix equations via nuclear norm minimization," SIAM Review 52, No. 3 (2010): 471-501.

Reinhard, E., et al, "High Dynamic Range Imaging: Acquisition, Display, and Image-based Lighting" (Morgan Kaufmann, 2010).

Rodenburg, J. M., et al, "A phase retrieval algorithm for shifting illumination," Appl. Phys. Lett 85, 4795-4797 (2004).

Rodenburg, J. M., et al, "Hard-X-ray lensless imaging of extended objects," Phys. Rev. Lett. 98, 034801 (2007).

Rodenburg, J. M., et al, "The theory of super-resolution electron microscopy via Wigner-distribution deconvolution," Phil. Trans. R. Soc. Lond. A 339, 521-553 (1992).

(56) References Cited

OTHER PUBLICATIONS

Rodenburg, J., "Ptychography and related diffractive imaging methods," Adv. Imaging Electron Phys.150, 87-184 (2008).
Rossi, E.A., et al, "In vivo imaging of retinal pigment epithelium cells in age related macular degeneration.," Biomed. Opt. Express, vol. 4, No. 11, pp. 2527-2539, Jan. 2013.
Rowe, M., et al, "Polarization-difference imaging: a biologically inspired technique for observation through scattering media," Optics Letters, vol. 20, No. 6, 3 pages (1995).
Schechner, Y., "Multiplexing for Optimal Lighting," IEEE Transactions on Pattern Analysis and Machine Intelligence, vol. 29, No. 8, 1339-1354 (2007).
Schnars, U., et al, "Digital recording and numerical reconstruction of holograms," Measurement Science and Technology, 13, R85 (2002).
Schwarz, C., et al, "Imaging interferometric microscopy," Optics letters 28, pp. 1424-1426 (2003).
Shechner, Y., et al, "Polarization-based vision through haze," Applied Optics 42(3), (2003).
Shechtman, Y., et al, "Sparsity based sub-wavelength imaging with partially incoherent light via quadratic compressed sensing," Opt Express 19:14807-14822 (2011).
Siegel, R., et al, "Cancer statistics 2013," CA: a cancer journal for clinicians, 2013. 63(1): p. 11-30.
Stoecker, W., et al, "Diagnostic Inaccuracy of Smartphone Applications for Melanoma Detection: Representative Lesion Sets and the Role for Adjunctive Technologies," JAMA Dermatology, 2013. 149(7): p. 884.
Sun, D., et al, "Estimating a signal from a magnitude spectrogram via convex optimization," arXiv:1209.2076 (2012).
Sun, J., et al, "Coded multi-angular illumination for Fourier ptychography based on Hadamard codes," 5 pages (2015).
Tam, K., et al, "Tomographical imaging with limited-angle input," J. Opt. Soc. Am. 21 (1981).
Thibault, P. et al, "Probe retrieval in ptychographic coherent diffractive imaging," Ultramicroscopy 109(4), 338-343 (2009).
Thibault, P., et al, "High-resolution scanning X-ray diffraction microscopy," Science 321, 2008, pp. 379-382.
Thomas, L., et al, "Semiological value of ABCDE criteria in the diagnosis of cutaneous pigmented tumors," Dermatology, 1998. 197(1): p. 11-17.
Tian, L., et al, "Multiplexed Coded Illumination for Fourier Ptychography with an LED Array Microscope," Optical Society of America, 14 pages (2014).
Tippie, A.E., et al, "High-resolution synthetic-aperture digital holography with digital phase and pupil correction," Opt. Express 19, pp. 12027-12038 (2011).
Turpin, T., et al, "Theory of the synthetic aperture microscope," pp. 230-240 (1995).
Tyson, R., "Principles of Adaptive Optics" (CRC Press, 2010).
Vulovic, M., et al, "When to use the projection assumption and the weak-phase object approximation in phase contrast cryo-EM," Ultramicroscopy 136 (2014) 61-66.
Waldspurger, I., et al, "Phase recovery, maxcut and complex semidefinite programming," Mathematical Programming 149, No. 1-2 (2015): 47-81.
Wang, Q., et al, "Adaptive Optics Microperimetry and OCT Images Show Preserved Function and Recovery of Cone Visibility in Macular Telangiectasia Type 2 Retinal Lesions," Invest. Ophthalmol. Vis. Sci., vol. 56, pp. 778-786 (2015).
Wang, Z., et al, "Tissue refractive index as marker of disease," Journal of Biomedical Optics 16, 116017-116017 (2011).
Watanabe, M., et al, "Telecentric optics for focus analysis," IEEE trans. pattern. anal. mach. intell., 19 1360-1365 (1997).
Wesner, J., et al, "Reconstructing the pupil function of microscope objectives from the intensity PSF," in Current Developments in Lens Design and Optical Engineering III, R. E. Fischer, W. J. Smith, and R. B. Johnson, eds., Proc. SPIE 4767, 32-43 (2002).

Williams, A., et al, "Fourier ptychographic microscopy for filtration-based circulating tumor cell enumeration and analysis," J. Biomed. Opt. 19(6), 066007 (2014).
Wolf, J., et al, "Diagnostic Inaccuracy of Smartphone Applications for Melanoma Detection," JAMA Dermatology, 2013, 149(7): p. 885-885.
Wu, J., et al, "Focal plane tuning in wide-field-of-view microscope with Talbot pattern illumination," Opt. Lett. 36, 2179-2181 (2011).
Wu, J., et al, "Wide field-of-view microscope based on holographic focus grid illumination," Opt. Lett. 35, 2188-2190 (2010).
Xu, W., et al, "Digital in-line holography for biological applications," Proc. Natl Acad. Sci. USA 98, pp. 11301-11305 (2001).
Yuan, C., et al, "Angular multiplexing in pulsed digital holography for aperture synthesis," Optics Letters 33, pp. 2356-2358 (2008).
Zeiss, C., "Microscopy, Cells Need the Perfect Climate, System Solutions for Live Cell Imaging under Physiological Conditions," printed Feb. 2008, 1-42 pgs.
Zhang, Y., et al, "Self-learning based fourier ptychographic microscopy," Optics Express, 16pgs (2015).
Zhang, Y., et al, "Photoreceptor Perturbation Around Subretinal Drusenoid Deposits as Revealed by Adaptive Optics Scanning Laser Ophthalmoscopy," Am. J. Ophthalmol., vol. 158, No. 3, pp. 584-596, 2014.
Zheng, G., et al, "Characterization of spatially varying aberrations for wide field-of-view microscopy," Opt. Express 21, 15131-15143 (2013).
Zheng, G., et al, "Microscopy refocusing and dark-field imaging by using a simple LED array," Opt. Lett. 36, 3987-3989 (2011).
Zheng, G., et al, "0.5 gigapixel microscopy using a flatbed scanner," Biomed. Opt. Express 5, 1-8 (2014).
Zheng, G., et al, "Sub-pixel resolving optofluidic microscope for on-chip cell imaging," Lab Chip 10, pp. 3125-3129 (2010).
Zheng, G. "The ePetri dish, an on-chip cell imaging platform based on subpixel perspective sweeping microscopy (SPSM)," Proc. Natl. Acad. Sci. USA 108, pp. 16889-16894 (2011).
Zheng, G., et al, "Wide-field, high-resolution Fourier ptychographic microscopy," Nature Photonics, vol. 7, pp. 739-745, Published Online Jul. 28, 2013 at www.nature.com/naturephotonics.
Chung, J., et al, "Wide-field Fourier ptychographic microscopy using laser illumination source," Optical Society of America, 13 pgs., Mar. 23, 2016.
Guo, K., et al, "Optimization of sampling pattern and the design of Fourier ptychographic illuminator," Optical Society of America; Optics Express , vol. 23, No. 5, pp. 6171-6180 (2015).
Phillips, Z., et al, "Multi-Contrast Imaging and Digital Refocusing on a Mobile Microscope with a Domed LED Array," PLoS One, 10 (5), pp. 1-13 (2015).
U.S. Office Action dated Jul. 14, 2016 in U.S. Appl. No. 15/007,196.
U.S. Notice of Allowance dated Aug. 23, 2016 in U.S. Appl. No. 14/466,481.
U.S. Office Action dated Aug. 16, 2016 in U.S. Appl. No. 14/065,280.
U.S. Office Action dated Sep. 16, 2016 I U.S. Appl. No. 14/065,305.
U.S. Notice of Allowance dated Nov. 2, 2016 in U.S. Appl. No. 14/572,493.
U.S. Office Action dated Nov. 22, 2016 in U.S. Appl. No. 15/003,559.
U.S. Supplemental Notice of Allowance dated Dec. 12, 2016 in U.S. Appl. No. 14/572,493.
International Search Report and Written Opinion dated Jun. 27, 2016 issued in PCT/US2016/022116.
International Search Report and Written Opinion dated Jun. 30, 2016 issued in PCT/US2016/014343.
International Search Report and Wrtitten Opinion dated Sep. 5, 2016 issued in PCT/US2016/033638.
Chinese Office Action [Description in English] dated Jul. 11, 2016 issued in Application No. CN 201380068831.6.
Dierolf, M., et al, "Ptychographic X-ray computed tomography at the nanoscale," Nature, vol. 467, pp. 436-439, (2010).
Horstmeyer, R., et al, "Standardizing the resolution claims for coherent microscopy," Nature Photonics, vol. 10, pp. 68-71, Feb. 2016.
Horstmeyer, R., et al, "Solving ptychography with a convex relaxation," New Journal Of Physics, vol. 17 (2015) 1-14 pages.

(56) References Cited

OTHER PUBLICATIONS

Preliminary Amendment dated Mar. 17, 2014 filed in U.S. Appl. No. 14/065,280.
Preliminary Amendment dated Apr. 25, 2016 filed in U.S. Appl. No. 14/710,947.
Preliminary Amendment dated Jun. 13, 2018 filed in U.S. Appl. No. 15/820,295.
U.S. Final Office Action dated Apr. 3, 2017 in U.S. Appl. No. 14/065,280.
U.S. Office Action dated Jan. 25, 2018 in U.S. Appl. No. 14/065,280.
U.S. Notice of Allowance dated Jan. 13, 2017 in U.S. Appl. No. 14/065,305.
U.S. Notice of Allowance dated Jun. 9, 2017 in U.S. Appl. No. 14/065,305.
Notice of Allowance dated Dec. 4, 2017 in U.S. Appl. No. 14/065,305.
U.S. Notice of Allowance dated Aug. 16, 2017 in U.S. Appl. No. 15/209,604.
Notice of Allowance dated Jan. 26, 2018 in U.S. Appl. No. 15/209,604.
U.S. Notice of Allowance dated Jun. 9, 2017 in U.S. Appl. No. 15/206,859.
U.S. Notice of Allowance dated Sep. 1, 2017 in U.S. Appl. No. 15/206,859.
Notice of Allowance dated Jan. 23, 2018 in U.S. Appl. No. 15/206,859.
U.S. Notice of Allowance dated Mar. 8, 2017 in U.S. Appl. No. 14/572,493.
U.S. Notice of Allowance dated Mar. 31, 2017 in U.S. Appl. No. 14/572,493.
U.S. Notice of Allowance dated Jun. 20, 2017 in U.S. Appl. No. 14/572,493.
Notice of Allowance dated Oct. 11, 2017 in U.S. Appl. No. 14/572,493.
U.S. Office Action dated Mar. 13, 2017 in U.S. Appl. No. 14/658,019.
U.S. Final Office Action dated Jan. 17, 2018 in U.S. Appl. No. 14/658,019.
U.S. Office Action dated Mar. 24, 2017 in U.S. Appl. No. 14/710,947.
U.S Final Office Action dated Dec. 28, 2017 in U.S. Appl. No. 14/710,947.
U.S. Notice of Allowance dated Jul. 25, 2018 in U.S. Appl. No. 14/710,947.
U.S. Office Action dated Feb. 21, 2017 in U.S. Appl. No. 14/960,252.
U.S. Final Office Action dated Dec. 14, 2017 in U.S. Appl. No. 14/960,252.
U.S. Final Office Action dated Jan. 23, 2017 in U.S. Appl. No. 15/007,196.
U.S. Notice of Allowance dated Mar. 22, 2017 in U.S. Appl. No. 15/007,196.
U.S. Notice of Allowance dated Jun. 9, 2017 in U.S. Appl. No. 15/007,196.
U.S. Office Action dated Aug. 31, 2017 in U.S. Appl. No. 15/636,494.
U.S. Notice of Allowance dated Sep. 20, 2017 in U.S. Appl. No. 15/007,196.
U.S. Notice of Allowance dated Jun. 27, 2018 in U.S. Appl. No. 15/636,494.
U.S. Office Action dated Nov. 30, 2017 in U.S. Appl. No. 15/007,159.
U.S. Notice of Allowance dated Jul. 16, 2018 in U.S. Appl. No. 15/007,159.
U.S. Office Action dated Sep. 7, 2018 in U.S. Appl. No. 14/979,154.
U.S. Final Office Action dated Jul. 27, 2017 in U.S. Appl. No. 15/003,559.
Office Action dated Apr. 4, 2018 issued in U.S. Appl. No. 15/003,559.
Office Action dated Nov. 3, 2017 in U.S. Appl. No. 15/068,389.
Office Action Interview Summary dated May 3, 2018 in U.S. Appl. No. 15/068,389.
Final Office Action dated Jun. 6, 2018 issued in U.S. Appl. No. 15/068,389.
Office Action dated May 19, 2017 in U.S. Appl. No. 15/081,659.
Notice of Allowance dated Oct. 20, 2017 in U.S. Appl. No. 15/081,659.
Notice of Allowance dated Feb. 9, 2018 in U.S. Appl. No. 15/081,659.
Office Action dated Apr. 13, 2018 issued in U.S. Appl. No. 15/160,941.
Japanese First Office Action dated Jul. 31, 2018 issued in Application No. JP 2016-531919.
European Extended Search Report dated Jun. 6, 2018 issued in Application No. 15865492.1.
Extended European Search Report dated Aug. 8, 2018 issued in Application No. EP 16744002.3.
Chinese First Office Action dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Application No. 14832857.8.
Chinese Second Office Action [Description in English] dated Jan. 22, 2017 issued in Application No. CN201380068831.6.
International Preliminary Report on Patentability dated Jun. 15, 2017 issued in Application No. PCT/US2015/064126.
European Office Action dated May 16, 2017 issued in European Patent Application No. 13851670.3.
International Preliminary Report on Patentability dated Jul. 6, 2017 issued in Application No. PCT/US2015/067498.
Extended European Search Report dated Jul. 3, 2018 issued in Application No. EP 15874344.3.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
International Preliminary Report on Patentability dated Aug. 10, 2017 issued in Application No. PCT/US2016/015002.
Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Chinese Second Office Action dated Jul. 3, 2018 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.
Japanese Office Action dated Oct. 17, 2017 issued in Application No. 2015-539884.
Chinese Second Office Action dated Oct. 26, 2017 issued in CN 201480057911.6.
Chinese Third Office Action dated Jul. 13, 2018 issued in CN 201480057911.6.
International Preliminary Report on Patentability dated Nov. 30, 2017 issued in PCT/US2016/033638.
Australian Examination Report 1/Office Action dated Jan. 18, 2018 issued in AU 2014308673.
Chinese First Office Action dated Feb. 24, 2018 issued in CN 201680003937.1.
Abrahamsson, S., et al., "Fast multicolor 3D imaging using aberration-corrected mulitfocus microscopy," Brief Communications: Nature Methods, vol. 10, No. 1, Jan. 2013, pp. 60-65. <doi:10.1038/nmeth.2277>.
Bian, L., et al, "Fourier ptychographic reconstruction using Poisson maximum likelihood and truncated Wirtinger gradient," Nature Publishing Group; Scientific Reports, vol. 6, No. 27384, Jun. 10, 2016, pp. 1-10. <doi: 10.1038/srep27384>.
Bunk, O., et al, "Influence of the overlap parameter on the convergence of the ptychographical iterative engine," Ultramicroscopy, vol. 108, (2008), pp. 481-487. <doi:10.1016/j.ultramic.2007.08.003>.
Chai, A., et al, "Array imaging using intensity-only measurements," IOP Publishing: Inverse Problems, vol. 27, No. 1, Jan. 2011, pp. 1-16. <doi:10.1088/0266-5611/27/1/015005>.
Holloway, J., et al. "SAVI: Synthetic apertures for long-range, subdiffraction-limited visible imaging using Fourier ptychography," Science Advances | Research Article, vol. 3, No. 4, Apr. 14, 2017, pp. 1-11. <doi:10.1126/sciadv.1602564> [retrieved on Nov. 28, 2017] <URL:http://advances.sciencemag.org/>.
Horstmeyer, R., et al, "Diffraction tomography with Fourier ptychography," Optica, Optical Society of America, vol. 3, No. 8, Aug. 2016, pp. 827-835. <doi:10.1364/OPTICA.3.000827>.

(56) References Cited

OTHER PUBLICATIONS

Jacques, et al., "Imaging Superficial Tissues With Polarized Light," Lasers in Surgery and Medicine, vol. 26, No. 2, Apr. 25, 2000, pp. 119-129.
Jensen, et al. "Types of imaging, Part 2: An Overview of Fluorescence Microscopy." The Anatomical Record, vol. 295, No. 10, Oct. 1, 2012, pp. 1621-1627.
Kawata, S. et al, "Optical microscope tomography. I. Support constraint," Journal Optical Society America A, vol. 4, No. 1, Jan. 1987, pp. 292-297. <doi:10.1364/JOSSA.4.000292>.
Kim, M., et al, "High-speed synthetic aperture microscopy for live cell imaging," Optics Letters, vol. 36, No. 2, Jan. 15, 2011, pp. 148-150. <doi:10.1364/OL.36.000148>.
Kner, P., "Phase diversity for three-dimensional imaging," Journal of the Optical Society of America A, vol. 30, No. 10, Oct. 1, 2013, pp. 1980-1987. <doi:10.1364/JOSSA.30.001980>.
Lu, H., et al, "Quantitative phase imaging and complex field reconstruction by pupil modulation differential phase contrast," Optics Express, vol. 24, No. 22, Oct. 31, 2016, pp. 25345-25361. <doi:10.1364/OE.24.025345>.
Ou, X., et al, "Aperture scanning Fourier ptychographic microscopy," Biomedical Optics Express, vol. 7, No. 8, Aug. 1, 2016, pp. 3140-3150. <doi:10.1364/BOE.7.003140>.
Sarder, et al. "Deconvolution Methods for 3-D Fluorescence Microscopy Images," IEEE Signal Processing Magazine, vol. 23, No. 3, May 2006, pp. 32-45.
Sankaranarayanan, Aswin C., et al, "CS-MUVI: Video Compressive Sensing for Spatial-Multiplexing Cameras," Proceedings of the IEEE International Conference Computational Photography (ICCP), Apr. 2012, pp. 11. <doi:10.1109/ICCPhot.2012.6215212>.
Tian, L., et al, "3D differential phase-contrast microscopy with computational illumination using an LED array," Optics Letters, vol. 39, No. 5, Mar. 1, 2014, pp. 1326-1329. <doi:10.1364/OL39.001326>.
Tian, L., et al, "Computational illumination for high-speed in vitro Fourier ptychographic microscopy," Optica: Research Article, vol. 2, No. 10, Oct. 14, 2015, pp. 904-911. <doi:10.1364/OPTICA.2.000904>.
Wills, S., "Synthetic Apertures for the Optical Domain," Optics & Photonics News Article [webpage], The Optical Society (OSA), Apr. 18, 2017, pp. 2. <URL:https://www.osa-opn.org/home/newsroom/2017/april/synthetic_apertures_for_the_optical_domain/>.
Wu, J., et al, "Harmonically matched grating-based full-field quantitative high-resolution phase microscope for observing dynamics of transparent biological samples," Optics Express, vol. 15, No. 26, Dec. 24, 2007, pp. 18141-18155. <doi:10.1364/OE.15.018141>.
Wu, J., et al, "Paired-angle-rotation scanning optical coherence tomography forward-imaging probe," Optics Letters, vol. 31, No. 9, May 1, 2006, pp. 1265-1267. <doi:10.1364/OL.31.001265>.
Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Zheng, G., "Fourier Ptychographic Imaging: A MATLAB tutorial," IOP Concise Physics, Morgan & Claypool Publication, San Rafael, CA., May 2016, pp. 96. <ISBN: 978-1-6817-4272-4 (ebook)> <doi: 10.1088/978-1-6817-4273-1>.
Zheng, G., et al, "Wide-field, high-resolution Fourier ptychographic microscopy," Nature Photonics, vol. 7, Sep. 2013, Published Online Jul. 28, 2013, pp. 739-746. <doi:10.1038/NPHOTON.2013.187>.
Preliminary Amendment filed Jul. 11, 2018 in U.S. Appl. No. 15/959,050.
Preliminary Amendment filed Jul. 23, 2018 in U.S. Appl. No. 15/963,966.
U.S. Appl. No. 15/963,966, filed Apr. 26, 2018, Ou et al.
U.S. Appl. No. 15/959,050, filed Apr. 20, 2018, Horstmeyer et al.
Notice of Allowance dated Sep. 17, 2018 in U.S. Appl. No. 15/820,295.
U.S. Office Action dated Oct. 4, 2018 in U.S. Appl. No. 14/658,019.
U.S. Notice of Allowance dated Oct. 5, 2018 in U.S. Appl. No. 15/636,494.
Chinese Office Action [Description in English] dated May 31, 2016 issued in Application No. CN 201380068831.6.
European Extended Search Report dated Aug. 14, 2018 issued in EP 16744003.1.
Extended European Search Report dated Sep. 12, 2018 issued in Application No. EP 16740769.1.
Godden, T.M. et al., "Ptychographic microscope for three-dimensional imaging," Optics Express, vol. 22, No. 10, May 19, 2014, pp. 12513-12523.
Hoppe, W., "Diffraction in inhomogeneous primary wave fields. I. Principle of phase determination from electron diffraction interference." Acta Crystallographica Section a-Crystal Physics Diffraction Theoretical and General Crystallography, A25, Jan. 1, 1969, pp. 495-501. (English Machine Translation Incl.).
Maiden, A.M., et al., "Ptychographic transmission microscopy in three dimensions using a multi-slice approach," Journal of the Optical Society of America A., vol. 29, No. 8, Aug. 1, 2012, pp. 1606-1614.
Reinhard, E., et al, "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.
U.S. Appl. No. 16/162,271, filed Oct. 16, 2018, Kim et al.
U.S. Final Office Action dated Nov. 29, 2018 in U.S. Appl. No. 14/065,280.
U.S. Office Action dated Dec. 26, 2018 in U.S. Appl. No. 15/963,966.
U.S. Office Action dated Dec. 26, 2018 in U.S. Appl. No. 15/959,050.
U.S. Office Action dated Dec. 13, 2018 in U.S. Appl. No. 14/960,252
U.S. Final Office Action dated Dec. 10, 2018 issued in U.S. Appl. No. 15/003,559.
Extended European Search Report dated Oct. 25, 2018 issued in Application No. EP 16765505.9.
U.S. Appl. No. 16/171,270, filed Oct. 25, 2018, Horstmeyer et al.
U.S. Appl. No. 16/179,688, filed Nov. 2, 2018, Chan et al.
U.S. Appl. No. 16/242,934, filed Jan. 8, 2019, Kim et al.

\* cited by examiner

LASER-BASED FOURIER PTYCHOGRAPHIC IMAGING SYSTEMS AND METHODS

CROSS-REFERENCE TO RELATED APPLICATION

This application claims priority to U.S. Provisional Patent Application No. 62/165,084, titled "Laser Based Fourier Ptychographic Microscopy" and filed on May 21, 2015, which is hereby incorporated by reference in its entirety and for all purposes.

FEDERALLY SPONSORED RESEARCH OR DEVELOPMENT

This invention was made with government support under Grant No. OD007307 and AI096226 awarded by the National Institutes of Health. The government has certain rights in the invention.

FIELD

Certain embodiments described herein are generally related to digital imaging techniques, more specifically, in high-resolution imaging for microscopy and photography in applications such as, for example, pathology, haematology, and semiconductor wafer inspection.

BACKGROUND

Imaging lenses ranging from microscope objectives to satellite-based cameras are physically limited in the total number of features they can resolve. These limitations are a function of the point-spread function size of the imaging system and the inherent aberrations across its image plane field of view. Referred to as the space-bandwidth product, the physical limitation scales with the dimensions of the lens but is usually on the order of 10 megapixels regardless of the magnification factor or numerical aperture (NA). While conventional imaging systems may be able to resolve up to 10 megapixels, there is typically a tradeoff between point-spread function and field of view. For example, certain conventional microscope objectives may offer a sharp point-spread function across a narrow field of view, while others imaging systems with wide-angle lenses can offer a wide field of view at the expense of a blurry point-spread function.

Traditionally, the resolution of an image sensor, such as in a digital camera, determines the fidelity of visual features in the resultant images captured by the image sensor. However, the resolution of any image sensor is fundamentally limited by geometric aberrations in the lens or lenses used to focus light onto the image sensor. This is because the number of resolvable points for a lens, referred to as the SBP, is fundamentally limited by geometrical aberrations. While CMOS and CCD technologies have been demonstrated having image sensors with pixels in the 1 micron (µm) range, it remains a challenge to design and manufacture lenses which have the resolving power to match the resolution of such image sensors.

Certain interferometric synthetic aperture techniques try to increase spatial-bandwidth product. Most of these interferometric synthetic aperture techniques include setups that record both intensity and phase information using interferometric holography such as off-line holography and phase-shifting holography. Interferometric holography has its limitations. For example, interferometric holography recordings typically use highly coherent light sources. As such, the constructed images typically suffer from coherent noise sources such as speckle noise, fixed pattern noise (induced by diffraction from dust particles and other optical imperfections in the beam path), and multiple interferences between different optical interfaces. Thus the image quality is typically worse than from a conventional microscope. On the other hand, using off-axis holography sacrifices spatial-bandwidth product (i.e., reduces total pixel number) of the image sensor. In addition, interferometric imaging techniques may be subject to uncontrollable phase fluctuations between different measurements. Hence, accurate a priori knowledge of the sample location may be needed to set a reference point in the image recovery process. Another limitation is that many of these interferometric imaging systems require mechanical scanning to rotate the sample and thus precise optical alignments, mechanical control at a sub-micron level, and associated maintenances are required by these systems. In terms of spatial-bandwidth product, these interferometric imaging systems may present little to no advantage as compared with a conventional microscope. Previous lensless microscopy such as in-line holography and contact-imaging microscopy also present drawbacks. For example, conventional in-line holography does not work well with contiguous samples and contact-imaging microscopy requires a sample to be in close proximity to the sensor.

A high spatial-bandwidth product is very desirable in imaging applications such as microscopy for biomedical imaging such as used in pathology, haematology, phytotomy, immunohistochemistry, and neuroanatomy. For example, there is a strong need in biomedicine and neuroscience to image large numbers of histology slides for evaluation.

SUMMARY

Certain embodiments pertain to laser-based Fourier ptychographic (LFP) imaging systems and their components. For example, some embodiments relate to LFP systems comprising an angle direction device, an optical system comprising a collection element and a focusing element, and a light detector(s). The angle direction device is configured or configurable to direct laser light from a laser light source(s) to a sample plane generally at a specimen surface. The laser light is directed at a sequence of illumination angles at different sample times. The collection element is configured to receive light issuing from a specimen when it is located on the specimen surface. The sequence of illumination angles and numerical aperture of the collection element correspond to overlapping regions in a Fourier domain. The light detector is configured or configurable to receive light focused by the focusing element of the optical system and to acquire a plurality of raw intensity images of the specimen when it is located on the specimen surface and illuminated. Each raw intensity image acquired by the light detector(s) corresponds to a different illumination angle of the sequence of illumination angles. The LFP systems may also include a processor configured or configurable to execute instructions for iteratively updating overlapping regions in the Fourier domain with the plurality of intensity images acquired by the light detector to generate a high resolution image of the specimen. In some cases, the processor is also configured or configurable to execute instructions for filtering out low spatial frequency artifacts associated laser light by using a differential phase contrast deconvolution procedure.

Certain embodiments pertain to angle direction devices configured or configurable to direct laser light from a laser light source(s) to a sample plane generally at a specimen surface of an LFP system.

In one embodiment, the angle direction device comprises a plurality of fixed mirrors and one or more rotatable mirrors. Each fixed mirror is oriented to reflect laser light at one of the plurality of illumination angles to the specimen surface. The one or more rotatable mirrors are configured or configurable to reflect laser light from the laser light source sequentially to different fixed mirrors of the plurality of fixed mirrors at different sampling times. The fixed mirrors are oriented to reflect laser light received from the one or more rotatable mirrors to the specimen surface at the sequence of illumination angles.

In another embodiment, the angle direction device comprises a plurality of optical fibers and one or more optical switches. Each of the plurality of optical fibers has a first and second end portion. The one or more optical switches are in optical communication with a laser light source. The one or more optical switches are configured or configurable to switch at different sampling times to direct laser light from the laser light source to the first end portion of different optical fibers of the plurality of optical fibers when the laser light source is activated. The optical pathways are configured so that each second end portion directs laser light to one of the sequence of illumination angles when the one or more optical switches is switched to the corresponding optical fiber and the laser light source is activated.

In another embodiment, the angle direction device comprises a movable stage (e.g., X-Y stage) and an optical fiber coupled to the movable stage and optically coupled at one end to the laser light source. The movable stage is configured or configurable to translate and/or rotate the optical fiber to direct laser light from the other end of the optical fiber to illuminate the specimen surface at the plurality of illumination angles at the different sampling times.

In another embodiment, the angle direction device comprises one or more rotatable mirrors and a lens system. The one or more rotatable mirrors are configured or configurable to direct the laser light from the laser light source to the specimen surface through a lens system, the lens system configured such that rotation of the one or more rotatable mirrors causes the laser light to illuminate the specimen at the sequence of illumination angles.

In certain embodiments, the angle direction device comprises a surface and a plurality of fixed mirrors coupled to the surface, each fixed mirror oriented to receive laser light and reflect the laser light to one of the plurality of illumination angles.

Certain embodiments pertain to laser-based Fourier ptychographic imaging methods employing at least one laser light source. The methods comprise directing laser light from a laser light source to a specimen surface located at about a sample plane using an angle direction device at a sequence of illumination angles. The methods further comprise receiving light, at a light detector, issuing from a sample when the sample is located on the specimen surface, the light received from an optical system. The methods further comprise acquiring a plurality of intensity images based on light received at the light detector, wherein each intensity image corresponds to one of the illumination angles. The methods further comprise constructing a higher resolution image by simultaneously updating a pupil function and a sample spectrum, wherein the sample spectrum is updated in overlapping regions with Fourier transformed intensity images, wherein each of the overlapping regions corresponds to one of the plurality of illumination angles.

These and other features are described in more detail below with reference to the associated drawings.

DETAILED DESCRIPTION

Figure 1:
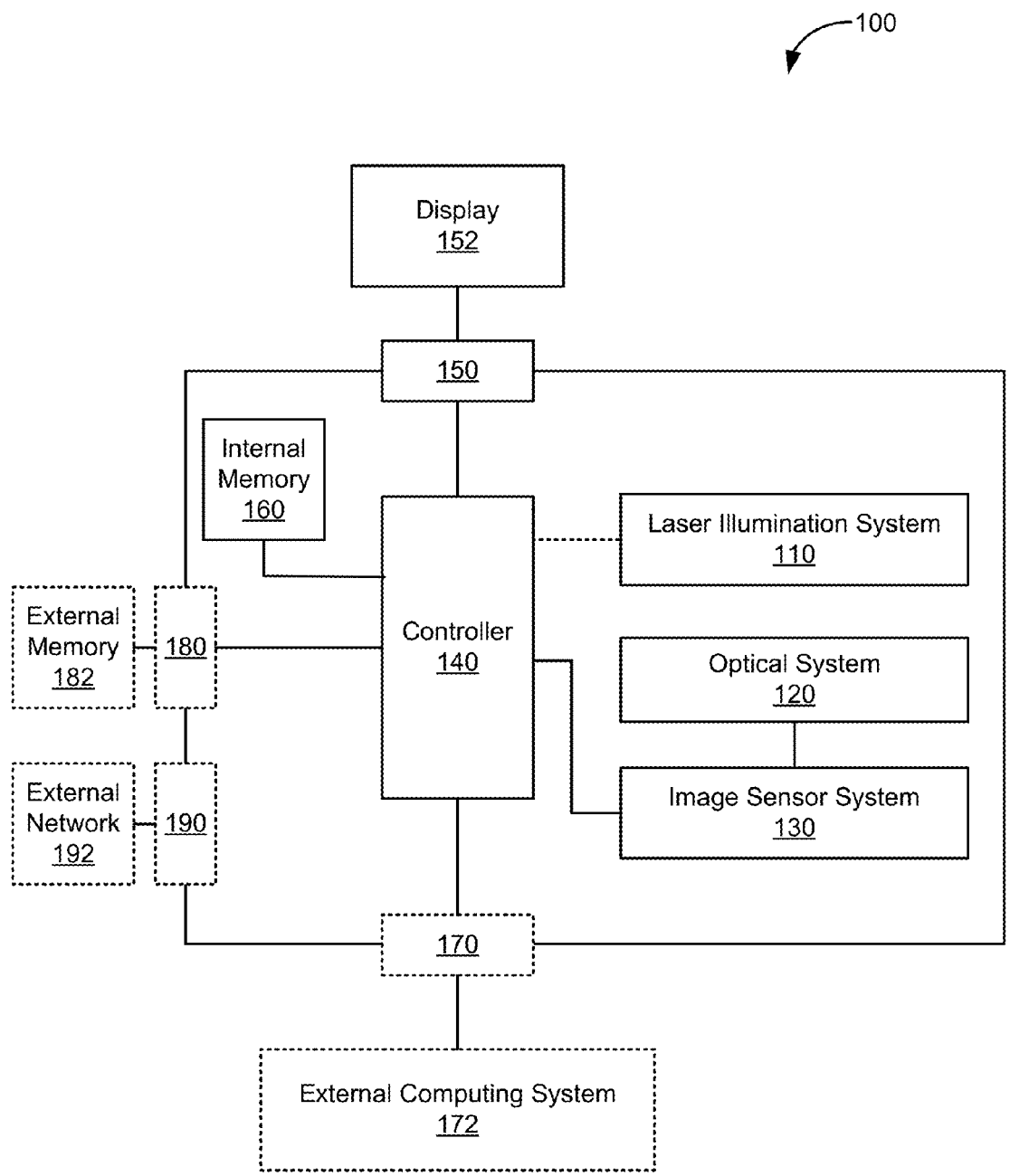
FIG. 1 shows a simplified block diagram of a laser-based Fourier ptychographic (LFP) imaging system, in accordance with some implementations.

Embodiments of the present invention will be described below with reference to the accompanying drawings. The following description is directed to certain implementations for the purposes of describing various aspects of this disclosure. However, a person having ordinary skill in the art will readily recognize that the teachings herein can be applied in a multitude of different ways. Thus, the teachings are not intended to be limited to the implementations depicted solely in the Figures, but instead have wide applicability as will be readily apparent to one having ordinary skill in the art.

I. Introduction

Fourier ptychography imaging techniques generally involve synthesizing an image with a higher bandwidth using multiple low-bandwidth images captured at different spatial frequency regions. Fourier ptychography techniques provide resolution enhancement that can be implemented with an optical system to achieve resolution construction beyond the physical capabilities of the optical system alone. In certain cases, Fourier ptychography imaging involves the acquisition of multiple raw intensity images of a sample where each image is acquired using light at a different illumination angle than the others (variable illumination).

An imaging system that implements Fourier ptychography imaging techniques using a microscope optical system is collectively referred to as an FPM. Some examples of existing FPMs that use light-emitting diode (LED) illumination can be found in G. Zheng, R. Horstmeyer and C. Yang, "Wide-field, high-resolution Fourier ptychographic microscopy," Nature Photonics, 2013, X. Ou, R. Horstmeyer, C. Yang and G. Zheng, "Quantitative phase imaging via Fourier ptychographic microscopy," Optics Letters, 2013, X. Ou, R. Horstmeyer, G. Zheng and C. Yang, "High numerical aperture Fourier ptychography: principle, implementation and characterization," Optics Express, 2015, "A phase space model of Fourier ptychographic microscopy," Opt. Express 22(1), 338-358 (2014), X. Ou, G. Zheng, and C. Yang, "Embedded pupil function recovery for Fourier ptychographic microscopy," Opt. Express 22(5), 4960-4972 (2014), X. Ou, R. Horstmeyer, G. Zheng, and C. Yang, "Counting White Blood Cells from a Blood Smear Using Fourier Ptychographic Microscopy," PLoS One 10(7), e0133489 (2015), A. Williams, J. Chung, X. Ou, G. Zheng, S. Rawal, Z. Ao, R. Datar, C. Yang, and R. Cote, "Fourier ptychographic microscopy for filtration-based circulating tumor cell enumeration and analysis," J. Biomed. Opt. 19(6), 066007 (2014), and R. Horstmeyer, X. Ou, G. Zheng, P. Willems, and C. Yang, "Digital pathology with Fourier ptychography," Comput. Med. Imaging Graphics 42, 38-43 (2015), all of which are hereby incorporated by reference for the discussion regarding FPMs.

As introduced above, existing implementations of FPMs typically used an array of average consumable light-emitting diodes (LEDs) to provide angularly varying illumination. The time need to acquire the raw intensity images and generate a high resolution image with the existing LED-based FPMs was typically relatively slow since LEDs provide low intensity illumination that required lengthy exposure times. Although high power LEDs could be used, they require cooling systems that made it difficult to design a compact system.

Various aspects described here relate generally to Laser-based Fourier ptychographic (LFP) imaging systems, devices, and methods that use a guided laser beam as illumination. In these aspects, the LFP imaging system includes an angle direction device to direct laser light illumination at different illumination angles. For example, certain LFP imaging systems discussed herein are configured to enable high resolution imaging of a sample (also referred to herein as a "specimen") on a specimen surface at a sample plane, using an angle direction device configured or configurable to direct laser light sequentially at different illumination angles to the sample plane. The use of a laser light sometimes present speckles during image acquisition due to reflections between glass surfaces in the system. If not mitigated, these speckles would appear as slowly varying background fluctuations in the final reconstructed image. The LFP imaging method is adapted to mitigate artifacts from any speckles.

Since LFP imaging systems use laser light, they have several advantages as compared to existing Fourier ptychography imaging systems that use average consumable LED array to provide variable illumination. First, laser light has brighter illumination as compared to conventional LEDs which enables shortening the exposure time of raw intensity image acquisition. For example, certain LFP systems have exposure times in the range of about 10 microseconds to about 100 milliseconds per frame as compared to LED-based systems which have exposure times in the range of 10 millisecond to 10 seconds per frame that typically use average consumable LEDs with relatively low power. Shorter exposure time can provide an imaging scheme with higher temporal resolution suitable for resolving transient biological processes. Since the duration of an imaging cycle is mostly driven by the time intensive raw image acquisition process, using laser light significantly reduces the cycle time (e.g., range of 100 milliseconds to less than about 10 seconds) as compared to LED-based systems (e.g., range of more than 10 seconds to 1000 seconds). Additionally the broader range and finer spectrum of a laser light source potentially allows for spectral imaging capability. Conventional LED-based systems used LEDs with a broad spectrum and a limited number of choices for the central wavelength. Thus, the potential application of conventional LED-based Fourier ptychography systems was limited to the spectra offered by the LEDs.

As introduced above, various aspects described herein relate to LFP imaging systems that implement LFP methods to obtain high-resolution images of a sample. In certain implementations, LFP imaging systems include a specimen surface for receiving a sample being imaged, an angle direction device, an optical system, and a light detector such as an image sensor. The angle direction device is configured or configurable to direct laser light from a laser light source to the specimen surface at a sequence of illumination angles. The optical system comprises a collection element (e.g., lens) for receiving light issuing from the sample when it is illuminated from laser light directed by the angle direction device. The optical system also includes a focusing element (e.g., lens) for focusing light propagated from the collection element to the light detector. In some cases, the LFP imaging system further includes a controller in communication with the angle direction device and/or laser light source and configured to cause laser light from the laser light source to be directed by the angle direction device to the specimen surface at the sequence of illumination angles at particular sampling times. The controller may also be in communication with the light detector to synchronize exposure time of the light detector for measuring the intensity distribution data of each raw intensity image while laser light is illuminating from one of the sequence of illumination angles. Intensity distribution data is measured at the light detector when the sample is illuminated at each of the illumination angles. The intensity distribution data measured at the light detector when the sample is illuminated at a particular illumination angle is referred to herein as an "intensity image" or "raw image" corresponding to the particular illumination angle. A sequence of intensity images of the sample is acquired over the course of an entire "image acquisition phase" during which the sample is sequentially illuminated at different illumination angles. The optical system focuses light scattered by the sample onto a light detector. Over the course of the image acquisition phase, the light detector takes a sequence of intensity distribution measurements (intensity images), one raw intensity image being measured for each illumination angle. A processor combines the raw intensity images in the spatial frequency domain using a reconstruction process to correct aberrations and to render a single high-resolution image of the sample.

Since the laser light is generally brighter than light from standard LEDs, holding the sensitivity of the light detector constant, use of a laser light source allows for a faster image acquisition phase than if standard LEDs were used. The LFP imaging systems and methods described herein allow for a compact imaging system that is able to acquire a sufficient number of intensity images to generate a high resolution image of a sample over a short image acquisition phase, e.g. potentially less than 1 second. In one embodiment, an LFP system can be configured to generate a high resolution image of a sample in less than 1 second. In another embodiment, an LFP system can be configured to generate a high resolution image of a sample in less than 10 seconds. In another embodiment, an LFP system can be configured to generate a high resolution image of a sample in less than 60 seconds. In one embodiment, an LFP system can be configured to generate a high resolution image of a sample in a range of 1 to 100 seconds. In one embodiment, an LFP system can be configured to acquire an intensity image at a rate of 100 per second. In one embodiment, an LFP system can be configured to acquire an intensity image at a rate of 1000 per second.

The LFP imaging systems disclosed herein have additional benefits compared to e Fourier ptychography imaging systems that use standard LEDs. By way of example, as discussed above, certain LFP imaging systems described herein are capable of capturing sufficient intensity images to generate a high resolution image of a specimen in a relatively short amount of time. Therefore, unlike slower FP imaging systems that use standard LEDs, LFP imaging systems may more effectively image moving specimens.

Some examples of LFP imaging systems are described in further detail below with reference to the Figures.

I. Laser-Based Fourier Ptychographic (LFP) Systems

A. LFP Systems

FIG. 1 is a block diagram of an LFP imaging system 100 capable of implementing an LFP imaging method, according to embodiments. At a high level, the LFP imaging system 100 is configured or configurable to sequentially illuminate a sample being imaged by laser light directed at different illumination angles, to capture a sequence of intensity images where each intensity image is captured when the sample is illuminated by laser light directed at one of the illumination angles, and process the raw image data to reconstruct a full resolution complex image of the sample while correcting for any aberrations from, for example, speckles generated through the use of laser light.

The LFP imaging system 100 includes a laser illumination system 110, an optical system 120, an imaging system 130, a controller 140, a communication interface 150, and a display 152 in communication with the communication interface 150, and internal memory 160. The LFP imaging system 100 also optionally (denoted by dashed line) includes a communication interface 170 and an external computing device or system 172 in communication with the communication interface 170. The LFP imaging system 100 also optionally includes a communication interface 180 and an external memory device or system 182 in communication with the communication interface 180 for optional storage of data to the external memory device or system 182. The LFP imaging system 100 also optionally includes a network communication interface 190 and an external network 192 (for example, a wired or wireless network) communication with the communication interface 190. Each of the communication interfaces 150, 160, 170, 180, 190 is in communication with the controller 140. The laser illumination system 110 is configured or configurable to provide laser light illumination from a sequence of illumination angles. The optical system 120 generally has one or more lenses that propagate light issuing from the sample to one or more light detectors of the imaging system 130. The controller 140 is in communication with the internal memory 160 to retrieve and store data to the internal memory 160. The controller 140 is configured or configurable to output raw image data, processed image data, and/or other data over a communication interface 150 for display on a display 152. The controller 140 is in communication with the imaging system 130 which is in communication with the optical system 120. The described communication between components of the LFP imaging system 100 may be in wired form and/or wireless form.

The controller 140 comprises one or more processors which are in communication with internal memory 160 and/or other computer readable memory (CRM). The controller 140 controls operations of the LFP imaging system 100 based on instructions stored in memory (e.g., internal memory 160). The controller 140 is in electrical communication with the imaging system 130 to receive the raw image data from the imaging system 130. Optionally (denoted by dotted lines), the controller 140 may also be in electrical communication with the laser illumination system 110 to control illumination, for example, in order to synchronize the illumination with the exposure times during acquisition of intensity images by the imaging system 130. The controller 140 or another processor controls the illumination from laser light source(s). For example, the controller 140 or another processor may control the operation of an angle direction device that directs light from the laser light source(s) to at predefined illumination angles at particular times and for particular durations during various image acquisition exposures and/or control the activation of laser light source(s), for example, by powering on during the image acquisition phase. In some implementations, the controller 140 is further configured to execute instructions to perform processing operations on the raw image data such as operations performed as part of the LFP imaging method.

The imaging system 130 is in communication with the optical system 120 to receive light from the optical system 120 and capture raw images while the sample is on the specimen surface and illuminated, each raw image captured over an exposure time. The laser illumination system 110 is in communication with the optical system 120 to provide laser light to a sample being imaged on the specimen surface such that light scattered by or otherwise issuing from the sample is propagated through the optical system 120 to light detector(s) of the imaging system 130 which capture the raw images. When laser light illuminates the sample, light scattered or otherwise issuing from the sample is propagated through the optical system 120 to the imaging system 130 which captures a sequence of intensity images.

The LFP imaging systems described herein include an angle direction device. An angle direction device generally refers to one or more components that are configured or configurable to guide a laser beam to the sample plane at N different illumination angles at N different image sampling times. During the image acquisition phase, the sample being imaged is located on the specimen surface at the sample plane and the laser light is directed to the sample being imaged. In certain embodiments, N has a value in a range of between 2 to 1000. In one case, N has a value in a range of between 90 and 200. In one case, N=95. In one case, N is less than 100. In one case, N is less than 200. In one case, N has a value in a range of between 50 and 100. In one case, N has a value in a range of between 2 and 100. In one case, N has a value in a range of between 100 and 200.

Generally the angle direction device is designed to guide the laser beam to the sample plane to provide oblique illumination. The angle direction device is typically optically coupled with (or includes) one or more laser light sources. The angle direction device also includes one or more devices for directing the laser beam from the laser light source to the specimen surface at the N different illumination angles described in the preceding paragraph. For example, the angle direction device may include one or more mirrors and/or movement mechanisms to direct the laser beam sequentially to the different illumination angles at the appropriate sampling times. In one embodiment, the angle direction device includes an optical port for receiving an optical fiber coupled with the laser light source(s) and is able to translate and/or rotate the optical fiber to provide the oblique illumination described above. In one implementation, the angle direction device includes multiple optical ports for receiving multiple optical fibers. In this case, the angle direction device may also include one or more optical switches for switching laser light from the laser light source to a single optical fiber. In another implementation, the angle direction device may include one or more rotatable mirrors that direct light from the laser light source by way of an array of fixed mirrors, each of which may be positioned to illuminate the specimen surface at one of the illumination angles. In yet another implementation, the angle direction device may include one or more rotatable mirrors that direct light from the laser light source to the specimen surface by way of a system of lenses that refract the light from the laser light source to illuminate the specimen surface at each of the illumination angles.

The angle direction device is generally configured or configurable to cause light from the laser light source to illuminate the sample plane at the specimen surface at different angles sequentially. The image data from the sequence of images captured based on illumination at different illumination angles corresponds to overlapping regions in Fourier space. The angle direction device is typically configured to direct laser light to illuminate at a sequence of illumination angles that provide for an overlapping area of neighboring regions of image data in Fourier space where the overlapping area is of at least a certain minimum amount (e.g. 65% overlap, 75% overlap, 70% overlap, 80% overlap, in a range of 10%-65% overlap, in a range of 65%-75% overlap, etc.). To provide this minimum amount of overlap of neighboring regions in Fourier space, the angle direction device may have elements that are configured so that the difference between adjacent illumination angles is less than a certain maximum angular difference.

The laser light source(s) may be a component of or may be separate from the LFP system 100. The intensity of light provided by the laser light source may vary, for example, depending on the type of sample being imaged. By way of example, dead skin samples can tolerate a power per unit area of up to several W/cm$^2$. On the other hand, non-biological samples may be able to tolerate a much higher power per unit area without being degraded. Although examples described herein typically discuss a laser light source that provides visible light e.g. some of the LFP imaging systems disclosed herein generally operate with a laser light source with a wavelength in the visible range between 400 nm and 750 nm, the disclosure is not so limiting. In other embodiments, the laser wavelength may be in the ultra-violet region or in the infra-red region and the focusing element and glass surfaces of the LFP system would need to be appropriately substituted to work in these different wavelength ranges. In addition, other sources of laser radiation may be used, e.g. a maser, a free electron laser, an x-ray laser, an acoustic laser, etc. When different types of lasers are used, many of the optical elements, e.g. lenses or mirrors, disclosed herein may be substituted with suitable alternatives. By way of example, where an X-ray or microwave laser is used, mirrors and/or lenses that are configured to reflect or refract x-rays or microwaves respectively may be included as substitutes for lenses and or mirrors described and/or depicted in figures herein.

The LFP systems described herein include an optical system that is generally configured to propagate illumination issuing from the sample to the one or more light detectors to be able to capture raw images of the sample. The optical system comprises at least a collection element and a focusing element. The collection element (e.g., lens) of an LFP system comprises one or more lenses and is designed to collect light scattered by or otherwise issuing from the specimen at the sample plane. Some examples of suitable collection elements include an f=50 mm lens (e.g., f/1.8 D AF Nikkor), 4× Olympus Plan Achromat objective 0.10 NA, CFI Plan Achromat 10× objective NA 0.25, an Valumax objective lens 5× 0.10 NA, and the like. The focusing element comprises one or more lenses and is located to receive incident light from the optical system and focus the light to the light detector. An example of suitable focusing elements include a tube lens (e.g., a f=200 mm tube lens such as the Thorlabs® ITL200 tube lens). Although certain illustrated examples are shown with the collection and focusing elements arranged in a 4f arrangement, it would be understood that the disclosure is not so limiting and that other arrangements can be used. For example, the collection and focusing elements can be arranged in a 6f arrangement. In other examples, other optical elements such as bandpass filters, beam splitters, and/or mirrors can be included.

In some embodiments, the optical system of an LFP system has an iris located at the back focal plane of the collection element of the optical system. An iris generally refers to a circular aperture that can be adjusted in diameter to limit the amount of light collected by the optical system. Reducing the diameter and blocking out the outer region of light is equivalent to reducing the NA of the collection element, which means blocking out high spatial frequency information of the sample. Placing the iris is useful to accurately define the NA of the imaging system for the purpose of the LFP imaging method to prevent aliasing in the detected images, etc. There are different ways to control the size and shape of the iris. In one example, one can use a mechanical iris which has its diameter adjustable with a slider (e.g. Ring-actuated SM2 iris diaphragm from Thorlabs). As another example, an iris may be a transmissive liquid crystal display (LCD) that can adjust the contrast of its pixel elements to produce an aperture. As another example, light may be guided to an SLM or DMD and then only a part of the beam reflected back into the system's optical path by turning on different elements on the SLM or DMD. With the use of an LCD, SLM, and DMD, the iris's shape is not limited to a circle because any discretized shape can be displayed on these displays and thus, the shape and size may be defined as the operator desires.

In some cases, the collection element, focusing element, illumination elements, and other components of the LFP system may be selected based on the particular imaging implementations. For example, when imaging a histological sample, the appropriate system NA (objective NA+illumination NA) provided by selecting a particular collection element and illumination elements may be in the range of 0.5-0.75. The objective NA may be 0.05-0.2 and the illumination NA 0.4-0.7 to provide this system NA, for example. On the other hand, if a blood smear is being analyzed for malaria, a system NA in the range of 1.2-1.5 may be desired.

Generally, the LFP systems described herein includes one or more light detectors. In certain examples, such as the one shown in FIG. 1, the LFP system includes an imaging system 130 comprising one or more light detectors. According to certain implementations, a light detector is configured to capture light and output a data signal including image data representative of the measured intensities of light received at particular locations of the active surface of the light detector (referred to herein as a "light intensity distribution," "intensity distribution," or simply as an "intensity image," "raw intensity image," "image," or "image frame"). The image data output by the light detector(s) is transmitted (or "sent" or "communicated") in a signal to a processor of, for example, a controller such as controller 140. The light detector(s) of an LFP imaging system can acquire a sequence of N raw intensity images during the image acquisition process. Each light detector acquires an intensity image by measuring an intensity distribution of light incident on the sensing area of light detector during an exposure time. Some examples of suitable light detectors are CMOS sensors, a charge-coupled device (CCD), and other similar imaging devices. In one example, a light detector is a CCD having a pixel size of 5.5 μm such as the Prosilica GX6600 light detector. In certain implementations, the one or more light detectors in an LFP system are monochromatic light detectors.

The exposure time refers to the duration of time during which the light detector(s) measures a light intensity distribution of light received at its active surface to capture a single raw intensity image. The exposure time used to capture an intensity image by the light detector(s) of various implementations of the LFP systems depends on both the sensitivity of the light detector(s) and the intensity of the laser light from the one or more laser source(s). In other words, increasing the sensitivity of the light detector(s) and/or the intensity of the laser light source decreases the exposure time. As such, the LFP imaging systems described herein may be configured for particular exposure times based on the laser light source used. For example, a range of exposure times from 100 μs to 10 ms may be used for an LFP imaging system with a light detector in the form of a sCMOS detector and with a laser light source having a range of light intensities from 100 μW to 10 mW.

Each of the LFP systems described herein is configured to implement an LFP imaging method. Each imaging cycle of the LFP imaging method generally includes a raw intensity image acquisition phase, a high-resolution reconstruction phase, and an optional display phase. During the raw image acquisition phase, light generated by the laser light source(s) and directed by the angular direction device illuminates the sample plane at different illumination angles sequentially. The sample is typically located on the specimen surface approximately located at the sample plane during the image acquisition phase. Laser light incident on the sample is scattered by the physical features of the sample as it passes through the sample. A portion of the scattered light then passes to the collection element of the optical system. The focusing element of the optical system focuses the scattered light from the sample to one or more light detectors. The one or more light detectors capture a sequence of raw intensity images during sequential illumination of the sample with laser light at the sequence of illumination angles. The processor(s) (e.g., processor of a controller) sends control signals to various system components to control their operations. The processor(s) controls the operations of the angular direction device and/or the light detectors by sending control signals.

During the high-resolution reconstruction phase, the processor(s) processes the raw image data from the image acquisition phase to generate processed image data. In some implementations, the processor(s) are configured or configurable to perform LFP processing operations on the image data of a sequence of intensity images. In these cases, the processor(s) interpret raw image data from the sequence of acquired intensity images, transform the relatively low-resolution raw intensity image data into Fourier space, iteratively update the transformed raw image data in Fourier space to reconstruct amplitude and phase data for a single high-resolution image of the sample and the pupil function of the LFP imaging system. In some cases, the one or more processors use a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 to display data such as the high-resolution image and other data.

In certain implementations, the processor(s) of an LFP system may be configured to perform parallel image processing such as, for example, when processing multiple tile images (i.e. portions of the full field of view image) to reconstruct phase and amplitude data for multiple tile images in parallel. These tile images can then be combined to form the full field of view image. To perform parallel image processing, the controller would be configured to include at least one processor (or "processing unit"). Some examples of processors that can be used to perform parallel processing or non-parallel processing include, for example, a general purpose processor (CPU), an application-specific integrated circuit, an programmable logic device (PLD) such as a field-programmable gate array (FPGA), or a System-on-Chip (SoC) that includes one or more of a CPU, application-specific integrated circuit, PLD as well as a memory and various interfaces.

Returning to FIG. 1, the controller 140 is in communication with internal memory device 160. The internal memory device 160 can include a non-volatile memory array for storing processor-executable code (or "instructions") that is retrieved by the processor to perform various functions or operations described herein for carrying out various operations on the image data. The internal memory device 160 also can store raw and/or processed image data. In some implementations, the internal memory device 160 or a separate memory device can additionally or alternatively include a volatile memory array for temporarily storing code to be executed as well as image data to be processed, stored, or displayed. In some implementations, the controller 140 itself can include volatile and in some instances also non-volatile memory.

In FIG. 1, the controller 140 is in communication with the communication interface 150 which is in communication with the display 152. In certain implementations, the controller 140 is configured or configurable by an operator to output raw image data or processed image data over the communication interface 150 for display on the display 152. In some implementations, the controller 140 also can be configured or configurable by to output raw image data as well as processed image data (for example, after image processing) over a communication interface 170 to an external computing device or system 172. Indeed, in some implementations, one or more of the LFP operations can be performed by such an external computing device 172. In some implementations, the controller 140 also can be configured or configurable by a user to output raw image data as well as processed image data over a communication interface 180 for storage in an external memory device or system 182. In some implementations, the controller 140 also can be configured or configurable by a user to output raw image data as well as processed image data (for example, after image processing) over a network communication interface 190 for communication over an external network 192 (for example, a wired or wireless network). The network communication interface 190 also can be used to receive information such as software or firmware updates or other data for download by the controller 140. In some implementations, the LFP imaging system 100 further includes one or more additional interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the laser illumination system 110 can be electrically coupled to communicate with the controller 140 over one or more of a variety of suitable interfaces and cables such as, for example, USB interfaces and cables, ribbon cables, Ethernet cables, among other suitable interfaces and cables.

In some embodiments, the data signals output by the light detectors of an LFP system may be multiplexed, serialized or otherwise combined by a multiplexer, serializer or other electrical component of the imaging system before being communicated to the controller. In certain implementations, the controller can further include a demultiplexer, deserializer or other device or component for separating the image data from each of the light detectors so that the image frames can be processed in parallel by the controller or for separating the image data from each tile image so that the sequence of image frames of each tile image can be processed in parallel by the controller.

Some examples of LFP systems are shown in FIGS. 2-6. Some of these LFP systems have certain components that are similar to those of the LFP system 100 in FIG. 1 above.

B. LFP Systems with a Scanning Fiber Port

Certain implementations of an LFP imaging system include an angle direction device with a scanning fiber port. In these implementations, laser light is coupled to one end of an optical fiber and the other end of the optical fiber is attached with a fiber connector or directly to an optical port (also called output port) in a movable stage. The movable stage is configured to translate the end of the optical fiber in a plane and/or rotate the end of the optical fiber. An example of a movable stage is a two-axial motorized stage such as an X-Y stage. The movable stage is generally configured to move (also referred to as scan) the optical fiber to provide the sample plane with angularly varying illumination from a sequence of illumination angles.

Figure 2:
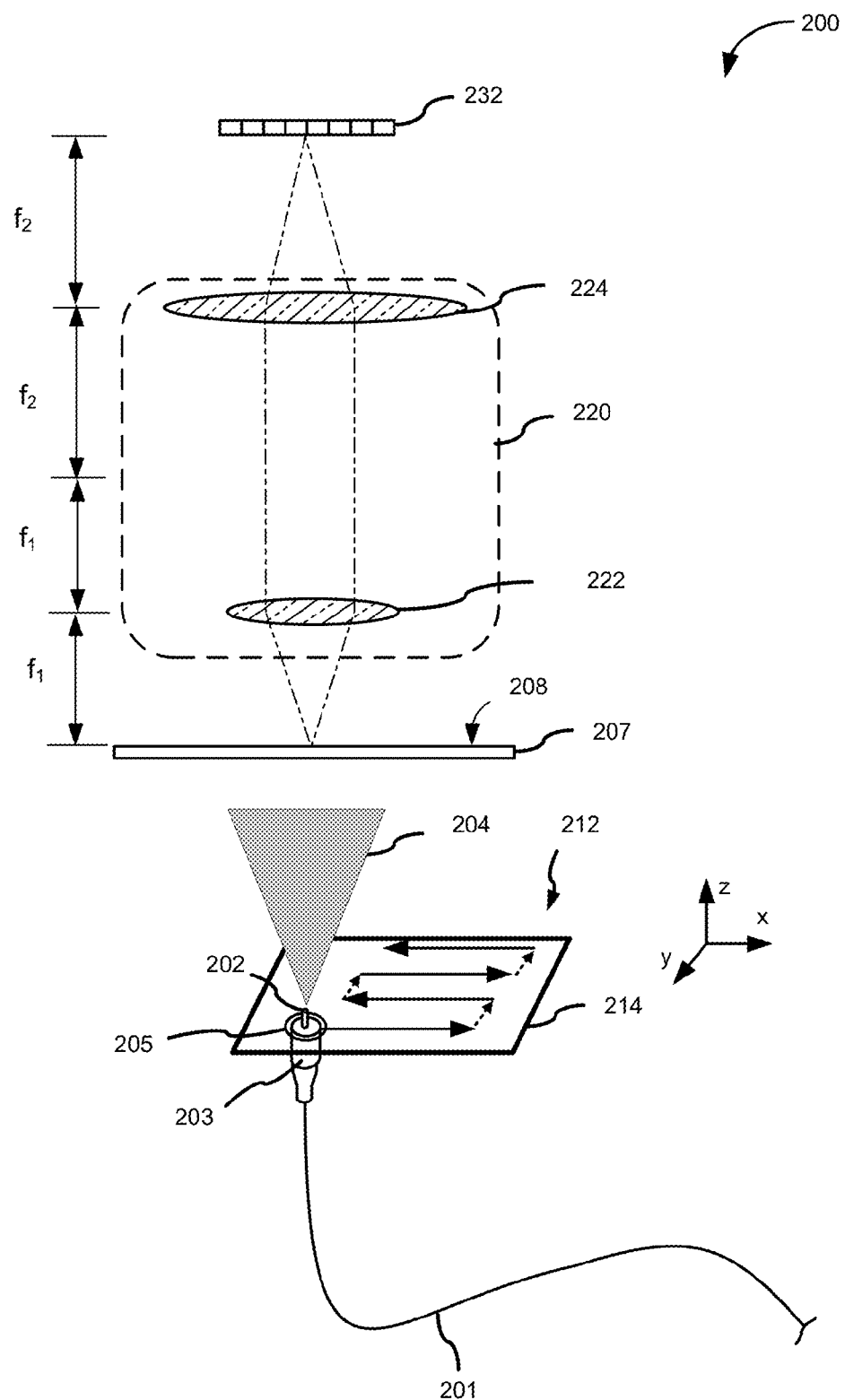
FIG. 2 shows a schematic drawing of a cut-away view of an example of an LFP imaging system, in accordance with some implementations.

FIG. 2 is schematic drawing of an example of an LFP imaging system 200 with a scanning fiber port, in accordance with some implementations. An optical fiber 201 is shown with an end 202 within a fiber connector 203 coupled to an optical port 205 in a movable stage 212. Although shown with a fiber connector 203, it would be understood that the optical fiber 201 could be placed directed in the optical port 205 in another embodiment. The other end (not shown) of the optical fiber 201 is optically coupled with a laser light source(s) and receives laser light from the laser light source(s) when activated. In the illustrated example, the laser light source(s) is activated and laser light 204 spreads conically from the end 202 proximal to the fiber connector 203. A transparent layer 207 with a specimen surface 208 is also shown. The specimen surface 208 can receive a sample (not shown) being imaged. In some cases, one or both of the fiber connector 203 and the optical fiber 201 are components of the LFP imaging system 200. In other cases, the fiber connector 203 and optical fiber 201 are separate components from the LFP imaging system 200.

The LFP imaging system 200 comprises an angular direction device 212 having a movable stage 214 with an optical port 205 configured to receive the optical fiber 201. With the optical fiber 201 coupled to the optical port 205, the movable stage 214 is configured or configurable to move (translate/rotate) the optical fiber 201 to direct illumination at a plurality of illumination angles to the sample plane. The LFP imaging system 200 further comprises an optical system 220 having a collection element 222 and a focusing element 224, and a light detector 232 for receiving light propagated by the optical system 220. Although the illustrated example shows the movable stage 214 as having an optical port 205 in the form of a circular aperture, it would be understood that other receiving configurations for the optical port 205 could be used. A series of arrows are depicted in FIG. 2 to show an example of the direction of translational movement of the optical fiber 201 during an image acquisition phase of one implementation. Other implementations may include other translation patterns or may include rotational movement as well. In yet other implementations, the movable stage 214 may be configured for two axis rotational movement.

In one embodiment, the LFP imaging system 200 also includes one or more processors and computer readable medium (CRM) (e.g., memory) in communication with the processor(s). The one or more processors and computer readable medium may be part of a controller such as the controller 140 described with respect to FIG. 1. The processor-executable code (or "instructions") for performing the LFP imaging method can be stored on the CRM or other memory. The processor(s) and can retrieve the processor-executable code from the CRM or other memory to perform various functions or operations of the LFP imaging method. The CRM or other memory can store raw and/or processed image data. In some implementations, the CRM or other memory can additionally or alternatively include a volatile memory array for temporarily storing code to be executed as well as image data to be processed, stored, or displayed.

The LFP Imaging system 200 also includes an optical system 220 having a collection element 222 (e.g., lens) having a focal length, $f_1$, and a focusing element 224 (e.g., lens) having a focal length, $f_2$. The collection element has an objective NA and is configured to receive light issuing from a specimen when it is located on the specimen surface 207. The focusing element 224 is configured to focus light propagated from the collection element 222 to the light detector 232. The sequence of illumination angles and the objective NA correspond to overlapping regions in the Fourier domain, as described in further detail below. In the illustration, the optical system 220 is in a 4f arrangement where the collection element 222 is located so that the sample plane is $f_1$ apart from it. The sample's Fourier plane is located $f_1$ away on the other side of 222. Fourier plane of the sample at the sample plane at specimen surface 208 is a focal length, $f_2$, away from the focusing element 224 and the focusing element 224 is located a distance of a focal length, $f_2$, away from the light detector. Other arrangements can be used. For example, a 6f arrangement can be used. As another example, other optical elements (e.g., mirrors, bandpass filters, beam splitters, etc.) can be introduced into the optical path for other arrangements.

The LFP imaging system 200 further comprises a light detector 232 with eight discrete light elements. Although shown with eight discrete light elements, it would be understood that other numbers of light elements could be used. The collection element 222 is configured to receive light issuing from the sample (not shown) being illuminated on the specimen surface 208 and the focusing element 224 focuses light propagated from the collection element 222 to the light detector 232.

While laser light 204 issuing from the optical fiber 201 is depicted as spreading conically outwards with a particular width, the width of this cone depends on the NA of the optical fiber 201. Different types of optical fibers may be used to achieve the desired illumination. By way of example, a single mode fiber optic with an NA in the range of 0.1-0.4 may be used to achieve a narrower cone. In another example, a multi-mode fiber with an NA in the range of 0.1 to 0.8 may be used to achieve a wider cone.

The movable stage 214 may be any kind of stage to which the optical fiber 201 with or without the fiber connector 203 can be attached and that can be configured to translate and/or rotate the optical fiber 201 to direct the optical fiber 201 to provide a laser beam to a sample plane at a specimen surface 208 at a sequence of illumination angles as described in the section above in the context of the FIG. 1. For instance, at a particular sampling time, the movable stage 214 may cause the optical fiber 201 to translate/rotate to a particular position/direction at which laser light from the optical fiber 201 illuminates a sample plane at the specimen surface 207 at a particular one of the illumination angles in the sequence of illumination angles. Once the fiber connector 203 has illuminated the sample plane at the particular illumination angle for at least the exposure time such that a light detector 232 may acquire an intensity image, the movable stage 214 may cause the optical fiber 201 to translate/rotate to another position/direction at which the optical fiber 201 provides the laser beam to the sample plane at another one of the illumination angles. The optical fiber 201 may remain at each position/direction for at least the exposure time of the light detector 232 for generating an intensity image. This raw image acquisition phase may continue until the sample has been illuminated at all of the illumination angles at the different sampling times.

The movable stage 214 may cause optical fiber 201 to translate and/or rotate in the positions described in the preceding paragraph in a variety of manners. In the illustrated example, the movable stage 214 is configured to cause the optical fiber 201 to translate linearly in the x-direction and then shift to different locations in the y-direction in order to scan back and forth in the X-Y plane. In this manner, the optical fiber 201 provides a laser beam to illuminate the sample from N different positions in the X-Y plane along the arrows in FIG. 2. Alternatively, the movable stage 214 may be configured to cause the optical fiber 201 to translate spirally outwards such that the optical fiber 201 may illuminate the sample from N positions along a spiral moving to successive points in an r-θ plane. In one implementation, the movable stage 214 is an X-Y stage.

The movable stage 214 may be controlled in a variety of manners. By way of example, a processor (e.g. a processor of the controller 140 of FIG. 1) or processors may be in communication with movable stage 214. The processor may retrieve instructions stored in a memory (e.g. internal memory 160 of FIG. 1) and the instructions may be executable to cause the movable stage 214 to translate and/or rotate such that the optical fiber 201 is positioned/directed to provide the laser light to the sample sequentially at different illumination angles at different sampling times. In some case, the movable stage 214 holds the optical fiber 201 at the position for at least the duration of the exposure time used acquire an intensity image by the light detector 232. Alternatively, the movable stage 214 may have an internal memory and processor and may be programmed to cause the fiber connector 203 to follow a pre-determined path.

It would be understood to those skilled in the art that the fiber connector 203 may have shapes other than the one illustrated in FIG. 2. In addition, it would be understood that the optical fiber 201 may be directly attached to the movable stage 214 or may be attached through the fiber connector 203 to the movable stage 214.

At the instant in time illustrated in FIG. 2, the angle direction device 212 is illuminating a sample (not shown) on the specimen surface 208. Generally, light incident on the specimen is scattered by the physical features of the specimen as it passes through the specimen. The collection element 222, which have a particular objective NA, receives light passing through the specimen. If an iris is included in optical system 220, it would be placed at the back focal plane of 222. The optional iris receives light propagated by the collection element 222 and passes light incident on its pupil area. Light incident on the area of the iris around the pupil area is substantially blocked. The focusing element 224 receives the light passed by the iris and focuses the light to the light detector 232. The light detector 232 is configured to receive light focused by the focusing element 224 and acquire an intensity image of the sample over each exposure time when the sample is on the specimen surface and illuminated by laser light from the angle direction device 212. The light detector 232 is configured to capture a sequence of raw intensity images while the angle direction device 212 provides laser light sequentially from different illumination angles at the different sampling times.

During the high-resolution reconstruction phase, one or more processors of the LFP system 200 interpret and process the raw image data from the sequence of images acquired during the image acquisition phase to generate processed image data. The one or more processors interpret raw image data from the sequence of acquired intensity images, transform the relatively low-resolution raw image data frames into Fourier space, iteratively update the transformed raw image data in Fourier space to reconstruct amplitude and phase data for a single high-resolution image of the sample and the associated pupil function of the imaging system. In some cases, the one or more processors uses a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 in FIG. 1 to display data such as the high-resolution image and other data.

C. LFP Systems with a Fiber Array Structure

Certain implementations of an LFP imaging system include an angular direction device with a fiber array dome or other shaped structure for receiving an array of optical fibers at fixed locations. In these implementations, the surface wall of the fiber array dome or other structure has an array of optical ports for receiving and holding in place an array of optical fibers in directions that will provide laser illumination from a plurality of illumination angles. For example, the optical ports may be apertures or other holder, each designed to receive a fiber connector at one end of an optical fiber or the one end of the fiber directly without the fiber connector. The other end of each of the optical fibers is optically coupled to an optical switch. The optical switch is connected to another optical switch or directly to the laser source(s). The optical switch(es) may be controlled by a controller or other computing device. In certain implementations, an optical switch may couple one fiber channel to the laser light source at a time, providing illumination on the specimen surface plane at a certain angle. Although the surface wall is a dome-shape in the illustrated example below, it would be understood that other shapes can be used. In one embodiment, the surface of the fiber array structure may be a flat plate with slanted apertures. In another embodiment, the fiber array structure may be a truss structure.

As mentioned above, the LFP imaging systems with a fiber array dome, one or more optical switches can be used. In implementations where a single optical switch is used, the optical switch is configured to switch to each of the optical fibers. In other cases, multiple optical switches are used. For example, a cascade arrangement of multiple optical switches in series can be used. Each output end of an optical switch may be connected to the input end of a separate optical switch to increase the number of optical fiber outputs from the laser source(s) available for the fiber array dome design. An example of an optical switch that can be used in series is a mol 1×16 19" 2 HU from Leoni Fiber Optics® that can switch the light output to 16 optical fibers given one input light source.

Figure 3:
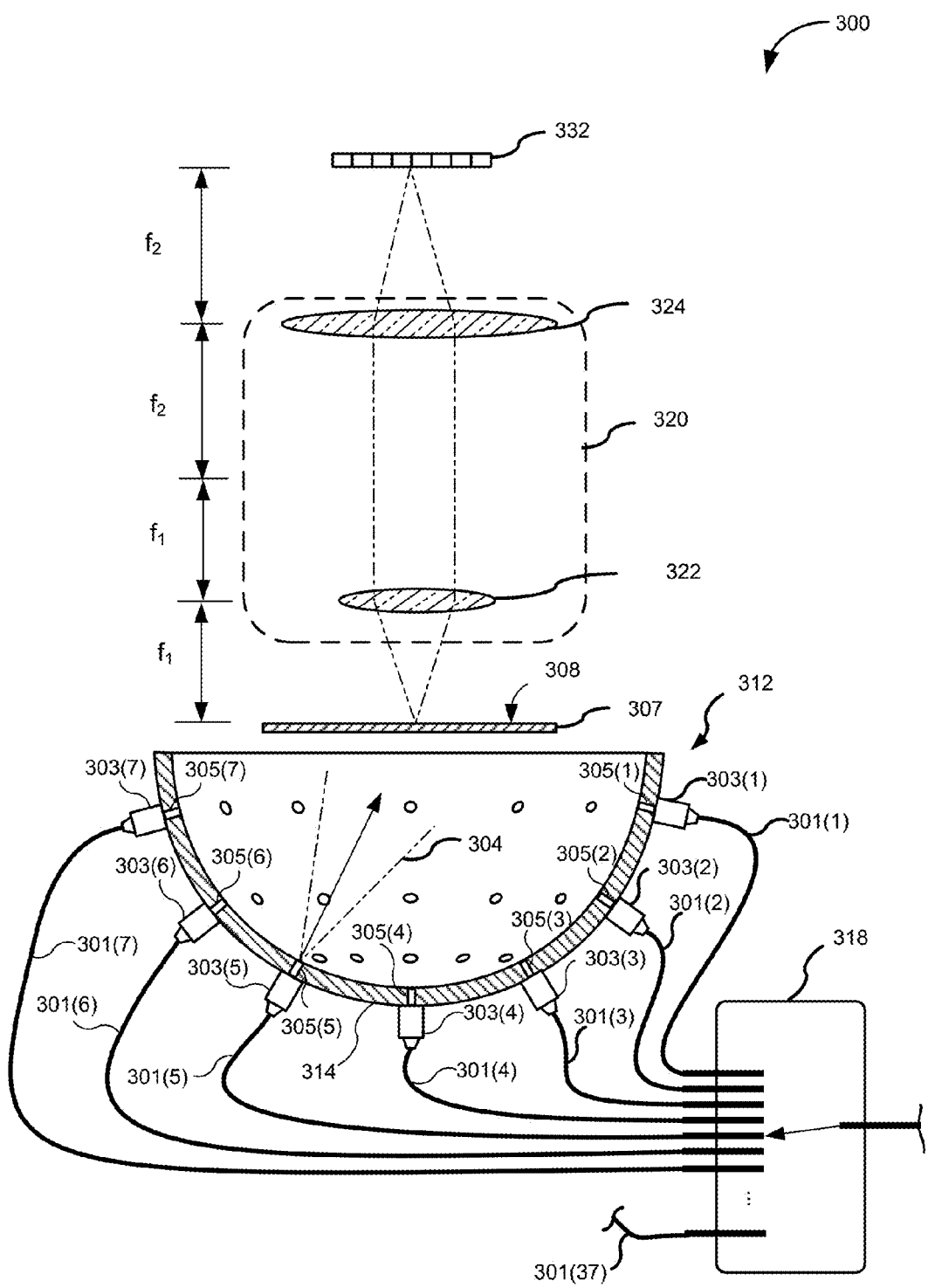
FIG. 3 shows a schematic drawing of a cut-away view of another example of an LFP imaging system, in accordance with some implementations.

FIG. 3 is a schematic drawing of a cutaway view of an LFP imaging system 300 comprising an angle direction device 312 having a fiber array dome 314, in accordance with some implementations. The fiber array dome 314 is configured to receive and direct optical fibers 301(1) through 301(37) at a plurality of illumination angles to the sample plane. The fiber array dome 314 comprises thirty-seven (37) optical ports 305(1) through 305(37) for receiving and holding optical fibers 301(1) through 301 (37) with respective fiber connectors 303(1) through 303 (37). In this cutaway view, seven (7) optical ports 305(1) through 305(7) are shown with fiber connectors 303(1) through 303 (37) and their respective optical fibers 301(1) through 301 (37). It would be understood that the fiber array dome 314 may be configured with more or fewer optical ports 305. For example, the fiber array dome 314 could be configured with ninety-seven (97) optical ports 305.

The LFP imaging system 300 further includes an optical switch 318. Each optical fiber 301 is shown with a first end located within a respective fiber connector 303 held within a respective fiber port 305. The second end of each optical fiber 301 is optically coupled to an optical switch 318. Each optical port 305 holds the respective optical fiber 301 in a position/direction such that when the laser light source(s) (not shown) is activated and the optical switch 318 is switched to provide laser light to the respective optical fiber 301 at its second end, laser light is propagated through the optical fiber 301 and directed out the first end at a particular illumination angle. In the illustrated example, the respective fiber port 305(5) holds the respective optical fiber 301(5) in a position/direction to direct the laser light 304 spreading conically from the first end of optical fiber 301(5) proximal of the optical port 305(5). A bisecting arrow through the cone is shown depicting the illumination angle of the laser light from the first end of the optical fiber 301(5). A transparent layer 307 (e.g., slide) with a specimen surface 308 is also shown. The specimen surface 308 can receive a sample (not shown) to be imaged. The transparent layer 307, the optical fibers 301, the optical ports 305, fiber connectors 303, and/or the optical switch 318, may be components of or may be separate components from the LFP imaging system 300.

In the illustrated example, the LFP imaging system 300 further comprises an optical system 320 having a collection element 322 and a focusing element 324, and a light detector 332 for receiving light propagated by the optical system 320. The collection element 322 (e.g., lens) has a focal length, $f_1$, and the focusing element 324 (e.g., lens) has a focal length, $f_2$. The collection element has an objective NA and is configured to receive light issuing from a specimen when it is located on the specimen surface 308. The focusing element 324 is configured to focus light propagated from the collection element 322 to the light detector 332. The sequence of illumination angles and the objective NA correspond to overlapping regions in the Fourier domain, as described in further detail below. In the illustration, the optical system 320 is in a 4f arrangement where the collection element 322 is located so that the sample plane is $f_1$ apart from it. The sample's Fourier plane is located $f_1$ away on the other side of 322. Fourier plane of the sample at the sample plane at specimen surface 308 is a focal length, $f_2$, away from the focusing element 324 and the focusing element 324 is located a distance of a focal length, $f_2$, away from the light detector. Other arrangements can be used. For example, a 6f arrangement can be used. As another example, other optical elements (e.g., mirrors) can be introduced into the optical path for other arrangements.

The LFP imaging system 300 further comprises a light detector 332 with eight discrete light elements. Although shown with eight discrete light elements, it would be understood that other numbers of light elements could be used. The collection element 322 receives light issuing from the sample (not shown) on the specimen surface 308 and the focusing element 324 focuses light propagated from the collection element 322 to the light detector 332.

In one embodiment, the LFP imaging system 300 also includes one or more processors and computer readable medium (CRM) (e.g., memory) in communication with the processor(s). The one or more processors and computer readable medium may be part of a controller such as the controller 140 described with respect to FIG. 1. The processor-executable code (or "instructions") for performing the LFP imaging method can be stored on the CRM or other memory. The processor(s) and can retrieve the processor-executable code from the CRM or other memory to perform various functions or operations of the LFP imaging method. The CRM or other memory can store raw and/or processed image data. In some implementations, the CRM or other memory can additionally or alternatively include a volatile memory array for temporarily storing code to be executed as well as image data to be processed, stored, or displayed.

While laser light 304 issuing from the optical fiber 301(5) is depicted as spreading conically outwards with a particular width, the width of this cone depends on the NA of the optical fiber 301(5). Different types of optical fibers may be used to achieve desired illumination. By way of example, a single mode fiber optic with an NA in the range of 0.1-0.4 may be used to achieve a narrower cone or a multi-mode fiber with an NA in the range of 0.1 to 0.8 may be used to achieve a wider cone.

The LFP system 300 also includes an optical switch 318 in optical communication with the laser light source (not shown). The optical switch 318 is also in optically communication with optical fibers 301(1) through 301(37). The optical fibers 301(1) through 301(37) are coupled to respective fiber connectors 305(1) through 305(37). As introduced above, the optical ports 305(1) through 305(37) are designed to direct laser light from the optical fibers 301(1) through 301(37) within the fiber connectors 305(1) through 305(37) to the specimen surface 308 such that a specimen on the specimen surface 308 may be sequentially illuminated with the laser light from thirty-seven (37) different illumination angles during the image acquisition phase. During this image acquisition phase, the optical switch 318 switches to the different optical fibers 301(1) through 301(37). By way of illustration, at the sampling time shown in FIG. 3, the optical switch 318 is switched to provide laser light to optical fiber 301(5) within fiber connector 303(5) located within optical port 303(5) to illuminate at the illumination angle depicted by the arrow. Once the sample has been illuminated at a particular illumination angle, e.g., for at least the exposure time, the optical switch 318 switches to a different optical fiber 301 to illuminate at a different illumination angle. This process of illumination and switching may continue until the sample has been illuminated at each of illumination angles at each of the different sampling times. The laser light source may be activated during the entire process or may be switched on at each exposure time during the process.

In FIG. 3, the optical ports 305(1) through 305(37) are shown as circular apertures. It would be understood that the optical ports have other shapes in other embodiments.

As shown in FIG. 3, each optical port 305 is configured along a fiber array dome 314 to position the respective optical fiber 301 in a particular direction. In order to approximate uniform illumination at each illumination angle, the fiber array dome 314 can be designed so that there is a uniform distance between each optical port 305 and the sample plane. In one embodiment, the fiber array dome 314 is hemisphere shaped with a constant radius so that there is a constant distance between each optical port 305 and the center of the circular surface at the surface of the hemisphere. The circular surface at the surface of the hemisphere is kept near the outer surface of the transparent layer 307 to approximate uniform illumination of the sample plane.

In certain implementations, the spacing between adjacent optical ports 305 and the direction of the optical ports 305 are configured so that the laser light directed by the optical ports 305 generates adjacent illumination angles with overlapping regions in Fourier space of at least a minimum amount (e.g. 60%, 65%, 70%, 80%, or 90%). The spacing between adjacent optical ports 305 and the size the fiber array dome 314 may vary across implementations. In one embodiment, the spacing between adjacent optical ports 305 may be uniform. In one particular implementation, the radius of the dome surface of the fiber array dome 314 along which each optical port 305 is positioned is approximately 8 mm. In this implementation, each optical port 303(i) may be spaced 1-5 cm apart. A closer spacing, e.g. 1 cm, and a wider radius may be used if the collection element 322 of the optical system 320, as discussed further below, has a relative low NA for wide field-of-view imaging. On the other hand, a larger spacing, e.g. 5 cm, may be used if the collection element 322 of the optical system 320 has a higher NA.

The optical switch 318 and/or other components of LFP system 300 may be controlled by control signals from a processor(s) (e.g. process of the controller 140 of FIG. 1). The processor(s) retrieves instructions stored in the CRM (e.g. internal memory 160 of FIG. 1) for performing various functions of the LFP system 300. For example, the processor(s) may be coupled with the optical switch 318 to send control signals to switch the laser light from the laser source(s) to a particular optical fiber 301 at a particular sampling time to direct the laser beam at one of the illumination angles. In some cases, the controller may also activate the laser light source(s). Alternatively, the optical switch 318 may have an internal memory and processor and may be programmed to cause the optical switch 318 to switch between optical fibers 301 at pre-determined times.

While the optical switch 318 is described as a single optical switch, an array of optical switches may be used in another implementation. In this case, an array of optical switches is connected in a cascading series to achieve N outputs. For example, each of the 16 outputs of a 1×16 19" 2 HU from Leoni Fiber Optics® may be connected with an input of another 1×16 19" 2 HU from Leoni Fiber Optics®. In such an arrangement, 256 outputs could be achieved. While such a series may be extended indefinitely (e.g. the output of one switch may be connected with the input of another switch, which may be connected with the input of yet another switch, etc.), each interface between switches introduces a certain amount of insertion loss/reflection. Accordingly, such a series of switches will cause some decrease in intensity of the laser light from the laser light source. Thus, in this scenario, the intensity of the laser light source should be adjusted accordingly. This insertion loss may be avoided by using a single optical switch with the appropriate number of outputs.

At the instant in time illustrated in FIG. 3 angle direction device 312 illuminates the specimen on specimen surface 308. The light incident on the specimen is scattered by the physical features of the specimen as it passes through the specimen. The collection element 322, which has a particular objective NA, receives light passing through the specimen. If an iris is included in optical system 320, it would be placed at the back focal plane of collection element 322. The iris receives light propagated by the collection element 322 and passes light incident on its pupil area. Light incident on the area of the iris around the pupil area is substantially blocked. The focusing element 324 receives the light passed by the iris and focuses the light to the light detector 332. The light detector 332 is configured to receive light focused by the focusing element 324 and acquire a sequence of intensity images of the sample when the sample is on the specimen surface 308 and while the optical switch 318 switches laser light between the different optical fibers 301 at the different sampling times.

During the high-resolution reconstruction phase, one or more processors of the LFP system 300 interpret and process the raw image data from the sequence of images acquired during the image acquisition phase to generate processed image data. The one or more processors interpret raw image data from the sequence of acquired intensity images, transform the relatively low-resolution raw image data frames into Fourier space, iteratively update the transformed raw image data in Fourier space to reconstruct amplitude and phase data for a single high-resolution image of the sample and the associated pupil function of the imaging system. In some cases, the one or more processors uses a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 in FIG. 1 to display data such as the high-resolution image and other data.

D. LFP Systems with a Rotatable Mirror and a Mirror Array

Certain implementations of an LFP imaging system include an angular direction device with a two-axis rotatable mirror and a mirror array (e.g., faceted bowl shaped mirror array). In these implementations, a collimated laser beam is directed to the reflective surface of the two-axis rotatable mirror system such as Galvo mirror. The two-axis rotatable mirror system rotates its one or more lenses to receive and reflect the laser beam to each of a plurality of mirror elements in the mirror array. The laser beam is reflected by each of the mirror elements to direct the laser beam at the illumination angles to the sample plane. Changing the tilt angle of the two-axis rotatable mirror system allows the laser beam to be incident on different mirror elements and provides for angularly varying illumination of the sample plane during the raw image acquisition process.

Figure 4:
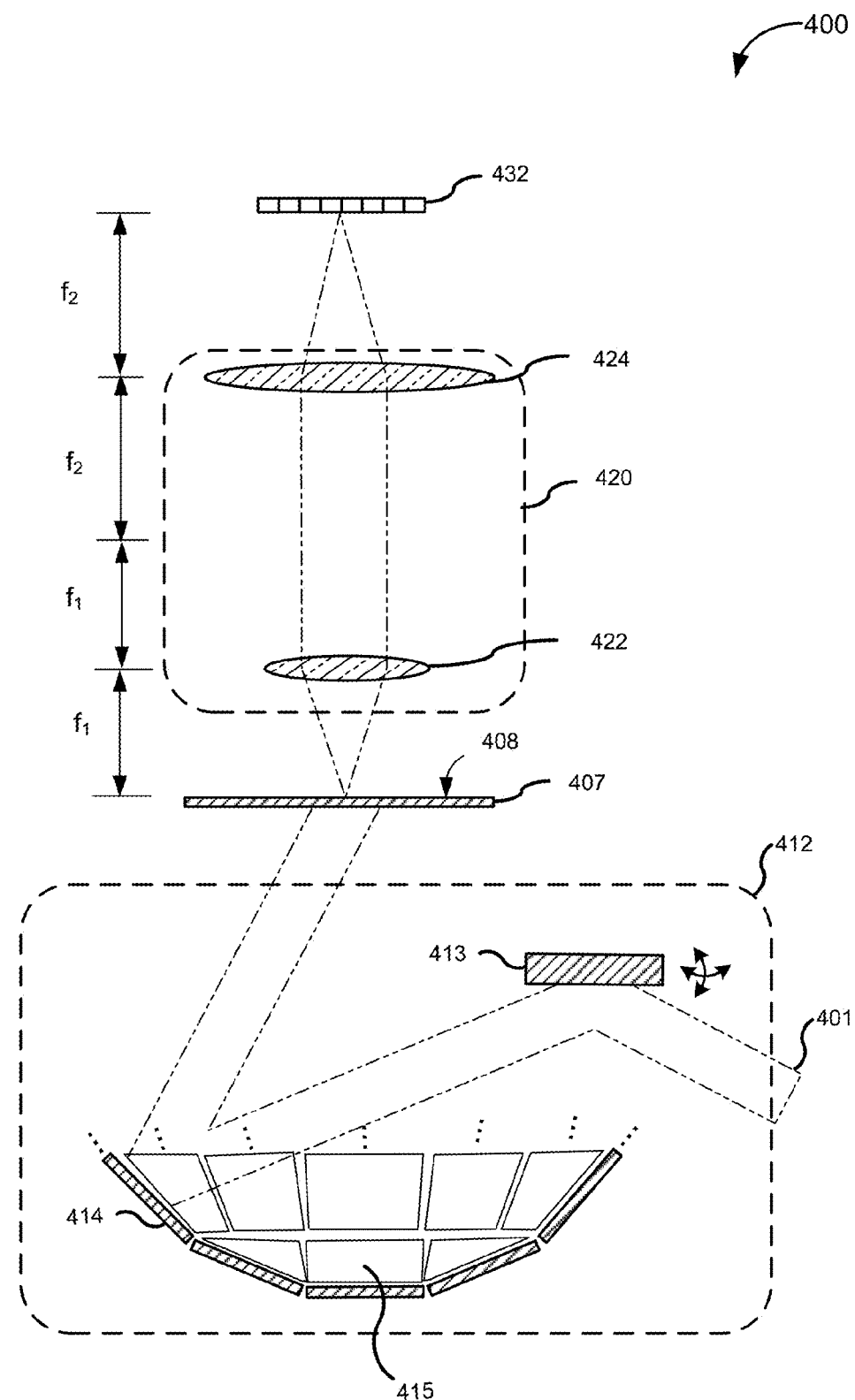
FIG. 4 shows a schematic drawing of a cut-away view of another example of an LFP imaging system, in accordance with some implementations.

FIG. 4 shows a schematic drawing of a cutaway view of an LFP imaging system imaging system 400 comprising an angle direction device 412 with a two-axis rotatable mirror 413 and a mirror array 414, in accordance with some implementations. In FIG. 4, a laser light source (not depicted) is activated and providing collimated laser light 404 to a two-axis rotatable mirror 413 of the angle direction device 412. A transparent layer 407 (e.g., slide) with a specimen surface 408 generally at the sample plane is also shown. The specimen surface 408 can receive a sample (not shown) to be imaged. One or more components of the angle direction device 412 may be separate from the LFP imaging system 400. The LFP imaging system 400 further comprises an optical system 420 and a light detector 432 for receiving light propagated by the optical system 420.

The LFP Imaging system 400 also includes an optical system 420 having a collection element 422 (e.g., lens) having a focal length, $f_1$, and a focusing element 424 (e.g., lens) having a focal length, $f_2$. The collection element has an objective NA and is configured to receive light issuing from a specimen when it is located on the specimen surface 407. The focusing element 424 is configured to focus light propagated from the collection element 422 to the light detector 432. The sequence of illumination angles and the objective NA correspond to overlapping regions in the Fourier domain, as described in further detail below. In the illustration, the optical system 420 is in a 4f arrangement where the collection element 422 is located so that the sample plane is f1 apart from it. The sample's Fourier plane is located f1 away on the other side of 422. Fourier plane of the sample at the sample plane at specimen surface 408 is a focal length, $f_2$, away from the focusing element 424 and the focusing element 424 is located a distance of a focal length, $f_2$, away from the light detector. 408 Other arrangements can be used. For example, a 6f arrangement can be used. As another example, other optical elements (e.g., mirrors) can be introduced into the optical path for other arrangements.

Angle direction device 412 includes a rotatable mirror 413 and a mirror array 414 having N mirrors 415. Rotatable mirror 413 may be configured or configurable to rotate along two axes to orient its reflective surface at different positions during the image acquisition phase in order to reflect laser light from the laser light source to each of the N mirrors 415 of the mirror array 414 at different sampling times. Each mirror 415 of the mirror array 414 is oriented such that it reflects laser light received from the rotatable mirror 413 to a sample plane at the specimen surface 408. During the image acquisition phase, the rotatable mirror 413 rotates to the different positions, in some cases holding at each position for at least an exposure time, to reflect laser light from the laser light source to different mirrors 415 of the mirror array 414 to reflect the laser light at the sequence of illumination angles described above in the context of FIG. 1. As such, the rotatable mirror 413 rotates such that collimated laser light 404 is reflected by the rotatable mirror 413 to the mirrors of the mirror array 414 to illuminate the specimen at different illumination angles at different sampling times. At the instant in time shown in the illustrated in FIG. 4, the rotatable mirror 413 is rotated to a particular position to cause the collimated laser light 404 to be directed to one mirror 415 of the mirror array 414 from which the collimated laser light 404 is reflected, illuminating the specimen at one of the illumination angles. Once the collimated laser light 404 has illuminated the specimen at the particular illumination angle, typically for at least an exposure time, the light detector 432 measures an intensity image and the rotatable mirror 413 is rotated to another position to cause the collimated laser light 404 to be directed to another mirror of the mirror array 414, illuminating the specimen from another one of the illumination angles and the light detector measures another intensity image. This process may continue until the specimen has been illuminated at each of the illumination angles at each of the different sampling times.

While a single two-axis rotatable mirror 413 is depicted in FIG. 4, two mirrors, each of which is rotatable about a single axis such as in a Galvo mirror system, may be used in another embodiment. An example of two mirrors that can be used in such an embodiments are the mirrors 613 and 614 discussed in greater detail below in the context of FIGS. 6 and 8.

The rotatable mirror 413 may be controlled in a variety of manners. By way of example, a controller, e.g. controller 140 of FIG. 1, may be coupled with the rotatable mirror 413 of FIG. 4. The controller may access instructions stored in a memory, e.g. internal memory 160 of FIG. 1. The instructions may be executable by the controller to cause the rotatable mirror 413 of FIG. 4 to or rotate to any given position such that the specimen is illuminated at each of the illumination angles at each of the different sampling times, as described in the preceding paragraph. Alternatively, the rotatable mirror 413 may have an internal memory and processor and may be programmed to cause the rotatable mirror 413 to follow a pre-determined rotation path.

The rotatable mirror 413 and/or other components of LFP system 400 may be controlled by a controller (e.g. controller 140 of FIG. 1) with a processor and a computer readable medium (CRM) in communication with the processor. The controller retrieves instructions stored in the CRM (e.g. internal memory 160 of FIG. 1) for performing various functions of the LFP system 400. For example, the controller may be coupled with the rotatable mirror 413 to send control signals to rotate the rotatable mirror 413 at a particular sampling time to direct the laser beam at one of the illumination angles. In some cases, the controller may also activate the laser light source(s). In one case, the laser light source(s) are turned on during the entire image acquisition phase. In another case, the laser light source(s) are activated to be turned on during at least the exposure time of each intensity image acquisition. Alternatively, the rotatable mirror 413 or other system components may have an internal memory and processor and may be programmed to cause rotatable mirror 413 to rotate at pre-determined times.

Optical system 420 may have some of the same or similar components and operate in the same or similar manner as optical systems 220 and 320 of FIGS. 3 and 4. Like in FIGS. 3 and 4, when the specimen on specimen surface 408 of FIG. 4 is illuminated at each of illumination angles at each of the different sampling times, some of the light illuminating the specimen is scattered by the specimen and passes through an optical system 420. Optical system 420 includes a collection element 422 and a focusing element 424.

In one embodiment, the LFP imaging system 300 also includes one or more processors and computer readable medium (CRM) (e.g., memory) in communication with the processor(s). The one or more processors and computer readable medium may be part of a controller such as the controller 140 described with respect to FIG. 1. The processor-executable code (or "instructions") for performing the LFP imaging method can be stored on the CRM or other memory. The processor(s) and can retrieve the processor-executable code from the CRM or other memory to perform various functions or operations of the LFP imaging method. The CRM or other memory can store raw and/or processed image data. In some implementations, the CRM or other memory can additionally or alternatively include a volatile memory array for temporarily storing code to be executed as well as image data to be processed, stored, or displayed.

At the instant in time illustrated in FIG. 4, angle direction device 412 illuminates the specimen on specimen surface 408. The light incident on the specimen is scattered by the physical features of the specimen as it passes through the specimen. The collection element 422, which has a particular objective NA, receives light issuing from the specimen being illuminated. If an iris is included in optical system 420, it would be placed at the backfocal plane of 422. The iris receives light propagated by the collection element 422 and passes light incident on its pupil area. Light incident on the area of the iris around the pupil area is substantially blocked. The focusing element 424 receive the light passed by the iris and focuses the light to the light detector 432.

Like in FIGS. 2-3, a light detector 432 of FIG. 4 receives light focused by the focusing element 424 and acquires a sequence of intensity images of the specimen when the specimen is illuminated sequentially by the plurality of illumination angles at the different sampling times.

During the high-resolution reconstruction phase, one or more processors of the LFP system 400 interpret and process the raw image data from the sequence of images acquired during the image acquisition phase to generate processed image data. The one or more processors interpret raw image data from the sequence of acquired intensity images, transform the relatively low-resolution raw image data frames into Fourier space, iteratively update the transformed raw image data in Fourier space to reconstruct amplitude and phase data for a single high-resolution image of the sample and the associated pupil function of the imaging system. In some cases, the one or more processors uses a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 in FIG. 1 to display data such as the high-resolution image and other data.

E. LFP Systems with a Rotatable Mirror and Lenses

Certain implementations of an LFP imaging system include an angular direction device with a rotatable mirror and lenses. In these implementations, a collimated laser beam is directed to the reflective surface of the two-axis rotatable mirror such as Galvo mirror. The two-axis rotatable mirror is placed at the focal plane of a first lens. The two-axis rotatable mirror is rotated to reflect the laser beam at different angles to the first lens. The laser beam reflected from the two-axis rotatable mirror is focused by the first lens on the first lens' back-focal plane, which coincides with the focal plane of a second lens. The laser beam exits the second lens as a collimated beam and shines on the sample plane at an illumination angle, which is proportional to the angle at which the laser beam is reflected off the rotatable mirror. In this way, the rotatable mirror can rotate (tilt) to direct the laser light at different illumination angles to the sample plane to illumination a sample to be imaged.

Figure 5:
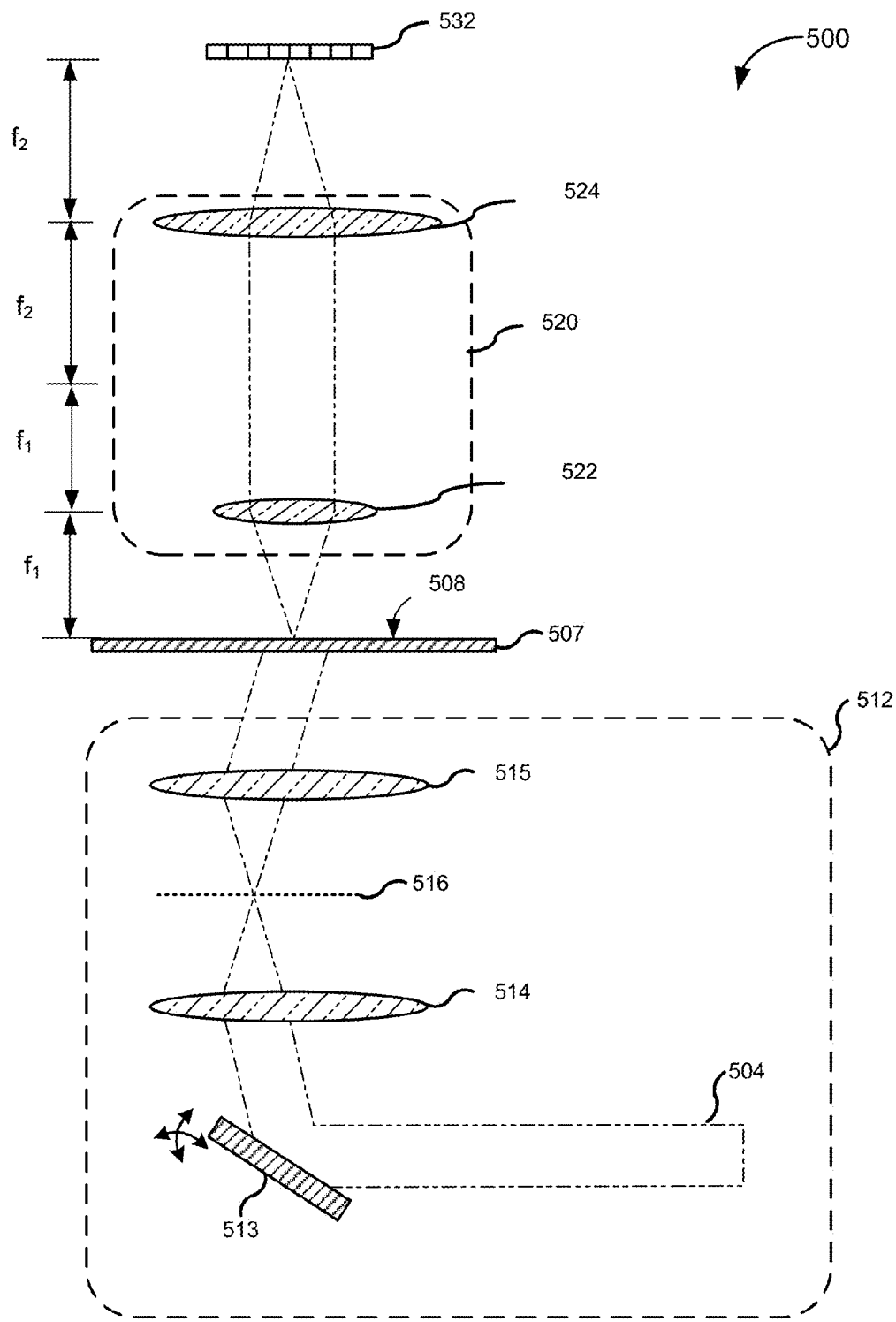
FIG. 5 shows a schematic drawing of a cut-away view of another example of an LFP imaging system, in accordance with some implementations.

FIG. 5 shows a schematic drawing of a side view of an example of an LFP imaging system 500 comprising an angular direction device 512 with a two-axis rotatable mirror 513 and a first lens 514 and a second lens 515, in accordance with some implementations. In FIG. 5, a laser light source (not depicted) is activated and providing collimated laser light 504 to a two-axis rotatable mirror 513 of the angle direction device 512. A transparent layer 507 (e.g., slide) with a specimen surface 508 is also shown. The specimen surface 508 can receive a sample (not shown) to be imaged. One or more components of the angle direction device 512 may be separate from the LFP imaging system 500.

The LFP Imaging system 500 also includes an optical system 520 having a collection element 522 (e.g., lens) having a focal length, $f_1$, and a focusing element 524 (e.g., lens) having a focal length, $f_2$. The collection element has an objective NA and is configured to receive light issuing from a specimen when it is located on the specimen surface 507. The focusing element 524 is configured to focus light propagated from the collection element 522 to the light detector 532. The sequence of illumination angles and the objective NA correspond to overlapping regions in the Fourier domain, as described in further detail below. In the illustration, the optical system 520 is in a 4f arrangement where the collection element 522 is located so that the sample plane is $f_1$ apart from it. The sample's Fourier plane is located $f_1$ away on the other side of collection element 522. Fourier plane of the sample at the sample plane at specimen surface 508 is a focal length, $f_2$, away from the focusing element 524 and the focusing element 524 is located a distance of a focal length, $f_2$, away from the light detector. Other arrangements can be used. For example, a 6f arrangement can be used. As another example, other optical elements (e.g., mirrors) can be introduced into the optical path for other arrangements.

Angle direction device 512 includes a rotatable mirror 513 and a lens system including a first lens 514 and a second lens 515. The rotatable mirror 513 propagates collimated laser light 504 to the specimen surface 508 via the lens system including first and second lenses 514 and 515. During an image acquisition phase, the rotatable mirror 513 is configured to rotate along two axes to direct collimated laser light 504 to the first lens 514 at a sequence of incidence angles. The first lens 514 focuses light 504. The first and second lenses 514 and 515 are positioned such that the focal plane 516 of the first lens 514 coincides with the back focal plane of the second lens 515. As such, the light 504 focused by the first lens 514 is unfocused by the second lens 515 back into a collimated beam. The rotatable mirror 513 is configured to rotate such that collimated laser light 504 is refracted by the first and second lenses 514 and 515 to illuminate the specimen with a collimated beam at each illumination angle of a sequence of illumination angles, as described above in the context of FIG. 1. By way of illustration, at the instant in time shown in FIG. 5, the rotatable mirror 513 is rotated to a particular position to cause the collimated laser light 504 to be refracted by the lenses 514 and 515, illuminating the specimen at one of the illumination angles. While the collimated laser light 504 illuminates the specimen at the particular illumination angle, e.g., for at least the exposure time, the light detector 532 measures an intensity image. Once the intensity image is acquired, the rotatable mirror 513 may be rotated to another position to acquire another intensity image. When the rotatable mirror 513 is in the other position it causes the collimated laser light 504 to be refracted at a different angle by the lenses 514 and 515, illuminating the specimen at a different one of the illumination angles and the light detector 532 acquires another intensity image. This process may continue until the specimen has been illuminated at each of illumination angles at each of the different sampling times and the light detector 532 acquires a sequence of intensity images.

In one embodiment, the LFP imaging system 500 also includes one or more processors and computer readable medium (CRM) (e.g., memory) in communication with the processor(s). The one or more processors and computer readable medium may be part of a controller such as the controller 140 described with respect to FIG. 1. The processor-executable code (or "instructions") for performing the LFP imaging method can be stored on the CRM or other memory. The processor(s) and can retrieve the processor-executable code from the CRM or other memory to perform various functions or operations of the LFP imaging method. The CRM or other memory can store raw and/or processed image data. In some implementations, the CRM or other memory can additionally or alternatively include a volatile memory array for temporarily storing code to be executed as well as image data to be processed, stored, or displayed.

In addition to mitigating aberrations from speckles in image due to the use of laser light, other mitigation measures may be taken to account for other aberrations in the LFP systems according to certain embodiments. For example, mitigation measures may be taken into account for aberration introduced when collimated laser light 504 enters the lenses 514 and 515 in different places. For example, in some implementations, the lenses 514 and 515 are both F-theta lenses rather than conventional spherical lenses to reduce spherical aberration. Examples of F-theta lenses are commercially available such as an F-theta lens produced by Thor Labs®.

The rotatable mirror 513 may be controlled in a variety of manners. By way of example, a processor (e.g., processor of controller 140 of FIG. 1) may be in communication with the rotatable mirror 513 of FIG. 5. The processor may access instructions stored in a memory, e.g. internal memory 160 of FIG. 1. The instructions may be executable by the processor to cause the rotatable mirror 513 of FIG. 5 to rotate to any given position such that the specimen is illuminated at each of the illumination angles at each of the different sampling times. Alternatively, the rotatable mirror 513 may have an internal memory and processor and may be programmed to cause the rotatable mirror 513 to follow a pre-determined rotation path.

Generally, the rotatable mirror 513 and/or other components of LFP system 500 may be controlled with control signals sent by a processor(s) (e.g. processor of controller 140 of FIG. 1). The processor retrieves instructions stored in a computer readable medium (CRM) (e.g. internal memory 160 of FIG. 1) for performing various functions of the LFP system 500. For example, the controller may be coupled with the rotatable mirror 513 to send control signals to rotate the rotatable mirror 513 at a particular sampling time to direct the laser beam at one of the illumination angles. In some cases, the controller may also activate the laser light source(s). In one case, the laser light source(s) are turned on during the entire image acquisition phase. In another case, the laser light source(s) are activated to be turned on during at least the exposure time of each intensity image acquisition. Alternatively, the rotatable mirror 513 may have internal memory and processor and may be programmed to cause rotatable mirror 513 to rotate at pre-determined times and/or other system components may have internal memory and processor and may be programmed in its operations.

While a single two-axis rotatable mirror 513 is depicted in FIG. 5, two mirrors, each of which is rotatable about a single axis, may be used in another embodiment. An example of two mirrors that can be used in such an embodiments are the mirrors 613 and 614 and 813 and 814 discussed in greater detail below in the context of FIGS. 6 and 8.

Optical system 520 may have the same or similar elements and operate in the same or similar manner as optical systems 220, 320 and 420 of FIGS. 3, 4, and 5. Like in FIGS. 3, 4, and 5, when the specimen on specimen surface 508 of FIG. 5 is illuminated at each of illumination angles at each of the different sampling times, some of the light illuminating the specimen is scattered by the specimen and passes through an optical system 520. Optical system 520 includes a collection element 522 and a focusing element 524.

At the instant in time illustrated in FIG. 5 angle direction device 512 illuminates the specimen on specimen surface 508. The light incident on the specimen is scattered by the physical features of the specimen as it passes through the specimen. The collection element 522, which has a particular objective NA, receive light passing through the specimen. If an iris is included in optical system 520, it would be placed at the back focal plane of collection element 522. The iris receives light propagated by the collection element 522 and passes light incident on its pupil area. Light incident on the area of the iris around the pupil area is substantially blocked. The focusing element 524 receives the light passed by the iris and focuses the light to the light detector 532.

Like in FIGS. 2-4, a light detector 532 of FIG. 5 receives light focused by the focusing element 524 and acquires a sequence of intensity images of the specimen when the specimen is illuminated sequentially by the plurality of illumination angles at the different sampling times.

During the high-resolution reconstruction phase, one or more processors of the LFP system 500 interpret and process the raw image data from the sequence of images acquired during the image acquisition phase to generate processed image data. The one or more processors interpret raw image data from the sequence of acquired intensity images, transform the relatively low-resolution raw image data frames into Fourier space, iteratively update the transformed raw image data in Fourier space to reconstruct amplitude and phase data for a single high-resolution image of the sample and the associated pupil function of the imaging system. In some cases, the one or more processors uses a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 in FIG. 1 to display data such as the high-resolution image and other data.

F. LFP Systems with a Circular Mirror Array on Flat Surface

Certain implementations of an LFP imaging system include an angular direction device with a two-axis rotatable mirror system such as a Galvo mirror system and a circular array of mirrors (mirror array) arranged on a flat surface. For example, the mirror array may be an arrangement of mirrors in concentric circles along a flat surface. In these implementations, a collimated laser beam is directed to the reflective surface of the two-axis rotatable mirror. The two-axis rotatable mirror system rotates its one or more mirrors to receive and reflect the laser beam to each of a plurality of mirror elements in the mirror array. The laser beam is reflected by each of the mirror elements to direct the laser beam at the illumination angles to the sample plane. Changing the tilt angle of the two-axis rotatable mirror system allows the laser beam to be incident on different mirror elements and provides for angularly varying illumination of the sample plane during the raw image acquisition process.

Figure 6:
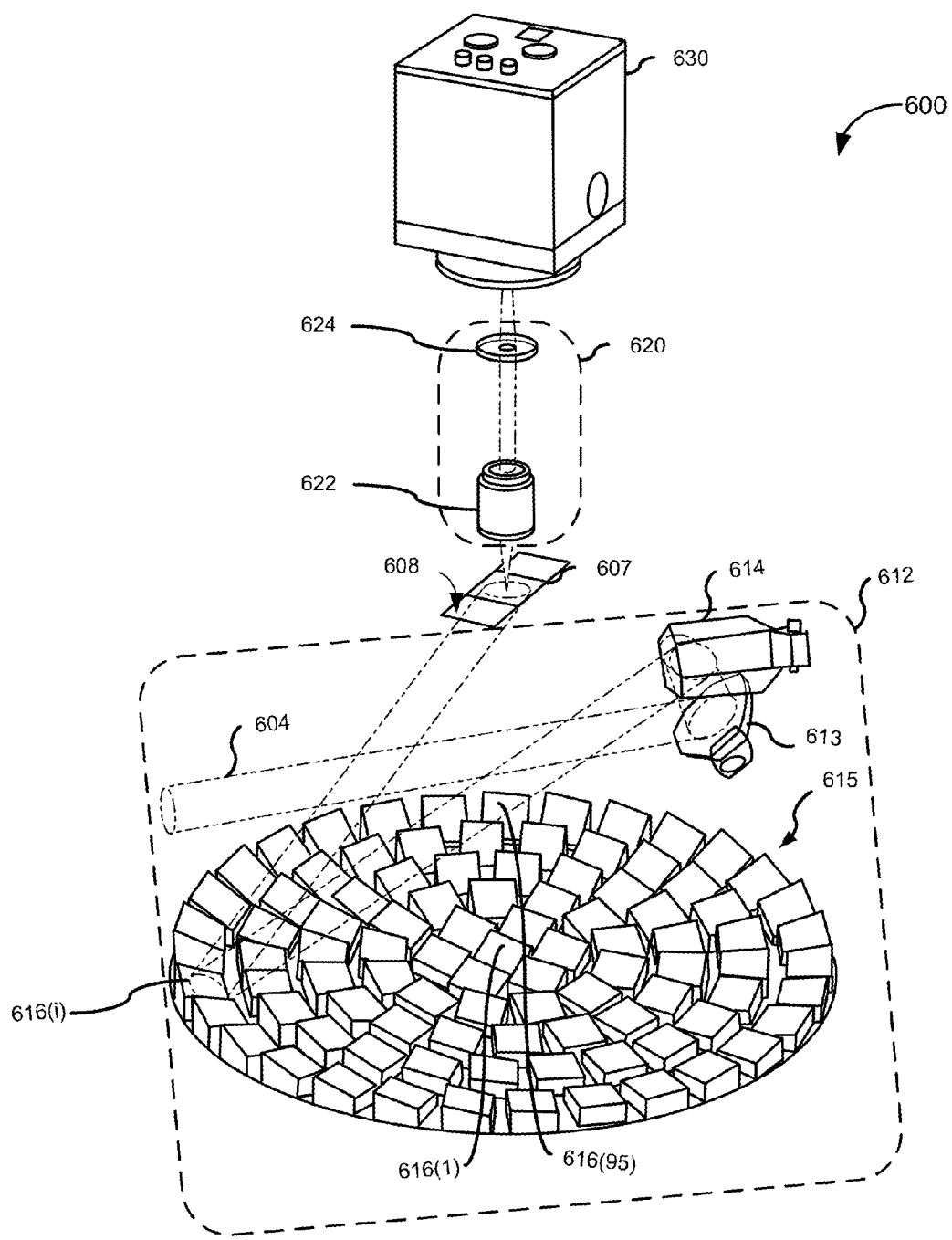
FIG. 6 shows a schematic drawing of an orthogonal view of another example of an LFP imaging system, in accordance with some implementations.

FIG. 6 shows a schematic drawing of an orthogonal view of an LFP imaging system imaging system 600 with a circular mirror array 615 on a flat surface, in accordance with some implementations. A transparent layer 607 (e.g., slide) with a specimen surface 608 generally at the sample plane is also shown. The specimen surface 608 can receive a sample (not shown) to be imaged.

The LFP imaging system imaging system 600 comprises an angle direction device 612 with a first rotatable mirror 613 and second rotatable mirror 614, and a circular mirror array 615 having ninety five (95) mirrors 616(1)-616(95). More or fewer mirrors 616 may be used. One or more components of the angle direction device 612 may be separate from the LFP imaging system 600. The LFP imaging system 600 further comprises an optical system 620 and an image sensor system 630 with one or more light detectors for receiving light propagated by the optical system 620.

The optical system 620 comprises a collection element 622 (e.g., lens) having a focal length, $f_1$, and a focusing element 624 (e.g., lens) having a focal length, $f_2$. The collection element has an objective NA and is configured to receive light issuing from a specimen when it is located on the specimen surface. The focusing element 624 is configured to focus light propagated from the collection element 622 to the light detector of the image sensor system 630. The sequence of illumination angles and the objective NA correspond to overlapping regions in the Fourier domain, as described in further detail below. In the illustration, the optical system 620 is in a 4f arrangement where the collection element 622 is located so that the sample plane is f1 apart from it. The sample's Fourier plane is located f1 away on the other side of 622. Fourier plane of the sample at the sample plane at specimen surface 608 is a focal length, $f_2$, away from the focusing element 624 and the focusing element 624 is located a distance of a focal length, $f_2$, away from the light detector. 608 Other arrangements can be used. For example, a 6f arrangement can be used. As another example, other optical elements (e.g., mirrors) can be introduced into the optical path for other arrangements.

Angle direction device 612 includes first and second rotatable mirrors 613 and 614 and a circular mirror array 615 having ninety five (95) mirrors 616(1)-616(95). First and second rotatable mirrors 613 and 614 may rotate each rotate about a different axis such that they are configured to be rotated to reflect laser light from the laser light source to each of the ninety five (95) mirrors 616(1)-616(95). The first rotatable mirror 613 is configured to reflect collimated laser light 604 from the laser light source (not shown) to the second rotatable mirror 614. The second rotatable mirror 614 is configured to reflect to reflect the collimated laser light 604 from the first rotatable mirror 613 to one of the mirrors 616(1)-616(95). Each of the mirror 616(1)-616(95) in the mirror array 615 may be oriented such that it reflects laser light received from the second rotatable mirrors 614 to the sample plane at one of the illumination angles in a sequence of illumination angles, as described above in the context of FIG. 1. As such, the first and second rotatable mirrors 613 and 614 are configured to rotate such that collimated laser light 604 may be reflected by the first and second rotatable mirrors 613 and 614 and directed to the mirrors 616(1)-616(95) to illuminate the specimen at each illumination angles in the sequence of illumination angles. By way of illustration, at a particular sampling time, the first and second rotatable mirrors 613 and 614 may be rotated to particular orientations to cause the collimated laser light 604 to be directed to a particular mirror 616(i) of the circular mirror array 615 from which the collimated laser light 604 is reflected, illuminating the specimen at a particular one of the illumination angles. While the collimated laser light 604 illuminates the sample plane at a particular illumination angle, e.g., for at least an exposure time, a light detector(s) of the image sensor system 630 acquires an intensity image and then the rotatable mirrors 613 and 614 may be rotated to cause the collimated laser light 604 to be directed to another mirror 616(i+1), illuminating the specimen from another one of the illumination angles so that the light detector may generate another intensity image. This process may continue until the specimen has been illuminated at each of illumination angles at each of the different sampling times.

At the instant in time depicted in FIG. 6, a laser light source (not depicted) is activated and providing collimated laser light 604 to the first rotatable mirror 613 of the angle direction device 612. The first rotatable mirror 613 is oriented to reflect collimated laser light 604 to the second rotatable mirror 614 which reflects the collimated laser light 604 to a particular mirror 616(i) of the circular mirror array 615 from which the collimated laser light 604 is reflected to the specimen plane which is approximately at the specimen surface 608.

In one embodiment, the LFP imaging system 600 also includes one or more processors and computer readable medium (CRM) (e.g., memory) in communication with the processor(s). The one or more processors and computer readable medium may be part of a controller such as the controller 140 described with respect to FIG. 1. The processor-executable code (or "instructions") for performing the LFP imaging method can be stored on the CRM or other memory. The processor(s) and can retrieve the processor-executable code from the CRM or other memory to perform various functions or operations of the LFP imaging method. The CRM or other memory can store raw and/or processed image data. In some implementations, the CRM or other memory can additionally or alternatively include a volatile memory array for temporarily storing code to be executed as well as image data to be processed, stored, or displayed.

Although the mirror array 615 is illustrated with ninety five (95) mirrors 616, other numbers of mirrors can be used in the mirror array 615. Each mirror 616(i) of the mirror array 615 is coupled at one end of a rectangular tower coupled to a plate. In one embodiment, the rectangular towers are 3D-printed structures. Each tower's top surface is sloped at a certain angle such that collimated laser light 604 may be reflected towards the sample plane at one of the illumination angles in the sequence of illumination angles described above.

Figure 7A:
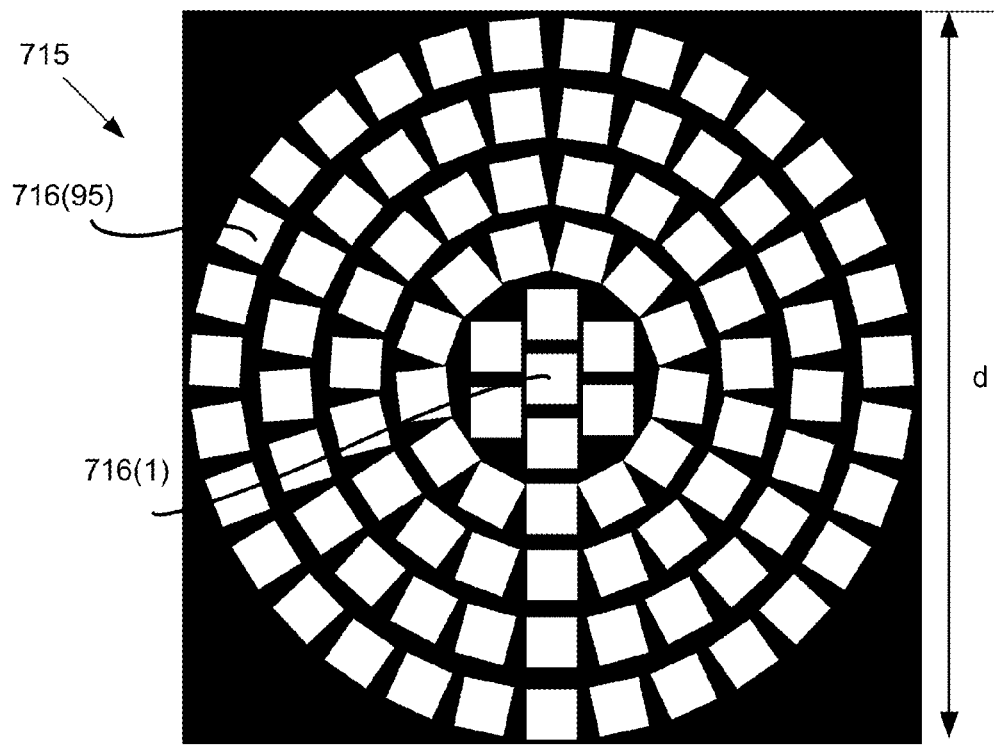
FIG. 7A shows a schematic layout of an example of a mirror array, in accordance with some implementations.
Figure 7B:
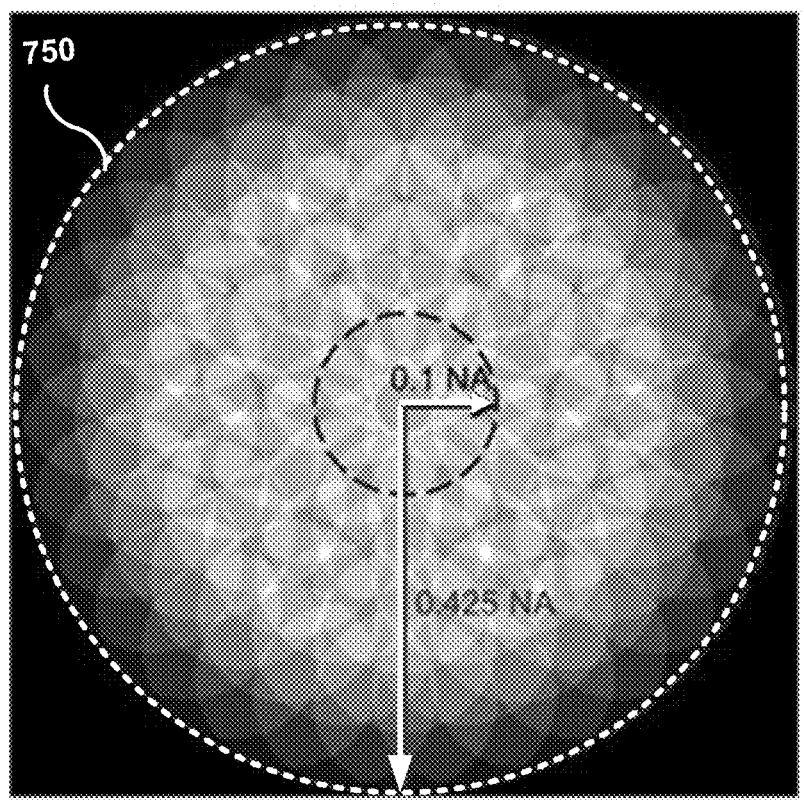
FIG. 7B shows a schematic layout of an example of a region in Fourier space that corresponds to the mirror array of FIG. 7A, in accordance with some implementations.

FIG. 7A is a plan view of a mirror array 715 with a similar configuration the mirror array 615 shown in FIG. 6, according to an embodiment. The mirror array 715 has a diameter, d. FIG. 7B is an illustration of the Fourier spectrum region 750 covered by the angular varying illumination of the mirror array 715 shown in FIG. 7A. As shown by FIG. 7B, the mirrors 616(1)-616(95) are arranged to provide illumination to the sample plane such that contiguous regions produce 60% overlap of the specimen's spectrum in the Fourier domain, as shown in FIG. 7B. As discussed above, other embodiments may have a greater overlap, for example, at least 70%, at least 80%, etc.

In some implementations, a neutral density filter is placed on each of the mirrors 616(1)-616(95) in the mirror array 615. Use of such neutral density filters allows for increasing the input laser intensity to obtain higher SNR in dark field images while preventing the bright field images from over-exposure.

The first and second rotatable mirrors 613 and 614 may be controlled in a variety of manners. By way of example, a controller, e.g. controller 140 of FIG. 1, may be coupled with the first and second rotatable mirrors 613 and 614 of FIG. 6. The controller may access instructions stored in a memory, e.g. internal memory 160 of FIG. 1. The instructions may be executable by the controller to cause the first and second rotatable mirrors 613 and 614 of FIG. 6 to or rotate to any given position such that the specimen is illuminated at each of the illumination angles at each of the different sampling times, as described in the preceding paragraph. Alternatively, the first and second rotatable mirrors 613 and 614 may have an internal memory and processor and may be programmed to cause each of the first and second rotatable mirrors 613 and 614 to follow a pre-determined rotation path.

The first and second rotatable mirrors 613 and 614 and/or other components of LFP system 600 may be controlled by control signals from a processor(s) (e.g., a processor of the controller 140 of FIG. 1). The processor(s) retrieves instructions stored in a computer readable medium (CRM) (e.g. internal memory 160 of FIG. 1) for performing various functions of the LFP system 400. For example, the processor(s) may be coupled with the first and second rotatable mirrors 613 and 614 to send control signals to rotate the first and second rotatable mirrors 613 and 614 at particular sampling times to direct the laser beam to the different illumination angles. In some cases, the processor(s) may also send control signals to activate the laser light source(s). In one case, the laser light source(s) are turned on during the entire image acquisition phase. In another case, the laser light source(s) are activated to be turned on during at least the exposure time of each intensity image acquisition. Alternatively, the first and second rotatable mirrors 613 and 614 may have an internal memory and processor and may be programmed to cause first and second rotatable mirrors 613 and 614 to rotate at pre-determined times. Also, other system components may have an internal memory and a processor and may be programmed in its operations.

While two rotatable mirrors 613 and 614 are depicted in FIG. 6, a single mirror rotatable about two different axes can be used in another embodiment. Such a configuration of a single mirror is discussed in greater detail above in the context of FIGS. 4 and 5.

Optical system 620 may have the same or similar elements and operate in the same or similar manner as optical systems 220, 320, 420 and 520 of FIGS. 3, 4, 5 and 6. Like in FIGS. 3, 4, 5 and 6, when the specimen on specimen surface 605 of FIG. 6 is illuminated at each of illumination angles at each of the different sampling times, some of the light illuminating the specimen is scattered by the specimen and passes through an optical system 620. Optical system 620 includes a collection element 622 and a focusing element 624.

At the instant in time illustrated in FIG. 6, angle direction device 602 illuminates the specimen on specimen surface 605. The light incident on the specimen is scattered by the physical features of the specimen as it passes through the specimen. The collection element 622, which has a particular objective NA, receives light passing through the specimen. If an iris is included in optical system 620, it would be placed at the back focal plane of collection element 622. The iris receives light propagated by the collection element 622 and passes light incident on its pupil area. Light incident on the area of the iris around the pupil area is substantially blocked. The focusing element 624 receives the light passed by the iris and focuses the light to the light detector 630.

A light detector of the image sensor system 630 of FIG. 6 receives light focused by the focusing element 624 and acquires an intensity image of the specimen when the specimen is illuminated at each of the illumination angles at each of the different sampling times. During the high-resolution reconstruction phase, one or more processors of the LFP system 600 interpret and process the raw image data from the sequence of images acquired during the image acquisition phase to generate processed image data. The one or more processors interpret raw image data from the sequence of acquired intensity images, transform the relatively low-resolution raw image data frames into Fourier space, iteratively update the transformed raw image data in Fourier space to reconstruct amplitude and phase data for a single high-resolution image of the sample and the associated pupil function of the imaging system. In some cases, the one or more processors uses a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 in FIG. 1 to display data such as the high-resolution image and other data.

1) Example of an LFP Imaging System with Circular Mirror Array on a Flat Surface The dimensions and/or types of components of LFP Imaging systems disclosed herein may vary across implementations depending on the desired resolution of reconstructed images generated by the system, the field of view of view and/or NA of optical systems used in the LFP Imaging system, types of specimens being imaged by the LFP Imaging system, and other system parameters.

One particular implementation of an LFP Imaging system with a circular array on a flat surface has components similar to those described with respect to FIG. 6 and FIG. 7A. In this particular implementation, the optical system is a 4f system with collection element being a 0.1 NA Olympus® 4× objective lens and focusing element being a Thorlabs®

200-mm-focal-length tube lens. The light detector is a PCO.edge® 5.5 16 bit sCMOS sensor. The sensor has a pixel size of 6.5 mm and a maximum frame-rate of 100 Hz at 1920×1080 pixel resolution for a global shutter mode. In this implementation, the sensor size limits the available field of view of a specimen to be 2.7 mm by 1.5 mm. In this implementation, the laser light source is a 457 nm 1 W laser beam, which is pinhole-filtered and collimated, using standard collimation techniques. After collimation, the collimated laser light is 1 cm in diameter and has a 150 mW in power. Since the beam diameter the collimated laser light 1 cm, the collimated laser light covers the entire field of view captured by the light detector (2.7 mm by 1.5 mm after magnification).

In this particular implementation, the circular mirror array of mirrors has a height h of 30 cm. The mirrors are placed 40 cm away from the plane of the specimen surface. Rotatable mirror, which is a 2D Galvo mirror device (GVS 212), guides collimated laser light such that the central part of its Gaussian profile (approximately 40% of total output area) is incident on the input of the rotatable mirror, which is also 2D Galvo mirror device (GVS 212). Rotatable mirror then guides collimated laser light to individual mirrors. Each mirror is a 19 mm×19 mm first surface mirror attached to a 3D-printed rectangular tower. Each tower's top surface is sloped at a certain angle such that collimated laser light may be reflected towards the specimen surface at one of the illumination angles in the sequence of illumination angles described above.

The mirrors of the mirror array are arranged to provide illumination to a sample plane such that contiguous elements produce 60% overlap of the specimen's spectrum in the Fourier domain. In this implementation, the total illumination ($NA_{ti}$) is 0.325 with the resulting system NA ($NA_{sys}$) being $NA_{obj}+NA_{ti}=0.1+0.325=0.425$. In this particular implementation, the image reconstruction effectively increases the NA of the optical system by a factor of 4.25.

In this particular implementation, to achieve the maximum frame rate of the sCMOS sensor in light detector, the exposure time is set to its minimum, at 500 microseconds. The light detector and rotatable mirrors and are externally triggered every 10 milliseconds, resulting in 0.96 seconds of total capturing time for 95 intensity images (1 for each illumination angle) and 1 dark noise image.

G. LFP Systems with a Rectangular Mirror Array on Flat Surface

Certain implementations of an LFP imaging system include an angular direction device with a two-axis rotatable mirror system such as a Galvo mirror system and a rectangular array of mirrors (mirror array) arranged on a flat surface. For example, the mirror array may be an arrangement of mirrors in a rectangular array along a flat surface. In these implementations, a collimated laser beam is directed to the reflective surface of the two-axis rotatable mirror. The two-axis rotatable mirror system rotates its one or more lenses to receive and reflect the laser beam to each of a plurality of mirror elements in the mirror array. The laser beam is reflected by each of the mirror elements to direct the laser beam at the illumination angles to the sample plane. Changing the tilt angle of the two-axis rotatable mirror system allows the laser beam to be incident on different mirror elements and provides for angularly varying illumination of the sample plane during the raw image acquisition process.

Figure 8:
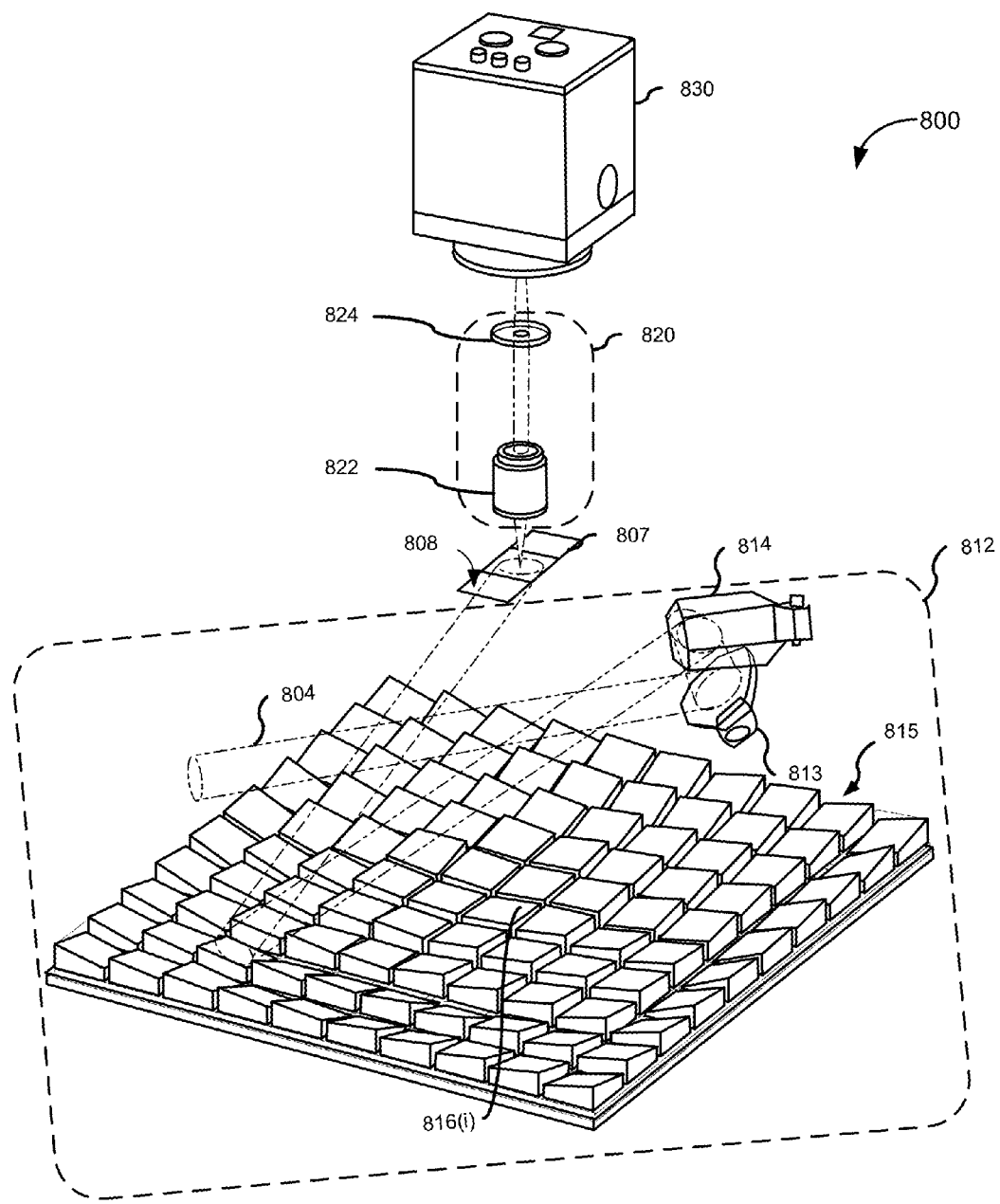
FIG. 8 shows a schematic drawing of an orthogonal view of another example of an LFP imaging system, in accordance with some implementations.

FIG. 8 shows a schematic drawing of an orthogonal view of an LFP imaging system imaging system 800 with a rectangular mirror array 815 on a flat surface, in accordance with some implementations. The LFP imaging system imaging system 800 comprises an angle direction device 812 with a first rotatable mirror 813 and second rotatable mirror 814, and a rectangular mirror array 815 having a hundred (100) mirrors 804(1)-804(100). In FIG. 8, a laser light source (not depicted) is activated and providing collimated laser light 804 to an angle direction device 812. A transparent layer 807 (e.g., slide) with a specimen surface generally at the sample plane is also shown. The specimen surface can receive a sample (not shown) to be imaged. One or more components of the angle direction device 812 may be separate from the LFP imaging system 800. The LFP imaging system 800 further comprises an optical system 820 and an image sensor system 830 with one or more light detectors for receiving light propagated by the optical system 820.

The LFP Imaging system 800 also includes an optical system 820 having a collection element 822 (e.g., lens) having a focal length, $f_1$, and a focusing element 824 (e.g., lens) having a focal length, $f_2$. The collection element has an objective NA and is configured to receive light issuing from a specimen when it is located on the specimen surface. The focusing element 824 is configured to focus light propagated from the collection element 822 to the light detector of the image sensor system 830. The sequence of illumination angles and the objective NA correspond to overlapping regions in the Fourier domain, as described in further detail below. In the illustration, the optical system 820 is in a 4f arrangement where the collection element 822 is located so that the sample plane is $f_1$ apart from it. The sample's Fourier plane is located $f_1$ away on the other side of the collection element 822. Fourier plane of the sample at the sample plane at specimen surface 808 is a focal length, $f_2$, away from the focusing element 824 and the focusing element 824 is located a distance of a focal length, $f_2$, away from the light detector. Other arrangements can be used. For example, a 6f arrangement can be used. As another example, other optical elements (e.g., mirrors) can be introduced into the optical path for other arrangements.

The angle direction device 812 includes first and second rotatable mirrors 613 and 814 and a rectangular mirror array 815 having a hundred (100) mirrors 804(1)-804(100). First and second rotatable mirrors 813 and 814 may rotate each rotate about a different axis such that they are configured to be rotated to reflect laser light from the laser light source to each of the hundred (100) mirrors 804(1)-804(100). By way of illustration, the first rotatable mirror 813 may reflect collimated laser light 804 from the laser light source (not shown) to the second rotatable mirror 814. The second rotatable mirror 814 may then reflect the collimated laser light 804 from the first rotatable mirror 813 to any of the mirrors 816(1)-816(100). Each of the mirror 816(1)-816 (100) in the mirror array 815 may be oriented such that it reflects laser light received from the first and second rotatable mirrors 813 and 814 to the sample plane at one of the illumination angles in a sequence of illumination angles, as described above in the context of FIG. 1. As such, the first and second rotatable mirrors 813 and 814 may be configured to rotate such that collimated laser light 804 may be reflected by the first and second rotatable mirrors 813 and 814 and directed to the mirrors 816(1)-816(100) to illuminate the specimen at each illumination angles in the sequence of illumination angles. By way of illustration, at a particular sampling time, the first and second rotatable mirrors 813 and 814 may be rotated to a particular position to cause the collimated laser light 804 to be directed to a particular mirror 816(i) of the rectangular mirror array 815 from which the collimated laser light 804 is reflected, illuminating the specimen at a particular one of the illumination angles. Once the collimated laser light 804 has illuminated the specimen at the particular illumination angle, e.g., for at least an exposure time, a light detector of the image sensor system 630 acquires an intensity image and the rotatable mirrors 813 and 814 may be rotated to another position to cause the collimated laser light 804 to be directed to another mirror 816($i$+1), illuminating the specimen from another one of the illumination angles so that the light detector may generate another intensity image. This process may continue until the specimen has been illuminated at each of illumination angles at each of the different sampling times.

In one embodiment, the LFP imaging system 800 also includes one or more processors and computer readable medium (CRM) (e.g., memory) in communication with the processor(s). The one or more processors and computer readable medium may be part of a controller such as the controller 140 described with respect to FIG. 1. The processor-executable code (or "instructions") for performing the LFP imaging method can be stored on the CRM or other memory. The processor(s) and can retrieve the processor-executable code from the CRM or other memory to perform various functions or operations of the LFP imaging method. The CRM or other memory can store raw and/or processed image data. In some implementations, the CRM or other memory can additionally or alternatively include a volatile memory array for temporarily storing code to be executed as well as image data to be processed, stored, or displayed.

Although the mirror array 815 is illustrated with one hundred (100) mirrors 816, other numbers of mirrors can be used in the mirror array 815. Each mirror 816($i$) of the mirror array 815 comprises a surface mirror affixed at one end of a rectangular tower. In one embodiment, the rectangular towers are 3D-printed structures. Each tower's top surface is sloped at a certain angle such that collimated laser light 804 may be reflected towards the sample plane at one of the illumination angles in the sequence of illumination angles described above.

In some implementations, a neutral density filter is placed on each of the mirrors 816(1)-816(100) in the mirror array 815. Use of such neutral density filters allows for increasing the input laser intensity to obtain higher SNR in dark field images while preventing the bright field images from overexposure.

The first and second rotatable mirrors 813 and 814 may be controlled in a variety of manners. By way of example, a controller, e.g. controller 140 of FIG. 1, may be coupled with the first and second rotatable mirrors 813 and 814 of FIG. 6. The controller may access instructions stored in a memory, e.g. internal memory 160 of FIG. 1. The instructions may be executable by the controller to cause the first and second rotatable mirrors 813 and 814 of FIG. 6 to or rotate to any given position such that the specimen is illuminated at each of the illumination angles at each of the different sampling times, as described in the preceding paragraph. Alternatively, the first and second rotatable mirrors 813 and 814 may have an internal memory and processor and may be programmed to cause each of the first and second rotatable mirrors 813 and 814 to follow a pre-determined rotation path.

The first and second rotatable mirrors 813 and 814 and/or other components of LFP system 800 may be controlled by a controller (e.g. controller 140 of FIG. 1) with a processor and a computer readable medium (CRM) in communication with the processor. The controller retrieves instructions stored in the CRM (e.g. internal memory 160 of FIG. 1) for performing various functions of the LFP system 400. For example, the controller may be coupled with the first and second rotatable mirrors 813 and 814 to send control signals to rotate the first and second rotatable mirrors 813 and 814 at a particular sampling time to direct the laser beam at one of the illumination angles. In some cases, the controller may also activate the laser light source(s). In one case, the laser light source(s) are turned on during the entire image acquisition phase. In another case, the laser light source(s) are activated to be turned on during at least the exposure time of each intensity image acquisition. Alternatively, the first and second rotatable mirrors 813 and 814 or other system components may have an internal memory and processor and may be programmed to cause first and second rotatable mirrors 813 and 814 to rotate at pre-determined times.

While two rotatable mirrors 813 and 814 are depicted in FIG. 6, a single mirror rotatable about two different axes can be used in another embodiment. Such a configuration of a single mirror is discussed in greater detail above in the context of FIGS. 4 and 5.

Optical system 820 may have the same or similar elements and operate in the same or similar manner as optical systems 220, 320, 420 and 520 of FIGS. 3, 4, 5 and 6. Like in FIGS. 3, 4, 5 and 6, when the specimen on specimen surface 605 of FIG. 6 is illuminated at each of illumination angles at each of the different sampling times, some of the light illuminating the specimen is scattered by the specimen and passes through an optical system 820. Optical system 820 includes a collection element 822 and a focusing element 824.

At the instant in time illustrated in FIG. 6 angle direction device 802 illuminates the specimen on specimen surface 805. The light incident on the specimen is scattered by the physical features of the specimen as it passes through the specimen. The collection element 822, which has a particular objective NA, receives light passing through the specimen. If an iris is included in optical system 820, it would be placed at the back focal plane of 822. The iris receives light propagated by the collection element 822 and passes light incident on its pupil area. Light incident on the area of the iris around the pupil area is substantially blocked. The focusing element 824 receives the light passed by the iris and focuses the light to the light detector of imaging system 830.

A light detector of the image sensor system 830 of FIG. 8 receives light focused by the focusing element 824 and acquires an intensity image of the specimen when the specimen is illuminated at each of the illumination angles at each of the different sampling times. During the high-resolution reconstruction phase, one or more processors of the LFP system 800 interpret and process the raw image data from the sequence of images acquired during the image acquisition phase to generate processed image data. The one or more processors interpret raw image data from the sequence of acquired intensity images, transform the relatively low-resolution raw image data frames into Fourier space, iteratively update the transformed raw image data in Fourier space to reconstruct amplitude and phase data for a single high-resolution image of the sample and the associated pupil function of the imaging system. In some cases, the one or more processors uses a differential phase contrast (DPC) deconvolution procedure to acquire the quantitative phase of the sample and use the phase data to correct for noise in the captured images such as those caused by speckles that may be caused by laser light illumination. During the optional display phase, display data is sent to a display such as display 152 in FIG. 1 to display data such as the high-resolution image and other data.

Figure 9A:
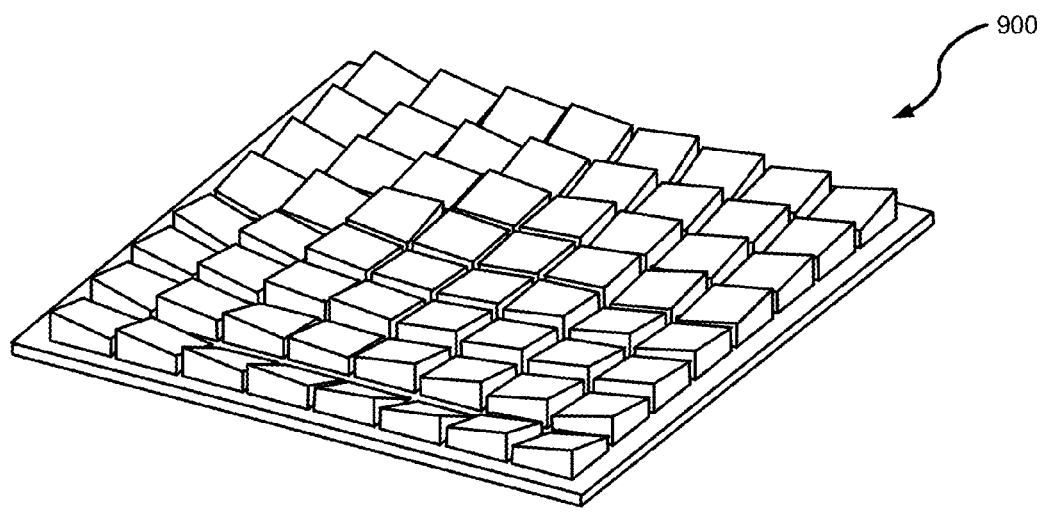
FIG. 9A shows a schematic drawing of an orthogonal view of another example of a mirror array, in accordance with some implementations.
Figure 9B:
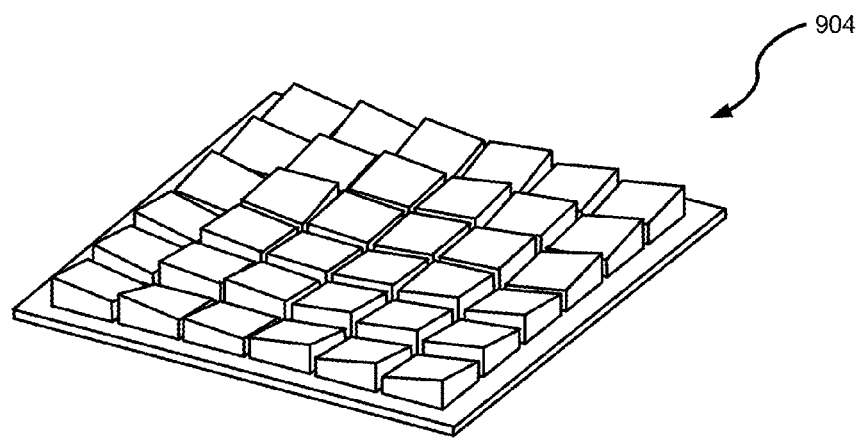
FIG. 9B shows a schematic drawing of an orthogonal view of another example of a mirror array, in accordance with some implementations.

As described above, mirror arrays in angular direction devices of LFP Imaging systems can take a wide variety of shapes and sizes. By way of example, FIGS. 9A and B show examples of an 8×8 mirror array 900 and a 6×6 mirror array 904, respectively, according to embodiments.

While FIGS. 5-9B show various examples of shapes and sizes of mirror arrays in angular direction devices of LFP Imaging systems, such mirror arrays are not limited to the bowl-shaped surface, flat concentric circular ring surface, and/or flat rectangular surface arrangements shown in FIGS. 5-9B, respectively. Rather, such mirror arrays may take any symmetric or asymmetric round or polygonal shape, e.g. a rectangle, an octagon, an oval, an ellipse, etc.

II. LFP Imaging Methods

Figure 11:
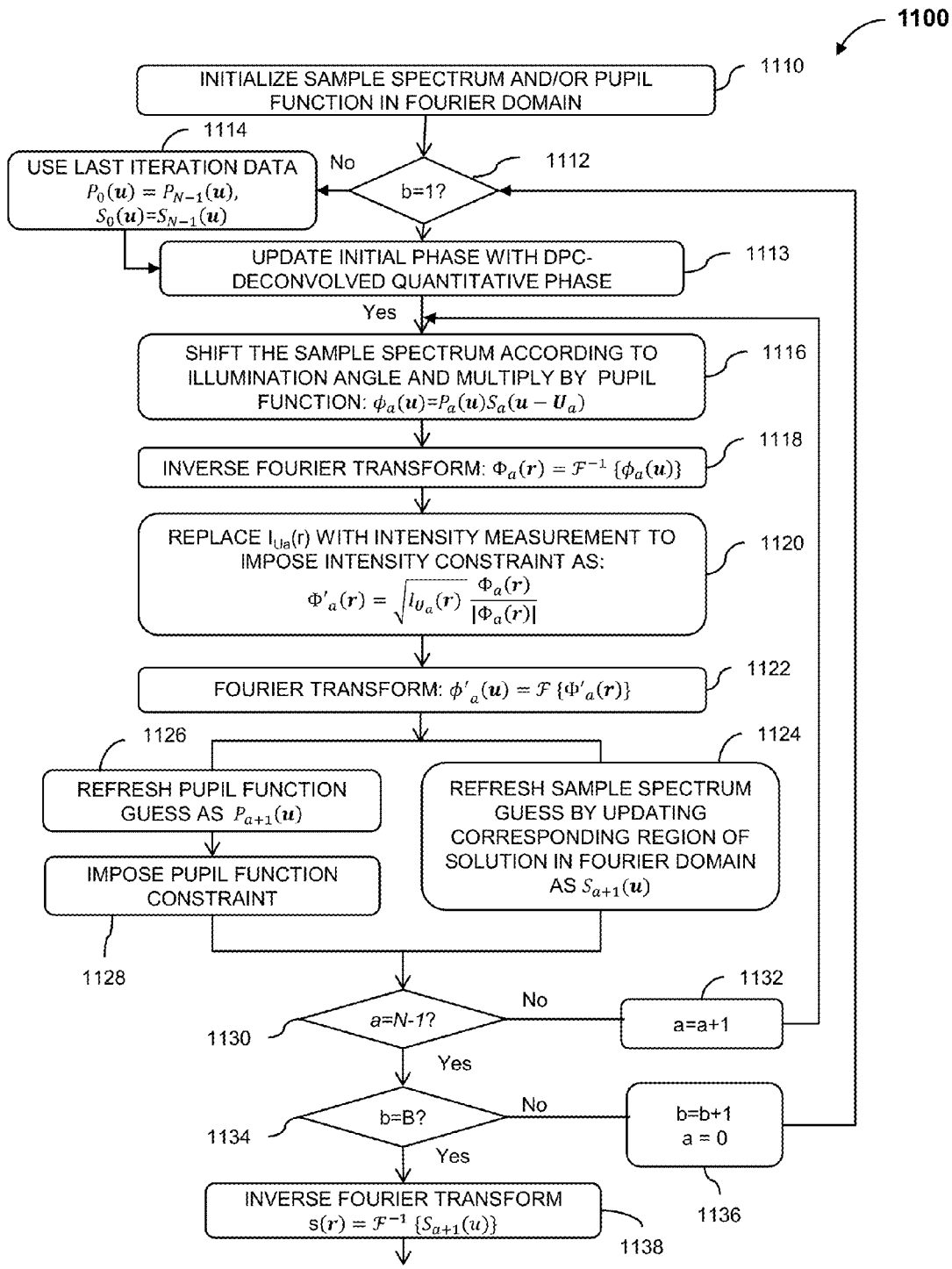
FIG. 11 shows a flowchart depicting details of operations of an LFP imaging method that implements DPC deconvolution, in accordance with some implementations.

According to certain implementations, the LFP imaging method discussed in the context of FIG. 11 operates most effectively for a thin sample. The thinness of the sample depends on the bigger value between the illumination NA and the objective NA. In one case, the thinness can be related to these value by pi/(kzmax) where kzmax is defined by max(k0^2-sqrt(k0^2-(k0*NAobj)^2), k0^2-sqrt(k0^2-(k0*NAillu)^2)) which is described in Ou, Xiaoze et al., "High numerical aperture Fourier ptychography: principle, implementation and characterization," Optics Express, p 3472-3492 (Feb. 9, 2015). For example, for NAillu=0.7 and NAobj=0.5, hmax will be 1.75*lambda, which corresponds to 822 nm for lambda=470 nm. The sample may be thicker than this in many cases.

For thin samples, the sample may be approximated as two dimensional, similar to a thin transparent film with a particular absorption and phase profile. In a general application of LFP methods to a specific implementation using an optical system such as optical system 120 of FIG. 1 (e.g. a 4f microscope), when a sample is on a specimen surface (e.g. on the stage of the 4f microscope) it may be perpendicularly illuminated by a light source that is coherent both temporally (i.e. monochromatic) and spatially (i.e. plane wave). The light field scattered by features of the sample the sample is Fourier transformed when it passes through the collection optical element of the optical system (e.g. objective lens microscope) and arrives at the back-focal plane of the collection optical element. The field is then Fourier transformed again as it propagates through the focusing optical element (e.g. a microscope's tube lens) to be imaged onto a light detector (e.g. a camera sensor or in a microscopist's eyes). The amount of the sample's detail that the optical system can capture is defined by the NA ($NA_{obj}$) of the collection element, which physically limits the extent of the sample's Fourier spectrum being transmitted to the light detector. Thus, the $NA_{obj}$ acts as a low-pass filter in the optical system with a coherent illumination source.

For illustrative purposes, the following discussion is limited to a one dimensional case. The one dimensional case described below may be directly extended to two dimensions for a thin sample. Under the illumination of a same light source at an angle θ with respect to the sample's normal, the field at the sample plane, $\psi_{oblique}(x)$, can be described as:

$$\psi_{oblique}(x) = \psi_{sample}(x) \exp(jk_0 \sin \theta) \quad \text{(Eqn. 1)}$$

where $\psi_{sample}(x)$ is the sample's complex spatial distribution, x is a one-dimensional spatial coordinate, and $k_0$ is given by $2\pi/\lambda$ where λ is the illumination wavelength. This field is Fourier transformed by the collection element, becoming:

$$\psi_{oblique}(k) = \int_{-\infty}^{\infty} \psi_{sample}(x) \exp(jk_0 \sin \theta) \exp(-jkx) dx = \psi_{sample}(k - k_0 \sin \theta) \quad \text{(Eqn. 2)}$$

at the back-focal plane of the collection element, where $\psi_{oblique}$ and $\psi_{sample}$ are the Fourier transforms of $\psi_{oblique}$ and $\psi_{sample}$, respectively, and k is a one dimensional coordinate in k-space. $\psi_{sample}(k)$ is shown to be laterally shifted at the collection element's back-focal plane by $k_0 \sin \theta$. Because $NA_{obj}$ is physically fixed, a different sub-region of $\psi_{sample}(k)$ is relayed down the imaging system. Thus, more regions of $\psi_{sample}(k)$ are acquirable by capturing many intensity images under varying illumination angles than would be acquirable by only capturing a single image under particular illumination. Each sub-sampled Fourier spectrum from the collection element's back-focal plane is Fourier transformed again by the focusing optical element, and the field's intensity value may captured by a light detector of the imaging system.

Due to the loss of phase information in the intensity measurement, the sub-sampled images cannot be directly combined in the Fourier domain. As such, an LFP procedure, e.g. the process described below in the context of FIG. 11, may be used to reconstruct the phase and amplitude of the expanded Fourier spectrum. As discussed above, an angle direction mechanism may illuminate a sample with laser light at a sequence of illumination angles such that each the intensity images overlap in Fourier space at least a certain minimum amount (e.g. 65% overlap, 75% overlap, 70% overlap, 80% overlap, in a range of 10%-65% overlap, in a range of 65%-75% overlap, etc.). This redundancy allows the LFP procedure to be used to infer the missing phase information through an iterative method which is described below in the context of FIG. 11.

A. An Exemplary LFP Imaging Method

Figure 10:
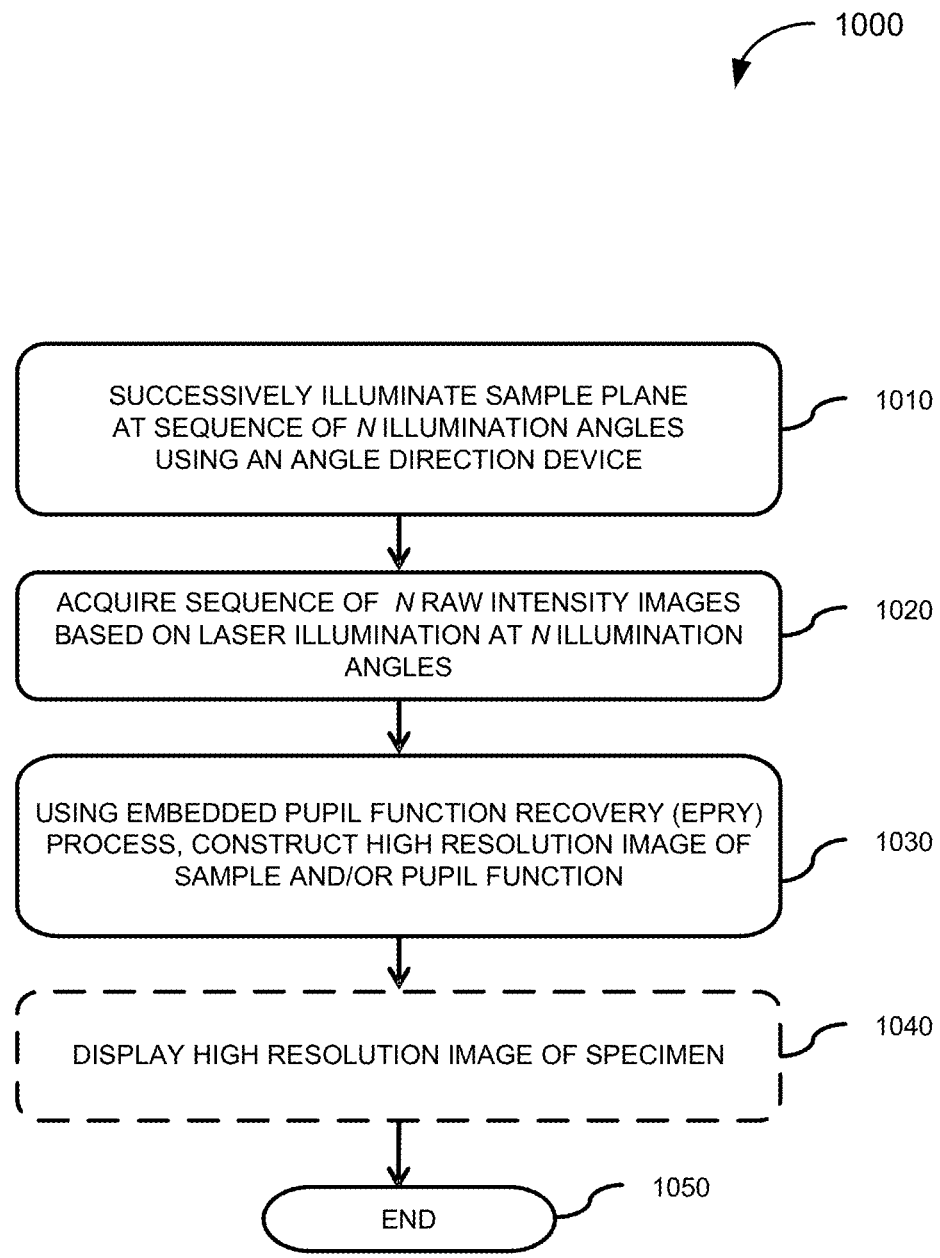
FIG. 10 shows a flowchart of an example of an LFP imaging method, in accordance with some implementations.

FIG. 10 is a flowchart of operations of an LFP imaging method 1000 that can be implemented by various LFP imaging systems described herein, in accordance with certain embodiments. At 1010, a sample plane is successively illuminated at a sequence of N illumination angles using an angle direction device to direct laser light from a laser light source. During an image acquisition phase, the sample being imaged is located at the sample plane typically on a specimen surface and the sample is illuminated at a sequence of N illumination angles using a laser light source. By way of example, as described above in the context of FIG. 6, the rotatable mirrors 613 and 614 are rotated to direct collimated laser light 604 to different mirrors 816(1)-816(95) of the mirror array 615 at different sampling times during the image acquisition phase. The different mirrors 816(1)-816(95) of the mirror array 615 reflect the collimated laser light 604 at a sequence of N illumination angles at different sample times. At each sampling time, the rotatable mirrors 613 and 614 are positioned such that they direct the collimated laser light 604 to one of mirrors 816(1)-816(95), illuminating the specimen at a sequence of 95 illumination angles.

At 1020, N raw intensity images of the sample are acquired by the light detector(s). By way of example, the light detector(s) of the imaging system 630 in FIG. 6 may capture a sequence of ninety five (95) intensity images of the sample when it is on the specimen surface 608 and while collimated laser light 604 is reflected by the ninety five (95) different mirrors 616(1)-616(95) at ninety five (95) illumination angles to the sample plane at the specimen surface 608.

In one embodiment, the light detector may also capture an additional "dark field" intensity image of the sample when the sample is not illuminated.

At 1030, a high resolution image of the sample and/or pupil function is constructed using an Embedded Pupil Function Recovery (EPRY) process with one or more processors of the FLP imaging system. An example of an EPRY process is described below in detail with reference to FIG. 11. At optional operation 1040, a display may receive image data such as the higher-resolution image data and/or other data, and display the data on a display (e.g., display 152 of FIG. 1). Then, the LFP method ends (1050) an imaging cycle.

FIG. 11 is a flowchart depicting operations of an exemplary EPRY process 1100, according to embodiments. At operation 1110, the sample spectrum and pupil function are initialized as $S_0(u)$ and $P_0(u)$ respectively. In addition, the outer loop index variable, b, is set to 1 (first iteration) and the inner loop index variable, a, is set to 0. Outer loop index variable, b is the index incrementing the reconstruction process iterations and inner loop index variable, a, is the index incrementing the incidence angle. In the cycles of the inner loop, N acquired raw intensity images are addressed in the sequence: $I_{U_a}(r)$, a=0 to N−1, where N is the number of acquired images, and each is considered in turn, with both the pupil function and sample spectrum updated at each loop.

In one embodiment, the initial sample spectrum $S_0(u)$ may be determined by first initializing a sample image in the spatial domain, and then applying a Fourier transform to obtain an initialized sample spectrum in the Fourier domain. In some cases, the initial guess may be determined as a random complex matrix (for both intensity and phase). In other cases, the initial guess may be determined as an interpolation of the low-resolution intensity measurement with a random phase. An example of an initial guess for $S_0(u)$ may be interpolated from one of the captured intensity images. Another example of an initial guess is a constant value. The Fourier transform of the initial guess can be a broad spectrum in the Fourier domain.

In one embodiment, the initial pupil function guess $P_0(u)$ may be a circular shaped low-pass filter, with all ones inside the pass band, zeros out of the pass band and uniform zero phase. In one example, the radius of the pass band is NA×2π/λ, where NA is the numerical aperture of the filtering optical element (e.g., objective lens) and λ is the illumination wavelength. An example of an initial pupil function guess would be based on assuming the system is aberration free, phase=0.

At operation 1112, it is determined whether b=1 i.e. it is the first iteration of the outer loop. If it is determined that it is not the first iteration, then the initial pupil function and the sample spectrum in the Fourier domain are set to the data determined in the last cycle of the inner loop: $S_0(u)=S_{M-1}(u)$ and $P_0(u)=P_{M-1}(u)$ at operation 1114.

If it is determined that it is the first iteration at operation 1112, then the EPRY process proceeds to operation 1113. At operation 1113, using a processor, a differential phase contrast (DPC) deconvolution procedure is applied. DPC deconvolution is a partially coherent method to acquire the quantitative phase of a sample. DPC deconvolution is based on the assumption that the absorption and phase of a specimen being imaged are small such that the specimen's complex transmission function, $\psi(x)=\exp(-\mu(x)+j\theta(x))$ can be approximated as $\psi(x)\approx1-\mu(x)+j\theta(x)$. Under this condition, performing arithmetic operations on the intensity images captured at different illumination angles generates multiple-axis DPC images and a transfer function associated with the specimen's phase and DPC images. De-convolving the transfer function from the DPC images results in the quantitative phase image of the sample with the spatial frequency information extending to $2k_0NA_{obj}$ in k-space.

The phase of the initial guess is updated with the DPC-deconvolved quantitative phase as: $\psi_{2NA}(x)=|\mathcal{F}\{\Psi(k)P_{2NA}(x)\}|\exp(j\theta_{DPC})$ where $\Psi(k)$ is the high-resolution Fourier spectrum of a sample, $P_{2NA}$ is the low-pass filter with the spatial frequency extent of $2k_0NA_{obj}$ in k-space, is Fourier transform operator, $\theta_{DPC}$ is the quantitative phase obtained from DPC deconvolution, and $\psi_{2NA}$ is the simulated image with its phase updated with $\theta_{DPC}$. Unlike intensity image updates in techniques without using a DPC-updated phase, an update with the phase from DPC deconvolution requires use of a pupil function extending to $2 NA_{obj}$ instead of just $NA_{obj}$ because the deconvolved phase contains information up to $2 NA_{obj}$ resolution.

Intensity images captured at different angles are used to reconstruct the high resolution Fourier spectrum and the pupil function of the microscope as done in earlier versions of the FP techniques. DPC phase needs to be recalculated at the beginning of each iteration of process 1100 because the pupil function of the microscope changes during pupil function update procedure.

Further details of an example of an DPC deconvolution process can be found in L. Tian and L. Waller, "Quantitative differential phase contrast imaging in an LED array microscope," Opt. Express 23(9), 11394-11403 (2015), which is hereby incorporated by reference for the discussion herein.

In certain embodiments, DPC deconvolution is included in an LFP imaging method to address low spatial frequency artifacts or "speckle noise" that may be introduced when a laser light source is used. Such artifacts may be optionally removed through use of DPC deconvolution because DPC deconvolution is a partially coherent method and is, therefore, robust to such speckle noise.

Figure 12:
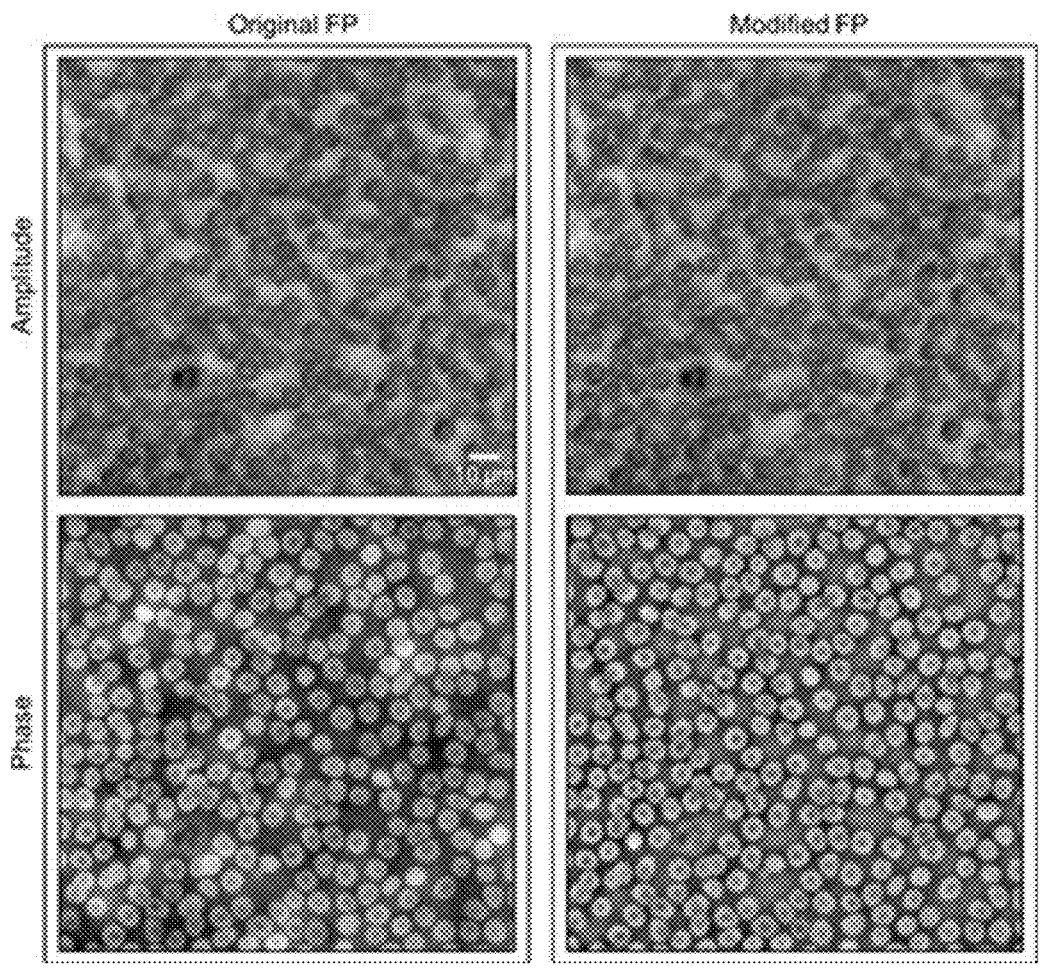
FIG. 12 shows an example of a side-by-side comparison of LFP reconstructed images that have been enhanced with DPC deconvolution and LFP reconstructed images that have not been enhanced with DPC deconvolution, in accordance with some implementations.

By way of illustration, FIG. 12 shows an example of a side-by-side comparison of LFP reconstructed images (both phase and amplitude) of cells that have been enhanced using a DPC procedure and LFP reconstructed images (both phase and amplitude) of the same cells that have not been enhanced using a DPC procedure. As shown, the images for which optional DPC-deconvolution was not used in the reconstruction process, the resulting phase image of the sample shows an uneven background signal, producing speckles in the cells' phase amplitude. On the other hand, in the images for which optional DPC-deconvolution was used in the reconstruction process, the background is uniform and the cells show similar phase values. Notably, the modification has little to no effect on the amplitude image.

Returning to FIG. 11, in the $a^{th}$ cycle of the inner loop, with the knowledge of the reconstructed $S_a(u)$ and $P_a(u)$ from the previous cycle of the inner loop, the exit wave at the pupil plane while the sample is illuminated by a wavevector $U_n$ can be simulated using: $\phi_a(u)=P_a(u)S_a(u-U_n)$ with the $S_a(u)$ and $P_a(u)$ from the previous cycle. At operation 1116, the processor shifts the sample spectrum according to the illumination angle and multiplies by the pupil function according to: $\phi_a(u)=P_a(u)S_a(u-U_n)$. The pupil function comprises both an amplitude and a phase factor. The phase factor of the pupil function is generally associated with defocus or other aberration associated with the optical system. The amplitude of the pupil function is usually associated with the objective lens aperture shape of the optical system. By multiplying the sample spectrum by the pupil function in the Fourier domain, the processor(s) both filters the higher-resolution solution by multiplying by the modulus (computed amplitude component) of the pupil function and also multiplies by the phase factor of the pupil function. Multiplying the sample spectrum by the modulus filters the higher-resolution image in the Fourier domain for a particular plane wave incidence angle $(\theta_x^a, \theta_y^a)$ with a wave vector $U_a=(k_x, k_y)$. An image captured with illumination $U_a$ based on the $a^{th}$ illumination incidence angle is referred to in this section as $I_{U_a}(r)$. By multiplying the sample spectrum by the modulus, the processor(s) filters a region from the sample spectrum $S(u)$ in the Fourier domain. In cases with a filtering optical element in the form of an objective lens, this region takes the form of a circular pupil aperture with a radius of $NA*k_0$, where $k_0$ equals $2\pi/\lambda$ (the wave number in vacuum), given by the coherent transfer function of an objective lens. The center of the circular region in Fourier space corresponds to the associated illuminating incidence angle of this $a^{th}$ cycle of the inner loop. For an oblique plane wave incidence with a wave vector $U_a=(k_x, k_y)$, the region is centered about a position $(k_x, k_y)$ in the Fourier domain.

At operation 1118, the processor takes the inverse Fourier transform as follows: $\phi_a(r)=F^{-1}\{\phi_a(u)\}$. At operation 1120, the processor imposes an intensity constraint. In this operation 1120, the modulus (computed amplitude component) of the simulated region in Fourier space is replaced with the low resolution intensity measurement $I_{U_a}(r)$ captured by the radiation detector associated with an illumination wavevector $U_a$. The computed amplitude component is replaced by the square-root of the real intensity measurement $I_{U_a}(r)$ according to:

$$\phi'_a(r) = \sqrt{I_{U_a}(r)} \frac{\phi_a(r)}{|\phi_a(r)|}.$$

This forms an updated lower resolution image.

At operation 1122, a Fourier transform is applied to the updated lower resolution image. In this operation, an updated exit wave is calculated via a Fourier transform according to: $\phi'_a(u)=\mathcal{F}\{\Phi'_a(r)\}$.

At operation 1124, the processor refreshes the Fourier spectrum guess of the higher resolution solution by updating the exit wave data and replacing data in a corresponding region of the Fourier domain as the updated exit wave data associated with incidence wave vector $U_n=(k_x, k_y)$. The processor updates the exit wave data using a sample spectrum update function. An example of a sample spectrum update function is given by:

$$S_{a+1}(u) = S_a(u) + \alpha \frac{P_a^*(u+U_a)}{|P_a(u+U_a)|_{max}^2}[\phi'_a(u+U_a) - \phi_a(u+U_a)] \quad \text{(Eqn. 3)}$$

By using such a spectrum update function, the updated value of the sample spectrum may be extracted from the difference of the two exit waves by dividing out the current pupil function. By multiplying with the conjugates using Eqn. 3 and Eqn. 4, the sample spectrum can be separated from the pupil function so that the sample spectrum can be refreshed separately from the pupil function. In some cases, a correction is added to the sample spectrum guess with weight proportional to the intensity of the current pupil function estimate. The constant $\alpha$ adjusts the step size of the update. In one example, $\alpha=1$. During the cycles of the inner loop, the data is updated as overlapping regions in the Fourier domain.

Concurrently with operation 1124, at operation 1126 the processor refreshes the guess of the pupil function in the Fourier domain as: $P_{a+1}(u)$. An example of a pupil update function that can be used here is given by:

$$P_{a+1}(u) = SP_a(u) + \beta \frac{S_a^*(u+U_a)}{|S_a(u+U_a)|_{max}^2}[\phi'_a(u) - \phi_a(u)] \quad \text{(Eqn. 4)}$$

The constant $\beta$ adjusts the step size of the pupil function update and $\beta=1$ is used in this paper. Using this pupil update function, the correction of the pupil function is extracted from the difference of the two exit waves by dividing out the current sample spectrum estimate, and added to the current pupil function guess with weight proportional to the intensity of the current sample spectrum estimate. By multiplying by the conjugate using Eqn. 4, the pupil function can be separated from the sample spectrum and refreshed separately.

At operation 1128, the processor imposes a pupil function constraint on the updated pupil function. Imposing the pupil function constraint may suppress noise. In the example of a microscope system, a physical circular aperture stop may be set to define the NA, thus the area in the pupil function that corresponds to the stop should always be zero. The non-zero points in the updated pupil function in the region corresponding to the stop are caused by the noise in image acquisition, and are set to zero to eliminate the noise.

The inner loop of the method continues to cycle until all N captured images in the sequence $I_{U_a}(r)$ are used to update the pupil and sample spectrum, at which point an iteration of the outer loop is complete. The cycles run from $a=0$ to $N-1$. At operation 1130, the processor determines whether $a=N-1$. If the processor determines that a does not equal $N-1$, then not all the N captured images have been used. In this case, the loop index a will be incremented at operation 1132, and the method will return to operation 1116 based on the next captured image associated with another incidence angle.

If the processor determines that a does equal $N-1$, the method continues to operation 1134. If the processor determines that a does not equal $N-1$, the method continues to operation 1132. At operation 1132, the outer loop index is incremented $a=a+1$ to the next incidence angle. The method will then return to start a new cycle at operation 1116.

At operation 1134, the processor determines whether $b=B$. If the processor determines that b does not equal B, the loop index b will be incremented at operation 1136 to $b=b+1$ and the loop index a will be reset to 0. The method will then return to start a new iteration at operation 1112.

If the processor determines that b does equal B, then the iterations stop and the LFP method continues to operation 1138. At operation 1138, the sample spectrum is inverse Fourier transformed back to the spatial domain to generate image data for the improved resolution image of the specimen. Both the image data for the improved resolution image of the specimen and the pupil function are output of the EPRY process. The pupil function that we are left with at the end of the operation (i.e. $b=B$) is the output for the reconstructed pupil function.

III. Experimental Results

Figure 13A:
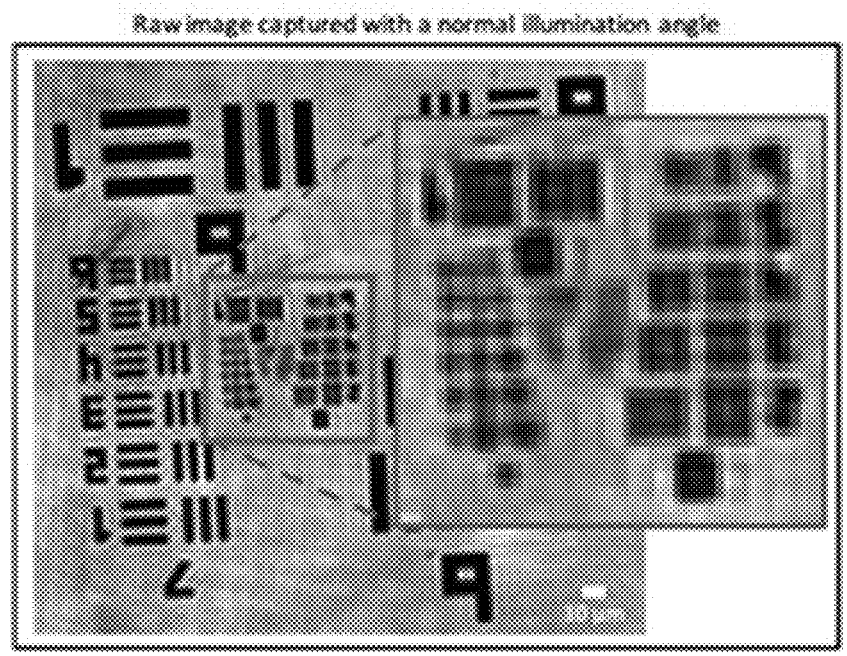
FIG. 13A shows an example of a raw image of a sample acquired by an LFP imaging system, in accordance with some implementations.
Figure 13B:
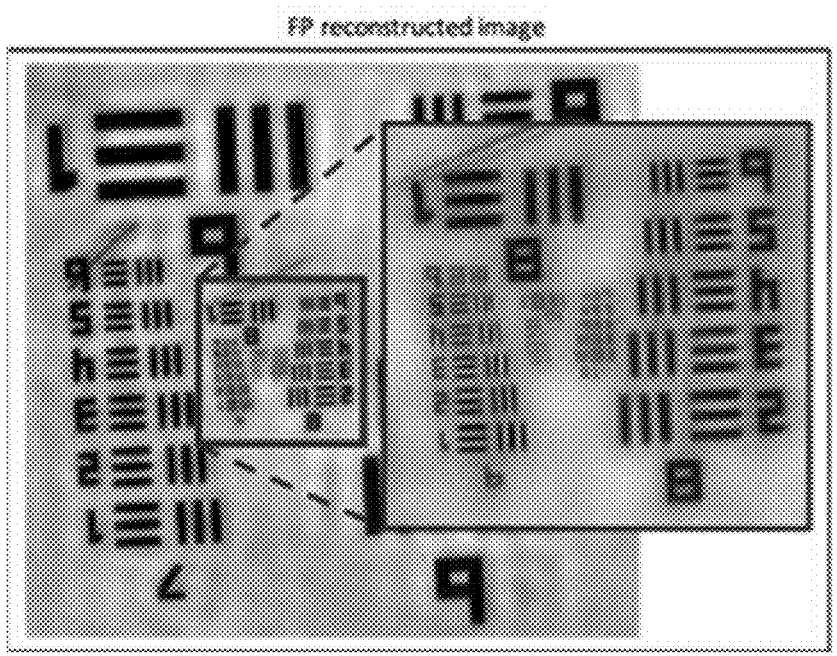
FIG. 13B shows an example of an LFP reconstructed high resolution image of the sample of FIG. 13A, in accordance with some implementations.

An LFP imaging system similar to the LFP imaging system 600 shown in FIG. 6 was used to perform the LFP imaging method 1000 described with respect to FIGS. 10 and 11 to generate high resolution of a sample a sample. FIG. 13A shows a raw image of the sample, and FIG. 13B shows an re-constructed image of the sample generated using the LFP imaging method 1000 of FIG. 10, performed using the particular implementation of LFP imaging system 600 of FIG. 6, described above. The re-constructed image shown in FIG. 12B includes resolvable features corresponding to 1.1 µm periodicity. Since periodicity is calculated by dividing λ (the wavelength of the laser illumination) by NA, a 1.1 µm periodicity is consistent with the calculated NA of 0.425 of the particular implementation of LFP imaging system 600 of FIG. 6, which uses 457 nm laser illumination, as described above. As such, in this particular implementation, LFP imaging system 600 has been shown to have an NA that is approximately 4.25 times the NA of collection element 622.

Figure 14:
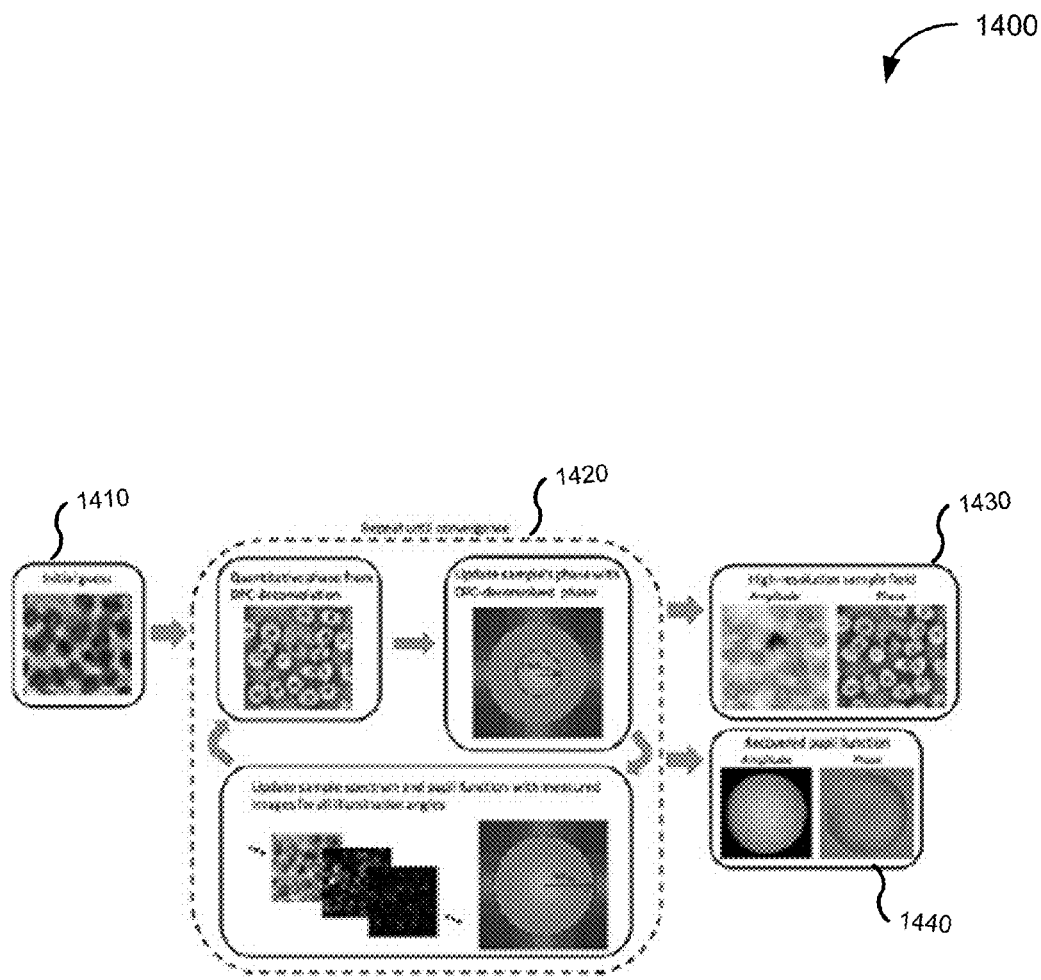
FIG. 14 shows a schematic representation of a phase and amplitude reconstruction process during the performance of an LFP imaging method, according to an implementation.

FIG. 14 shows a schematic representation of a phase and amplitude reconstruction process 1400 during the performance of an LFP imaging method, according to an implementation. As depicted in FIG. 14, the reconstruction begins at 1410 with a raw image of a sample captured with the illumination from the center mirror element 816(1) of FIG. 6 as an initial guess of the sample field. The iteration process starts by forming the sample's quantitative phase image with 2 NA resolution by DPC deconvolution with the initial guess of the pupil function, as described above in the context of FIG. 11. At 1420 of FIG. 14, the phase of the sample field up to the 2 NA resolution extent is updated, as described above in the context of FIG. 11. In the end of process 1400 of FIG. 14, the complex sample field 1430 and the pupil function 1440 are reconstructed.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

As used herein, the conjunction "or" is intended herein in the inclusive sense where appropriate unless otherwise indicated; that is, the phrase "A, B or C" is intended to include the possibilities of A, B, C, A and B, B and C, A and C and A, B and C. Additionally, a phrase referring to "at least one of" a list of items refers to any combination of those items, including single members. As an example, "at least one of: A, B, or C" is intended to cover: A, B, C, A-B, A-C, B-C, and A-B-C.

What is claimed is:

1. A laser-based Fourier ptychographic imaging system, comprising:
    an angle direction device configured to direct laser light from a laser light source to a specimen surface at a sequence of illumination angles;
    an optical system comprising a collection element and a focusing element, the collection element configured to receive light issuing from a specimen when it is located on the specimen surface, wherein the sequence of illumination angles and a numerical aperture of the collection element correspond to overlapping regions in a Fourier domain; and
    a light detector configured to receive light focused by the focusing element from the optical system and acquire a plurality of intensity images of the specimen when it is located on the specimen surface and illuminated, each intensity image corresponding to a different illumination angle of the sequence of illumination angles.

2. The laser-based Fourier ptychographic imaging system of claim 1, further comprising a processor configured to execute instructions for iteratively updating overlapping regions in the Fourier domain with the plurality of intensity images acquired by the light detector.

3. The laser-based Fourier ptychographic imaging system of claim 1, wherein the plurality of intensity images are acquired in less than 1 second.

4. The laser-based Fourier ptychographic imaging system of claim 2, wherein the processor is further configured to execute instructions for filtering out low spatial frequency artifacts associated laser light by using a differential phase contrast deconvolution procedure.

5. The laser-based Fourier ptychographic imaging system of claim 1, wherein the angle direction device comprises:
    a plurality of mirrors, each fixed mirror oriented to reflect laser light at one of the plurality of illumination angles to the specimen surface; and
    one or more rotatable mirrors configured to reflect laser light from the laser light source sequentially to different mirrors of the plurality of mirrors at different sampling times,
    wherein the plurality of mirrors are oriented to reflect laser light received from the one or more rotatable mirrors to the specimen surface at the sequence of illumination angles.

6. The laser-based Fourier ptychographic imaging system of claim 5, wherein the one or more rotatable mirrors comprise:
    a first rotatable mirror configured to rotate along a first axis; and
    a second rotatable mirror configured to rotate along a second axis orthogonal to the first axis;
    wherein the first rotatable mirror is configured to reflect laser light from the laser light source to the first rotatable mirror and the second rotatable mirror is configured to reflect light from the first rotatable mirror to one of the plurality of mirrors, wherein the first rotatable mirror and second rotatable mirror are configured to rotate to direct laser light to different mirrors of the plurality of mirrors to direct laser light at the sequence of illumination angles.

7. The laser-based Fourier ptychographic imaging system of claim 5, wherein the one or more rotatable mirrors comprise a dual axis rotatable mirror configured to rotate along two orthogonal axes to reflect laser light from the laser light source to different mirrors of the plurality of mirrors to direct laser light at the sequence of illumination angles.

8. The laser-based Fourier ptychographic imaging system of claim 5, wherein the plurality of mirrors are arranged in concentric rings along a bowl-shaped surface.

9. The laser-based Fourier ptychographic imaging system of claim 5, wherein the plurality of mirrors are arranged in a flat structure.

10. The laser-based Fourier ptychographic imaging system of claim 5, wherein each mirror of the plurality of mirrors comprises a neutral density filter.

11. The laser-based Fourier ptychographic imaging system of claim 1, wherein the angle direction device comprises:
 a plurality of optical fibers, each optical fibers having first and second end portions; and
 one or more optical switches in optical communication with the laser light source, the one or more optical switches configured to switch at different sampling times to direct laser light from the laser light source to the first end portion of different optical fibers of the plurality of optical fibers when the laser light source is activated;
 wherein the plurality of optical pathways are configured so that each second end portion directs laser light to one of the sequence of illumination angles when the one or more optical switches is switched to the corresponding optical fiber and the laser light source is activated.

12. The laser-based Fourier ptychographic imaging system of claim 1, wherein in the angle direction device comprises:
 a movable stage; and
 an optical fiber coupled to the movable stage and optically coupled at one end to the laser light source,
 wherein the movable stage is configured or configurable to translate and/or rotate the optical fiber to direct laser light from the other end of the optical fiber to illuminate the specimen surface at the plurality of illumination angles at the different sampling times.

13. The laser-based Fourier ptychographic imaging system of claim 12, wherein the movable stage is an X-Y stage, and wherein the optical fiber is coupled to the X-Y stage with a connector.

14. The laser-based Fourier ptychographic imaging system of claim 1, wherein in the angle direction device comprises:
 one or more rotatable mirrors; and
 a lens system,
 wherein the one or more rotatable mirrors are configurable to direct the laser light from the laser light source to the specimen surface through a lens system, the lens system configured such that rotation of the one or more rotatable mirrors causes the laser light to illuminate the specimen at the sequence of illumination angles.

15. The laser-based Fourier ptychographic imaging system of claim 14, wherein the lens system comprises a first lens and a second lens, configured such that a back-focal plane of the first lens coincides with a focal plane of the second lens, and wherein at least one of the first and second lenses is a f-theta lens.

16. A laser angle direction device for directing laser light sequentially through a plurality of different illumination angles, the laser angle direction device comprising:
 a surface; and
 a plurality of mirrors coupled to the surface, each mirror oriented to receive laser light from a laser light source and reflect the laser light to one of the plurality of illumination angles to a specimen surface, wherein the laser angle direction device is configured to provide the laser light from the light source sequentially to each one of the plurality of mirrors at a different sampling time during operation.

17. The laser angle direction device of claim 16, further comprising one or more rotatable mirrors configured to reflect the laser light from the light source sequentially to each of the plurality of mirrors at different sampling times.

18. The laser angle direction device of claim 16, wherein the surface is bowl-shaped.

19. The laser angle direction device of claim 16,
 wherein the surface is flat;
 further comprising a plurality of structures attached to the flat surface,
 wherein each of the mirrors is attached to one end of one of the structures, and the other end of the structures is attached to the surface.

20. The laser angle direction device of claim 16, wherein each mirror comprises a neutral density filter.

21. A laser-based Fourier ptychographic imaging method employing a laser light source, the method comprising:
 directing laser light from the laser light source to a specimen surface located at about a sample plane using an angle direction device at a sequence of illumination angles;
 receiving light, at a light detector, issuing from a sample when the sample is located on the specimen surface, the light received from an optical system;
 acquiring a plurality of intensity images based on light received at the light detector, wherein each intensity image corresponds to one of the illumination angles; and
 constructing a higher resolution image by simultaneously updating a pupil function and a sample spectrum, wherein the sample spectrum is updated in overlapping regions with Fourier transformed intensity images, wherein each of the overlapping regions corresponds to one of the plurality of illumination angles.

22. The laser angle direction device of claim 16, wherein light issuing from a sample being imaged on the specimen surface is received by a light detector via an optical system, and wherein a plurality of images of the sample is acquired by the light detector during operation, each image based on a different illumination angle.

* * * * *